United States Patent [19]

Wadaka et al.

[11] Patent Number: 5,203,823
[45] Date of Patent: Apr. 20, 1993

[54] DETECTING APPARATUS

[75] Inventors: Shusou Wadaka; Koichiro Misu; Tsutomu Nagatsuka; Mitsuhiro Koike, all of Kanagawa, Japan

[73] Assignee: Mitsubishi Denki Kabushiki Kaisha, Japan

[21] Appl. No.: 486,006

[22] Filed: Feb. 27, 1990

[30] Foreign Application Priority Data

Feb. 28, 1989 [JP] Japan .................................. 1-45316
Apr. 5, 1989 [JP] Japan .................................. 1-86383
Aug. 8, 1989 [JP] Japan .................................. 1-203909

[51] Int. Cl.$^5$ .................................. G01N 29/10
[52] U.S. Cl. .................................. 73/602; 364/819; 364/728.07; 364/728.03; 364/905; 364/100
[58] Field of Search .................................. 73/602, 631, 642; 364/728.07, 728.03, 819, 821; 367/100, 905

[56] References Cited

U.S. PATENT DOCUMENTS

| | | | |
|---|---|---|---|
| 2,907,400 | 10/1959 | Swafford, Jr. | 364/819 |
| 3,968,471 | 7/1976 | Savit | 364/728.03 |
| 4,156,876 | 5/1979 | Debuisser | 364/728.07 |
| 4,167,879 | 9/1979 | Pedersen | 73/610 |
| 4,224,679 | 9/1980 | Nossen et al. | 364/728.03 |
| 4,245,326 | 1/1981 | Gutleber | 364/728.07 |
| 4,442,715 | 4/1984 | Brisken et al. | 73/626 |
| 4,471,785 | 9/1984 | Wilson et al. | 73/602 |
| 4,542,653 | 9/1985 | Liu | 73/626 |

OTHER PUBLICATIONS

"An Evaluation of Ultrasound NDE Correlation Flow Dectection Systems" IEEE Transactions on Sonics and Ultrasonics, vol. SU-29, No. 6, Nov. 1982 (pp. 359-369) by B. B. Lee and E. S. Fergason "High-Speed Digital Golay Code Flow Detection System" by B. B. Lee and E. S. Fergason, Ultrasonics Symposium, IEEE (1981) (pp. 888-891).

"Ultrasonic Testing of Materials" published by Nihon Noritsu Kyokai, Feb. 25, 1980 (pp. 177-181) (pp. 296-298).

"Coding Theory"(Basic Lecture on Computor, 18) published by Shokodo, Jun. 30, 1981 (pp. 488-492).

"High Speed Digital Golay Code Flow Detection System" by B. B. Lee and E. S. Fergason, Ultrasonics, Jul. 1983 (pp. 153-161).

"Construction and Mode of Operation of a Pulse-Echo Instrument, Sections 10.2.3-and chapter 17", (pp. 205-210, 344-347).

"Complementary Series" by Marcel T. E. Golay, IRE Transactions on Information Theory, vol. IT-7, Apr. 1961 (pp. 82-87).

Primary Examiner—Hezron E. Williams
Assistant Examiner—Rose Finley
Attorney, Agent, or Firm—Wolf, Greenfield & Sacks

[57] ABSTRACT

An ultrasonic non-destructive inspecting apparatus is constructed to comprise a transmission signal generator, an ultrasonic probe, a correlator and an adder wherein a transmission signal based on a sequence is generated and transmitted to a specimen, its echo is correlation processed with an appropriate reference signal, and the results of the correlation processes are summed to judge a reflection matter within the specimen.

47 Claims, 72 Drawing Sheets

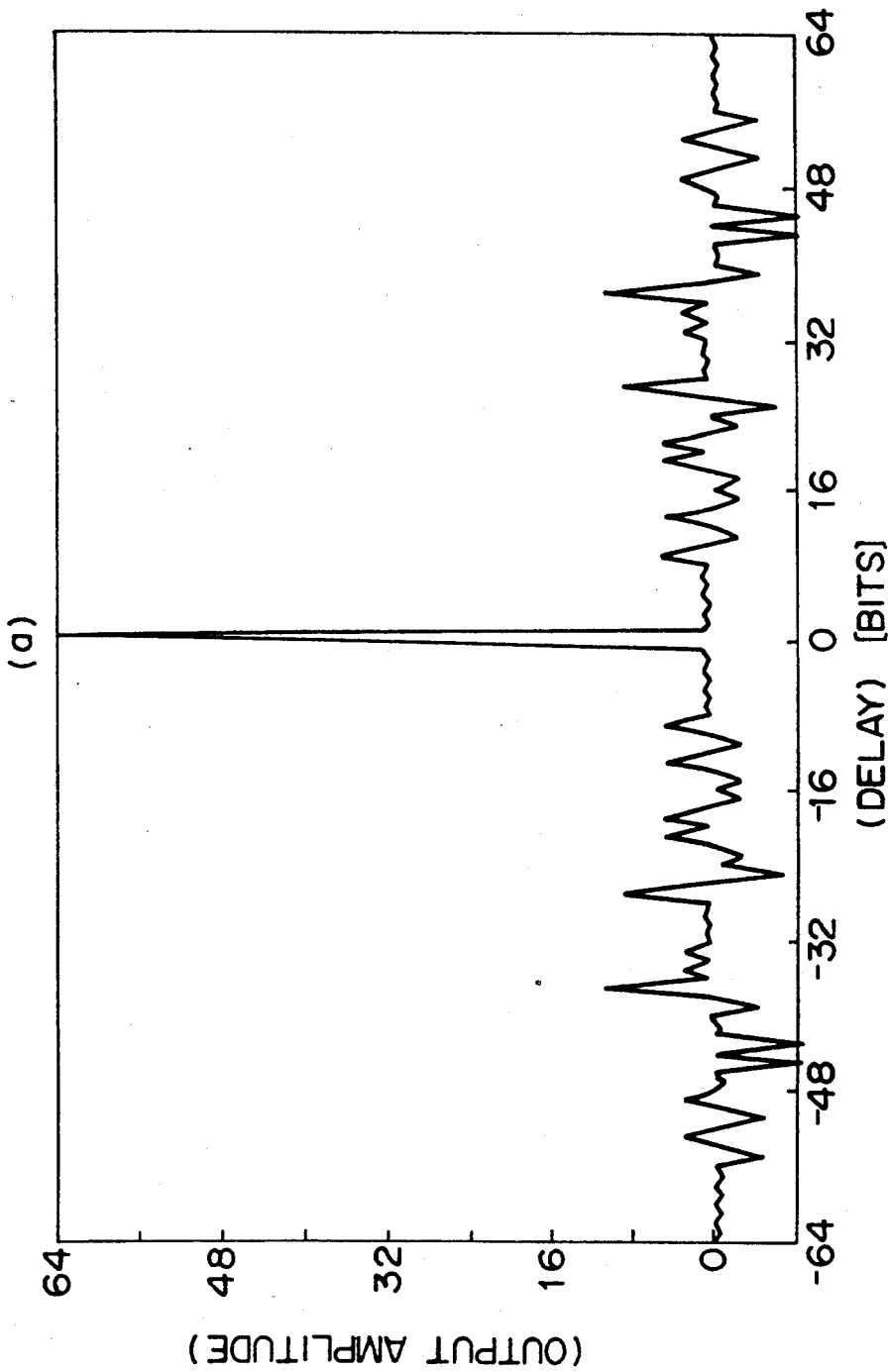

(b)

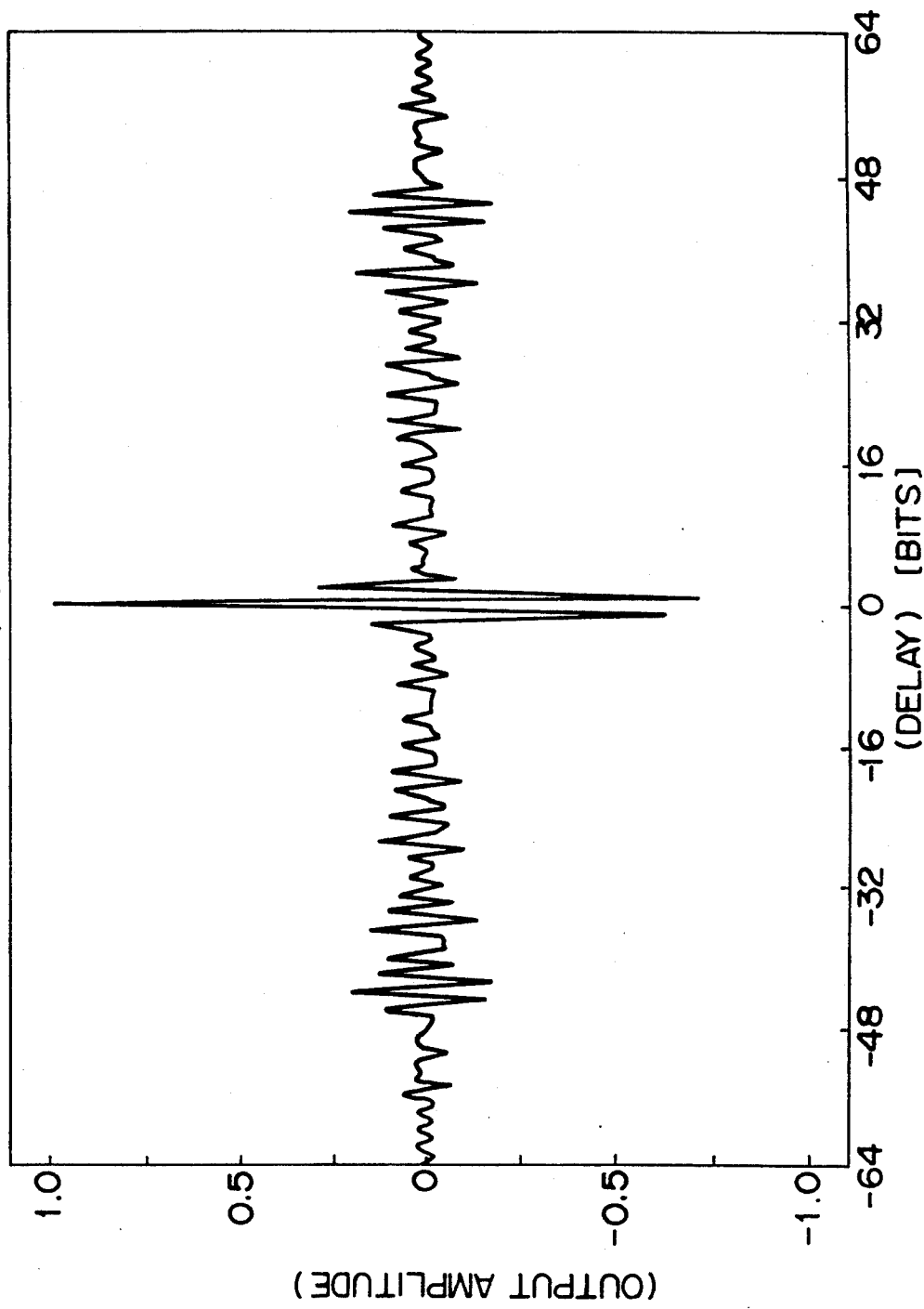

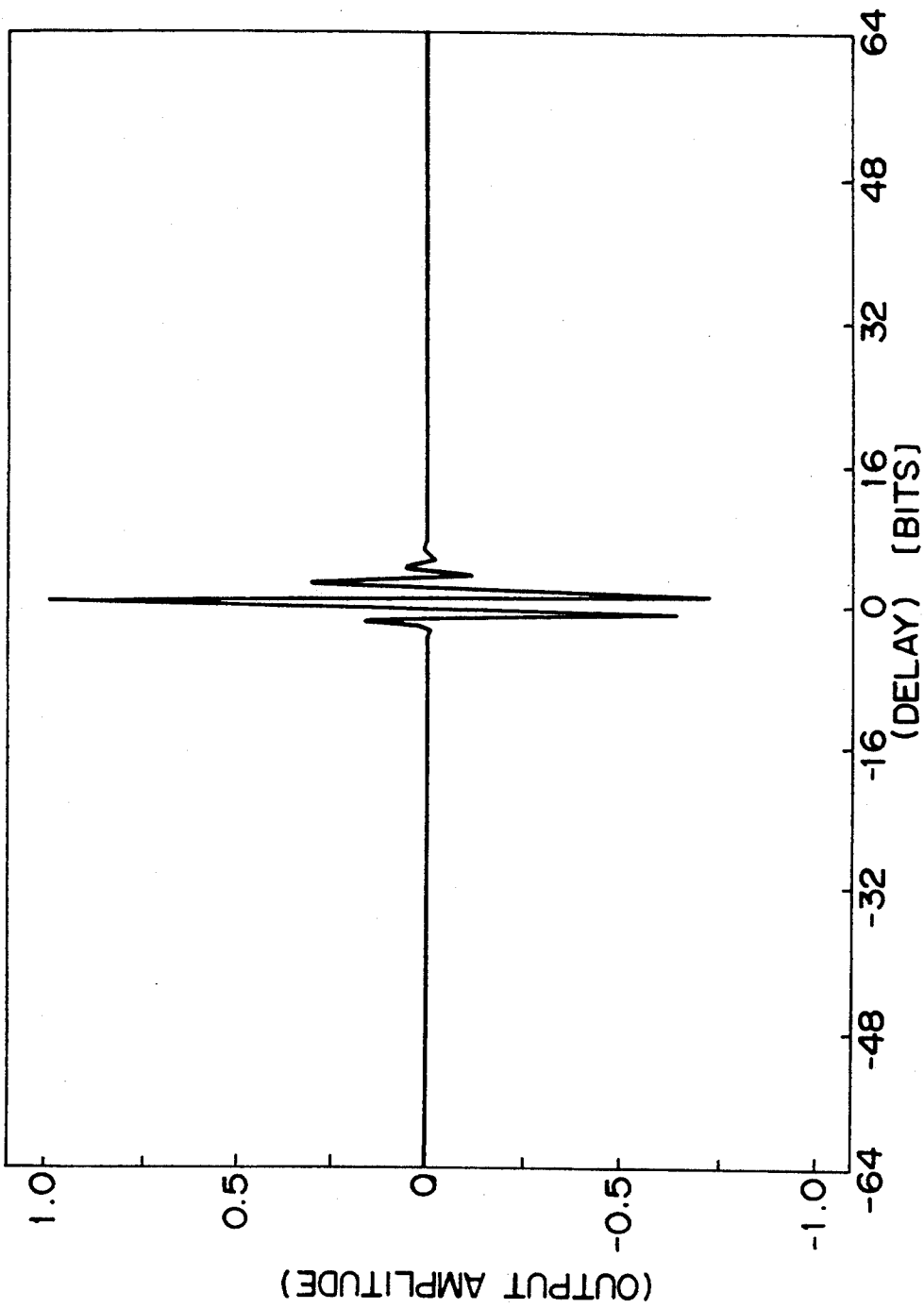

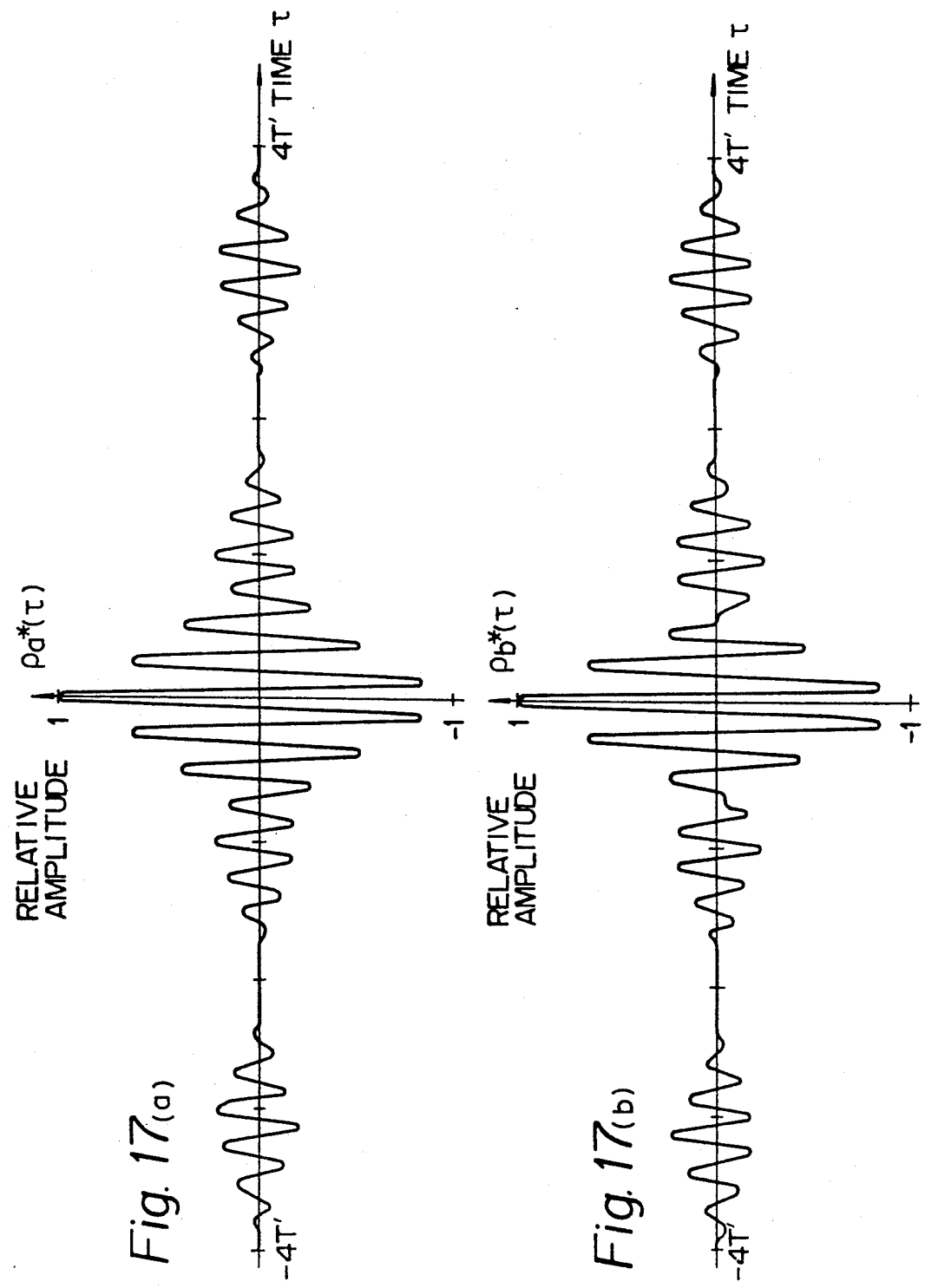

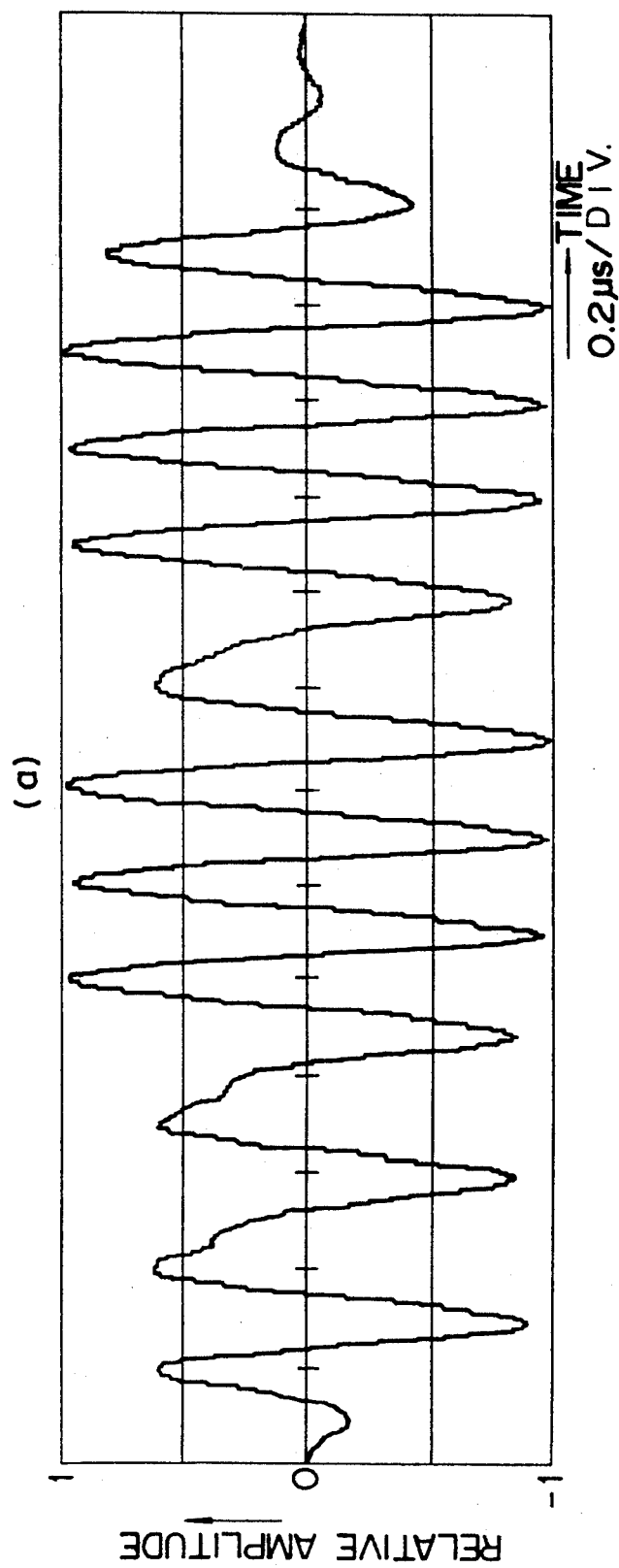

(b)

(b)

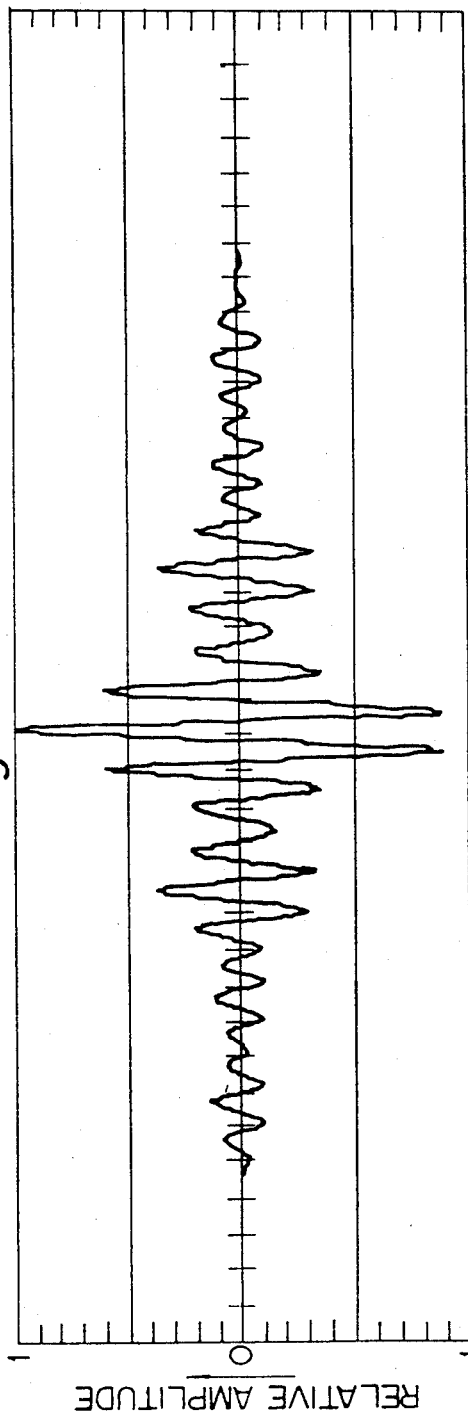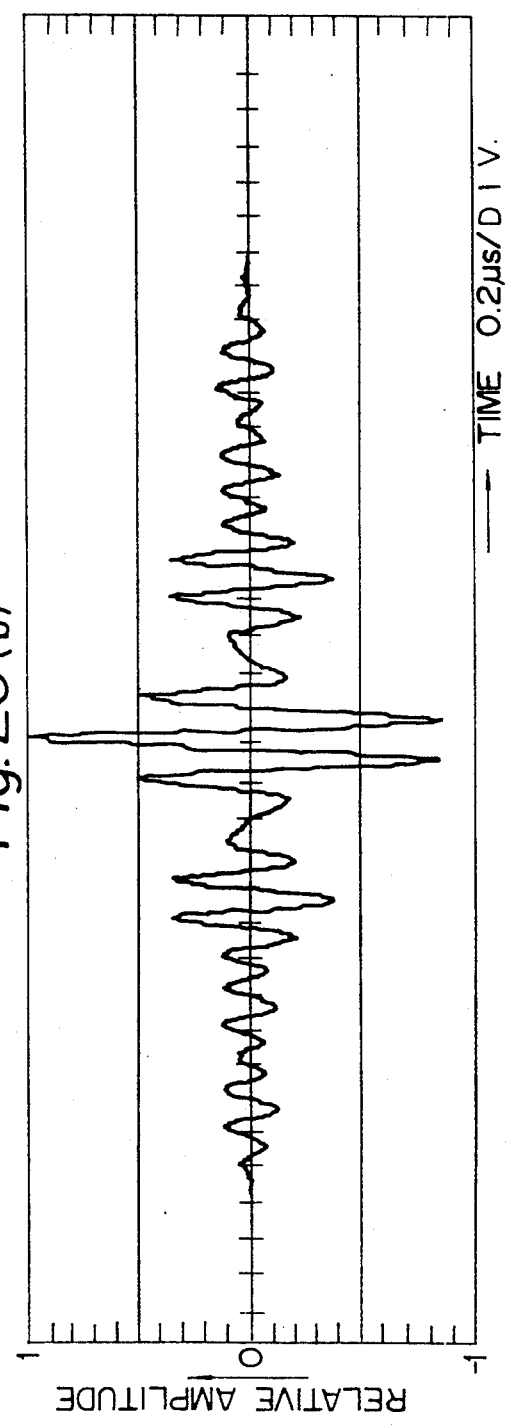

Fig. 37(a)
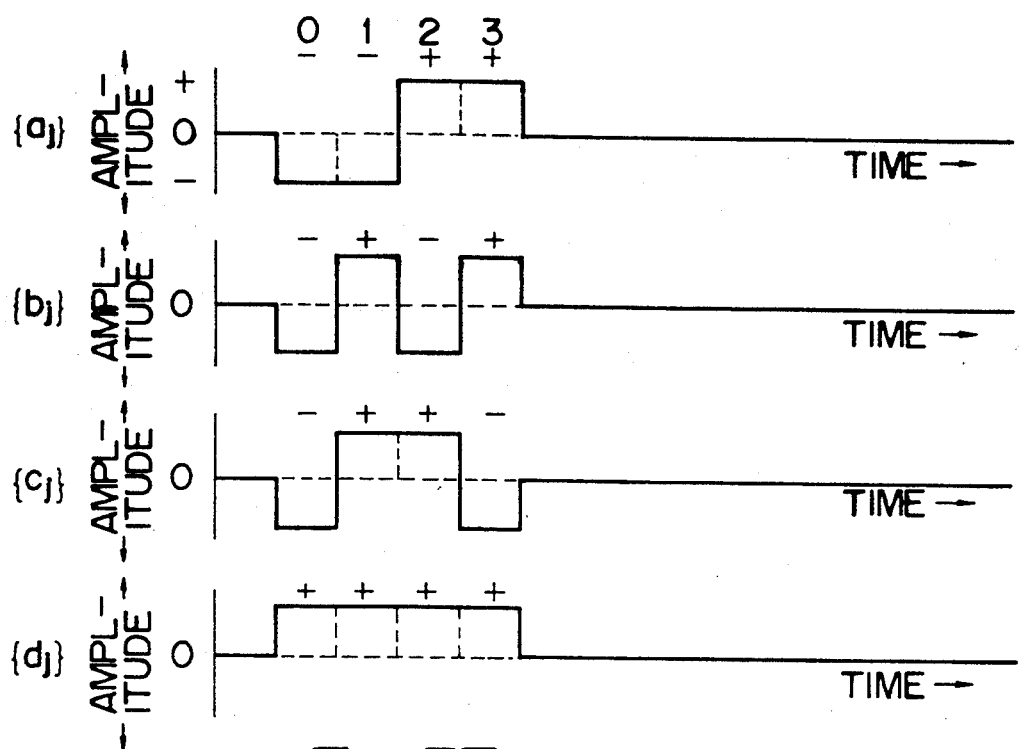
Fig. 37(b)
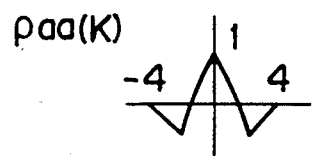
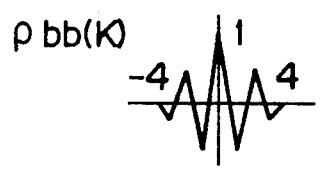
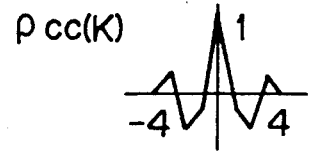
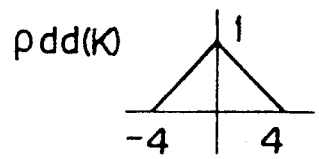
Fig. 37(c)
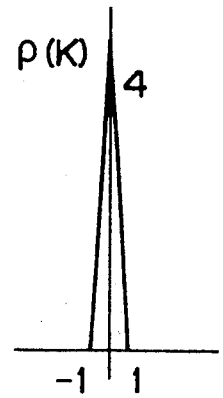

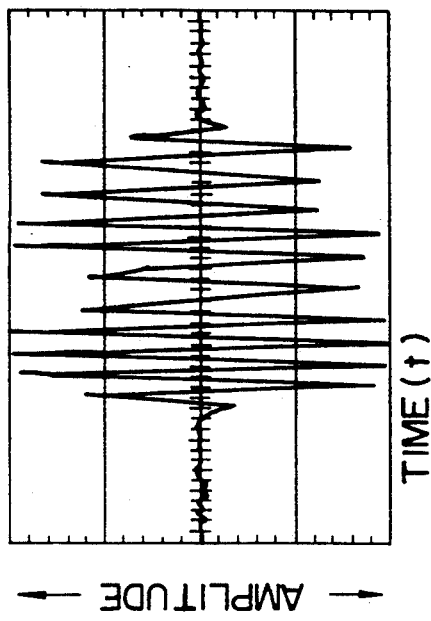
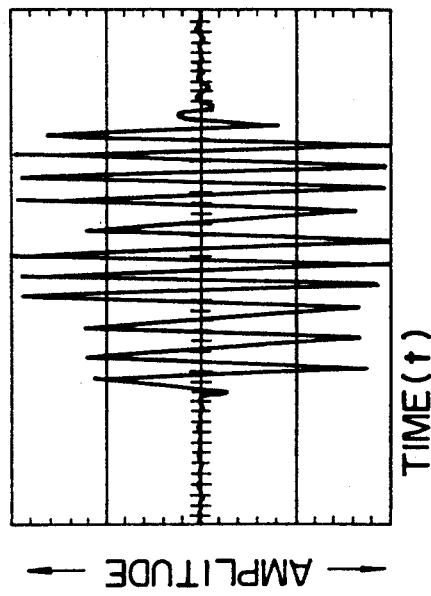
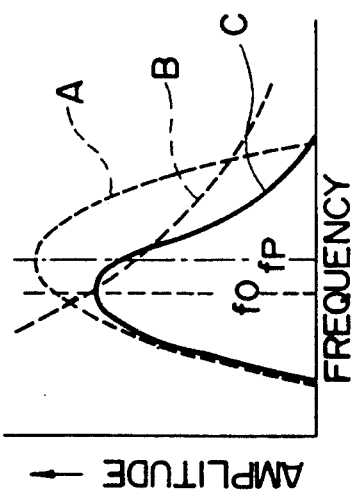

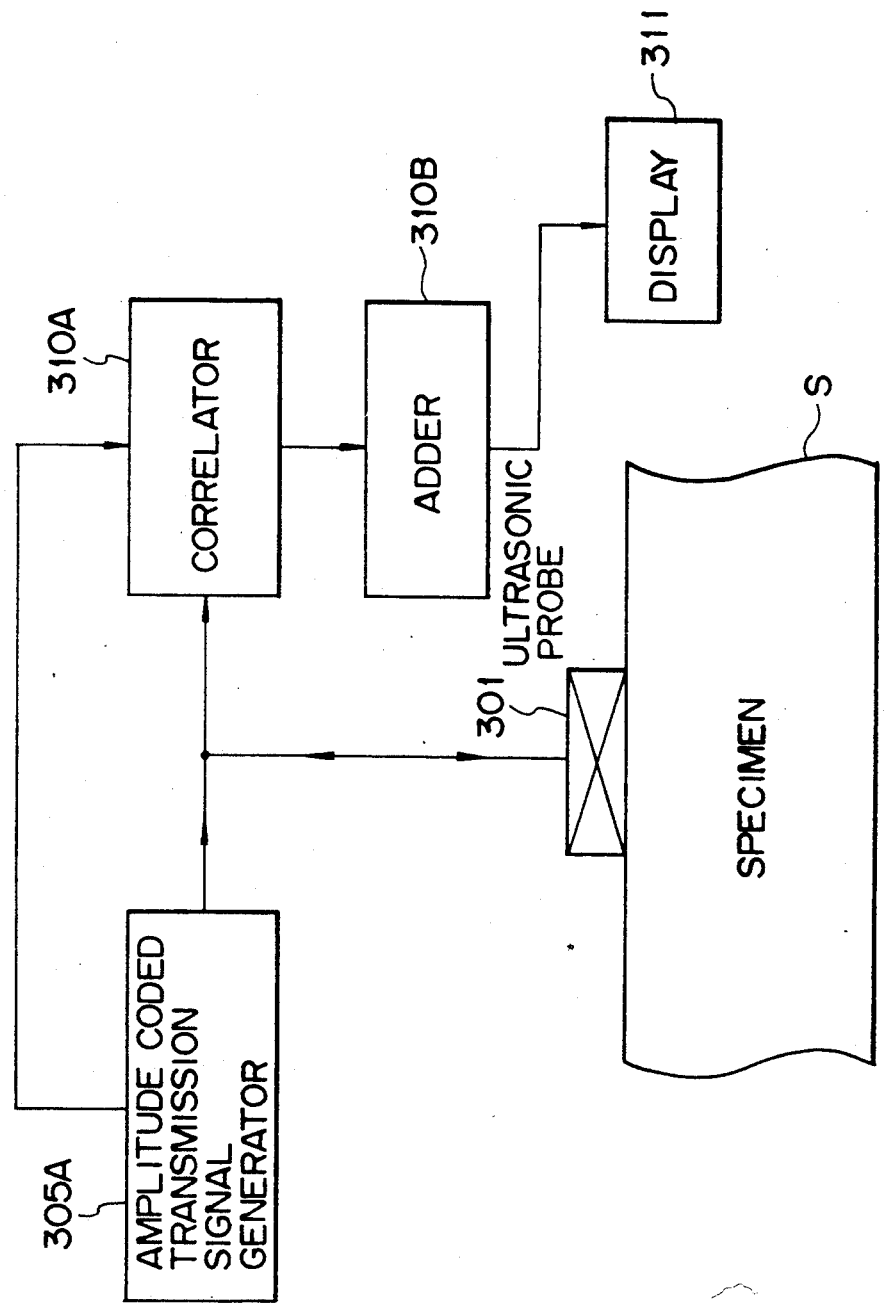

(c)

(d)

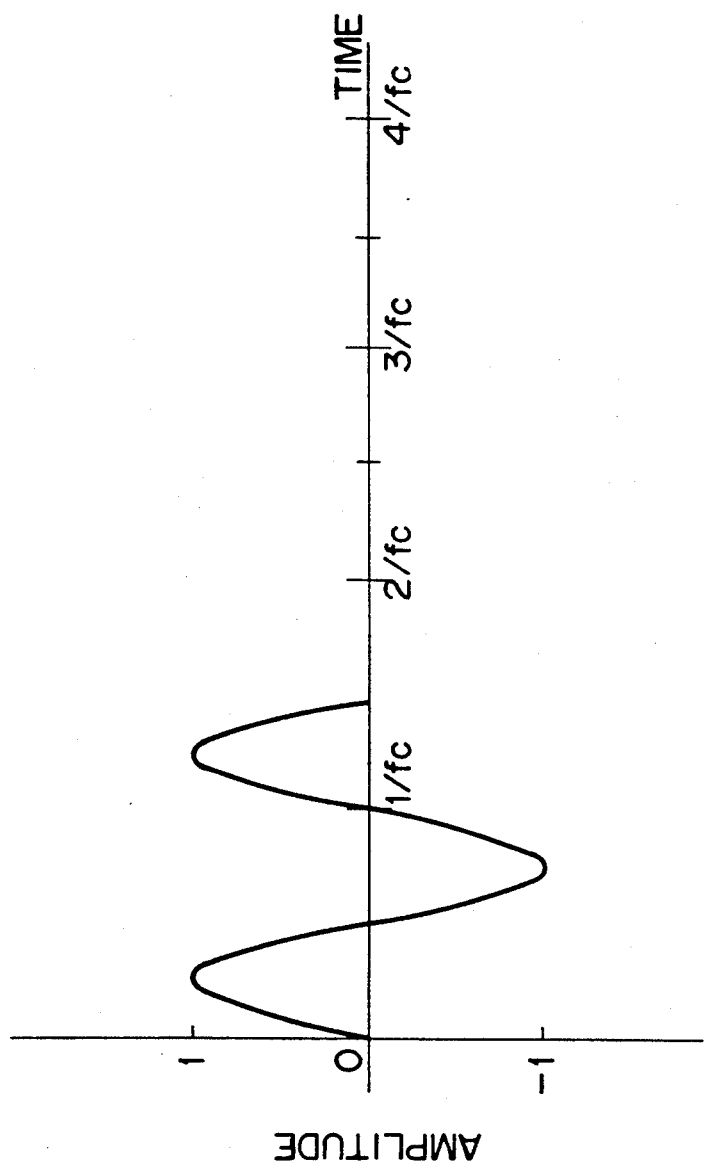

Fig. 56 (a)

| LENGTH OF SEQUENCE | COMBINATION |
|---|---|
| n = 4 | ( 1) [ 6] [ 5] [ 3] [ 0] |
|  | ( 2) [ 2] [ 2] [ 1] [ 1] |
| n = 5 | ( 1) [ 5] [ 4] [ 3] [ 2] |
|  | ( 2) [ 6] [ 5] [ 2] [ 1] |
|  | ( 3) [14] [ 5] [ 4] [ 1] |
|  | ( 4) [14] [ 9] [ 2] [ 1] |
|  | ( 5) [ 9] [ 3] [ 2] [ 2] |
| n = 6 | ( 1) [10] [ 9] [ 7] [ 4] |
|  | ( 2) [11] [ 6] [ 5] [ 4] |
|  | ( 3) [12] [11] [ 5] [ 2] |
|  | ( 4) [12] [11] [10] [ 1] |
|  | ( 5) [13] [ 6] [ 5] [ 2] |
|  | ( 6) [13] [10] [ 4] [ 3] |
|  | ( 7) [13] [10] [ 6] [ 1] |
|  | ( 8) [14] [ 9] [ 5] [ 2] |
|  | ( 9) [14] [10] [ 9] [ 1] |
|  | (10) [17] [11] [ 6] [ 2] |
|  | (11) [18] [17] [ 7] [ 4] |
|  | (12) [18] [17] [14] [ 1] |
|  | (13) [22] [12] [ 5] [ 1] |
|  | (14) [22] [17] [ 4] [ 3] |
|  | (15) [22] [17] [ 6] [ 1] |
|  | (16) [25] [10] [ 3] [ 2] |
|  | (17) [30] [13] [ 5] [ 4] |
|  | (18) [30] [17] [11] [ 4] |
|  | (19) [30] [17] [13] [ 2] |
|  | (20) [30] [25] [ 5] [ 2] |
|  | (21) [30] [25] [10] [ 1] |

| LENGTH OF SEQUENCE | COMBINATION |
|---|---|
| n = 4 | (1) [6] [5] [3] [2] [1] [0]<br>(2) [2] [2] [2] [1] [1] [1]<br>(3) [5] [3] [3] [2] [2] [0]<br>(4) [6] [6] [5] [1] [1] [0] |

(a)

(b)

(c)

(d)

DETECTING APPARATUS

BACKGROUND OF THE INVENTION

The present invention relates to an apparatus for detecting a flaw or the like within a specimen and more particularly to an apparatus for performing a non-destructive inspection utilizing transmission waves such as ultrasonic waves, electric waves or micro-waves.

Prior Art

Several aspects of prior art will be touched upon. As to the first aspect, an impulse system is often employed in a non-destructive inspecting apparatus utilizing ultrasonic waves. A construction of an example of prior art employing an impulse system is explained referring to FIG. 1.

FIG. 1 illustrates a conventional ultrasonic non-destructive inspecting apparatus in a block diagram, shown for example on pages 114-140; 173-174, "Ultrasonic Detecting Method" compiled by Steel Production 19th Committee, Nihon Gakujutsu Shinkokai published from Nikkan Kogyo Shimbunsha, Dec. 20, 1977.

In FIG 1, a conventional ultrasonic non-destructive inspecting apparatus is constructed by comprising a pulse-generating circuit 1, an ultrasonic probe 2 connected to the pulse-generating circuit 1, a receiving circuit 3 connected to the ultrasonic probe 2, and a display 4 such as CRT or the like connected to the receiving circuit.

Incidentally, the ultrasonic probe 2 is contacted with a specimen S made of steel or the like.

Next, operation of the conventional example noted above is explained referring to FIGS. 2(a), (b) and (c).

The pulse-generating circuit 1 generates pulses having short duration of vibration.

The ultrasonic probe 2 is driven by these pulses to transmit ultrasonic waves of short pulse width into the specimen S. The probe receives echo reflected within the specimen S and transmit it to the receiving circuit 3.

The receiving circuit 3 amplifies the reflection echo and transmits it to the display 4.

The display 4 displays the amplified reflection echo. As shown in FIG. 2(b), the reflection echo appears at time $t = t_0$.

The time $t_0$ is a required time for ultrasonic wave to make a round trip to a reflecting object within the specimen S and therefore it is possible to calculate a position of the reflecting object by measuring the time $t_0$. However, in the example explained above, there has been a problem in that positional detection of the reflecting object cannot be made with accurate preciseness when a level of the reflection echo is low and a level of noise overlapping the reflection echo is high, that is, an S/N ratio is not good.

One countermeasure for solving the above problem would be enlargement of a pulse amplitude for driving the probe 2. However, such countermeasure as above cannot become a perfect solution because there is an upper limitation in enlarging pulse amplitude due to reasons regarding power limitation for elements constituting the pulse-generating circuit 1 and power limitation for the probe 2 in withstanding electric power.

On the other hand, as is well known, an ultrasonic inspecting apparatus for detecting a flaw in a metallic material has been manually operated and an automatic ultrasonic inspecting apparatus has been widely introduced recently for the purpose of promoting reliability and performing an effective inspection.

However, there has been several problems in automatically inspecting flaws and one of them is to secure a good S/N ratio. While several factors are considered which make an S/N ratio worse, they may be roughly classified into two cases, namely one being the case wherein a detecting signal level is low and the other being the case wherein a level of a signal not used for detection (i.e. noise level) is high.

As to the case wherein the detecting signal level is low, it is considered in general that an input signal transmitted to a signal receiving amplifier is quite low.

Such a fact that, if the level of the detecting signal is low, it would be burried within an amplifier noise inherently produced due to thermal ion motion in a receiving signal amplifier thereby degrading the S/N ratio has been publicly known as described on pages 177-181 of "Ultrasonic Testing Technology" published from I Association–Nihon Nohritsu Kyokai, Feb. 25, 1980. In order to improve an S/N ratio in the case of a low input signal level, it is generally proposed to make an amplitude of an electric signal driving a probe larger so that the signal level is made higher. However, there is an upper limitation with respect to an electric pulse voltage because of limitation on electric elements constituting a transmitting portion and an withstand voltage of a probe. Also, it is not permissible to make an electric voltage impressed on a signal transmitting portion higher for the purpose of prohibiting it from catching fire within explosive atmosphere due to possible electric discharge.

As to the case wherein a signal level not used for detection (i.e. noise level) is high, it is noted that one of these problems is that the noise is caused from an outside source. It is well known as disclosed on pages 296-298 of "Ultrasonic Testing Technology" published from Inc. Association—Nihon Nohritsu Kyokai, Feb. 25, 1980 that intermixing of the outside electric noise into an amplifier amplifying a detection signal or a signal processing system causes to degrade reliability of the inspection. Further, it is quite rare that all the noises coming from outside can be completely removed.

As to the other case, there may be such problems as presence of interfering echo due to an internal construction of a specimen or reverberation echo interfering with a high speed inspection.

Regarding the interfering echo due to the internal construction of a specimen, it is a phenomenon experienced in the case where an internal construction of such material as stainless steel or cast iron is relatively rough. The presence of interfering echo, referred to as "Grove echo", from the internal construction observed in such a specimen as above at the time of inspecting the specimen is well known as disclosed on pages 548-553 of "Ultrasonic Inspecting Process" published from Kikkan Kogyo Shimbunsha, Jun. 1, 1984. It is difficult to find out a small flaw because situation of interfering echo fluctuates depending on the variation of manufacturing process of the specimen and/or the inspecting frequency to be used.

As to interference of echo due to reverberation which causes a problem in a high speed inspection, it becomes critical when attenuation degree of an ultrasonic signal within a specimen is low and a repetition frequency for inspection is high in an automatic inspection. Such a problem as above is encountered in a case where a subsequent transmission pulse is fed into a specimen during a time when the previous ultrasonic signal is under transmission within the specimen without being sufficiently attenuated.

This problem is understood as a phenomenon wherein the ultrasonic signal reflected at the time of previous transmission causes interference and it is generally coped with by lowering repetitive inspecting frequency which inherently accompanies a lower inspection speed or by increasing diffusion rate of an ultrasonic beam with the direction of the ultrasonic beam being slightly inclined.

Now, a conventional method hereinbefore practiced for improving an S/N ratio is explained hereunder.

It is generally considered as effective in order to improve an S/N ratio in an inspection signal to utilize correlation process. At first, the correlation process is touched upon.

FIGS. 3(a) and (b) are graphs showing an operational principle of a Barker sequence as an example of finite binary sequence having a sharp correlation function often used as a synchronizing pattern in a pulse transmission, FIGS. 4 are graphs explaining similarly to FIGS. 3, an operational principle of a complementary sequence as an example of finite binary sequence having a sharp correlation function, FIG. 5 shows a constitution of an ultrasonic inspecting apparatus performing a correlation process using a random code sequence, FIG. 6 is a drawing for explaining an operation of FIG. 5, and FIG. 7 is a graph indicating frequency characteristics of a transmitting signal, probe and specimen shown in FIG. 6.

FIGS. 3 show a Barker sequence as one of finite binary sequences having a sharp correlation function as detailedly disclosed on, for example, pages 488–480 of "Coding Theory" published from Shokodo, Jun. 30. 1981. In this case, the "binary" means that it possesses two states of "+" and "−".

A correlation function $\rho_{aa}(k)$, wherein k is variable relative to a binary sequence, is generally expressed by the following equation (1):

$$\rho_{aa}(k) = \frac{1}{n} \sum_{j=0}^{n-1} a_{j+k} \cdot a_j \quad (1)$$

where n is a length of the sequence.

In this case, a finite sequence "a" is treated as an infinite length sequence having series of "O" at the both sides as expressed by the following equation (2):

$$\{a_j\} = O \ldots O a_0 a_1 \ldots a_{n-1} O O \ldots O \quad (2)$$

Since $a_j = 0$ for the range of $j \leq -1$ and $j \geq n$, the equation (1) may be converted to the following equation (3):

$$\rho_{aa}(k) = \begin{bmatrix} \frac{1}{n} \sum_{j=0}^{n-1-|k|} a_j + |k| \cdot a_j; & |k| < n \\ 0; & |k| \geq n \end{bmatrix} \quad (3)$$

As seen from the equation (3), noise levels such as thermal noise having no correlation with the sequence may be reduced, and a correlation process is considered to be an effective means for improving an S/N ratio relative to thermal noise. This is also considered to be effective against random noise interfering with an inspecting apparatus such as electric noise derived from a motor or an welding equipment.

Further, at the time of inspecting flaws, a certain sequence whose autocorrelation function $\rho_{aa}(k)$ has a sharp peak at $k = 0$ and becomes sufficiently small in other range $(0 < k < n)$ is required.

An absolute maximum value $|\rho|_{max}$ in the range other than the peak (i.e. referred to as a range sidelobes) for evaluating an autocorrelation degree of a binary sequence is expressed by the equation (4) as below:

$$|\rho|_{max} = \max\{|\rho_{aa}(k)|\} \quad (4)$$

In this connection, a finite binary sequence satisfying $$|\rho|_{max} = 1/n$$

is specifically referred to as a Barker sequence for distinction.

FIG. 3(a) shows a signal of binary sequence expressed by the following equation (5) wherein $n = 7$:

$$\{a_j\} = + + + - - + - \quad (5)$$

FIG. 3(b) shows an autocorrelation function calculated based on the equation (3) wherein $-n \leq k < n$. It is noted that the maximum value is recorded at $k = 0$ and, at the other portions, it is $1/n$ as the maximum (in this instance 1/7). FIGS. 4 show a complementary sequence which is one of finite binary sequences having a sharp correlation function.

From the equation (3), it is clear that there is no finite length binary sequence whose autocorrelation function becomes zero at all the points other than at the point $k = 0$.

However, there may be a case wherein the sum of respective autocorrelation functions $\rho_{aa}(i)$ and $\rho_{bb}(k)$ of two binary sequences $\{a_j\}$ and $\{b_j\}$ each having a length of n, i.e.

$$\rho(k) = \rho_{aa}(k) + \rho_{bb}(k) \quad (6)$$

becomes zero at all the points other than at the point $k = 0$.

These two sequences $\{a_j\}$ and $\{b_j\}$ are referred to as a complementary sequence.

FIG. 4(a) shows an example of a complementary sequence wherein $n = 4$ and represents a signal of a binary sequence expressed by the equation (7):

$$\{a_j\} = + + + -$$
$$\{b_j\} = + - + + \quad (7)$$

FIG. 4(b) shows autocorrelation functions of $\{a_j\}$ and $\{b_j\}$ in the range $-n \leq k < n$ and calculated based on the equation (3).

FIG. 4(c) indicates the sum $\rho(k)$ of the respective autocorrelation functions calculated based on the equation (6). As seen from this drawing, it is theoretically possible to make levels of range sidelobes zero.

FIG. 5 shows an example detailedly discussed on pages 888–891 of "High-Speed Digital Golay Code Flaw Detection System, IEE 1981 Ultrasonic Symposium Proceeding", by B. B. Lee and E. S. Furgason (hereinafter referred to as Reference A) wherein 1 designates a probe, 2 a transmitter, 5 a code generating source, 10 an analog correlator, 11 a display, 12a and 12b bipolar converters, 13 a selector, 14 a digital delay line, 15 a system controller, 16 a water bath and 17 a target.

FIGS. 6 are drawings for explaining the operation of FIG. 5. FIGS. 6(a), 6(b), 6(c) and 6(d) indicate a synchronizing signal, a code sequence, a selection signal and an output of the bipolar converter 12, respectively.

With the synchronizing signal of FIG. 6(a) from the system controller 15, the code generating source 5 generates a binary code sequence such as shown in FIG. 6(b). The code sequence generated at the code generating source 5 is inputted into the bipolar converter 12a connected to the transmitter 2 through the selector 13 as well as into the digital delay line 14. The code sequence inputted into the bipolar converter 12a connected to the transmitter 2 is given an amplitude of $+/-$ depending on its code at the bipolar converter and, thence, the output of FIG. 6(d) is inputted into the transmitter 2 and applied, as a transmission pulse with being amplified, to the probe 1. An ultrasonic signal radiated from the probe 1 is reflected at the target 17 within the water bath 16, fed back as a receiving signal to the probe 1 and, thence, directed to the analog correlator 10.

The code sequence of FIG. 6(b) inputted into the digital delay line 14 is delayed by a time (t') designated by the system controller 15, inputted into the other bipolar converter 12b as a reference code sequence [FIG. 4(f)] and directed, as a signal for a correlation processing with an amplitude of $+/-$ being given at the bipolar converter 12b depending on the input code, to the analog correlator 10.

Within the analog correlator 10, the left side operation of the equation (3) is performed with using a multiplier 10a and an integrator 10b wherein the delay time "t'" of the reference signal code [FIG. 4(f)] corresponds to "k" in the equation (3). Therefore, an inspected wave form after the correlation process can be displayed in the display by varying the delay time t' at each cycle of repetitive transmission in the system controller 15.

With employment of the correlation process as above, an S/N ratio has been improved.

In case where the process of the complementary sequence explained regarding FIG. 4 is carried out with using the above apparatus, it is not possible to use the apparatus shown in FIG. 3 and addition of some memory means and some means for summing the operational results of correlation operation on two sequences would be required.

Incidentally, in a conventional ultrasonic inspecting apparatus performing a correlation process with using finite length binary sequence, transmission signals are given at a level of $+/-$ to a probe. FIG. 7 shows frequency characteristics of a probe, etc. used for a flaw inspecting apparatus and "a" of FIG. 7 indicates a frequency response of a probe 1, "b" a frequency characteristic of a transmission signal wave form used in a conventional apparatus and "c" a frequency responding characteristic of a specimen in which, for example, attenuation is relatively large. There has been a problem in that the transmission signal applied to the probe 1 possesses, due to its feature of a pulse signal, its energy in a relatively low frequency range and the energy in the low frequency range has not been effectively utilized by the probe 1 due to its frequency characteristics.

In addition to the above, it is seen that a frequency characteristics of an ultrasonic beam radiated into a body of specimen depends on a frequency characteristics of a probe because a frequency range of a transmission signal is wide. This matter indicates that manufacturing tolerances of a probe affect a flaw detection frequency whereby there has been a problem in that results of flaw detection would not be constant if the probe is switched to the other. Further, FIG. 7 indicates that a certain part of a frequency range wherein a probe is effectively used is cut off depending on an attenuation characteristic of a specimen. Therefore, there has been another problem in that noise may remain at a certain level in a case where attenuation in a specimen is high and an S/N ratio likely becomes worse even an S/N ratio is improved by a conventional correlation process whereby enlarging of an amplitude in transmission signal has been required.

Also, there has been a further problem in that a component of code sequence may remain even if a correlation process is carried out and it cannot be reduced because interfering echo is due to an internal construction of a specimen or due to the fact that it is derived from reverberation echo in a high speed inspection.

There are further references in the names of the same authors as those of Reference A with respect to a conventional ultrasonic non-destructive inspecting apparatus as follows.

"An Evaluation of Ultrasound NDE Correlation Flaw Detection Systems", IEEE Transactions on Sonics and Ultrasonics, Vol. SU-29, No. 6, Nov., 1982, pp 359-369 (Reference B); and "High-Speed Digital Golay Code Flaw Detection Systems", Ultrasonics, July, 1983, pp. 153-161 (Reference C).

An operation of a conventional example shown in FIG. 5 is touched upon again from further aspect referring to FIGS. 8 and 9. FIG. 8 shows a wave form of a transmission signal in a conventional ultrasonic non-destructive inspecting apparatus, for example shown in Reference B and FIG. 9 shows a wave form of a compressed pulse in a conventional apparatus shown in Reference B. In FIG. 8, abscissa is expressed by unit of bits and, thus, it may be regarded as a time if a unit time corresponding to a unit of bit is used. In Reference B, a unit time corresponding to a unit bit is represented by a symbol $\delta$. Therefore, the pulse width of the transmission signal is $63 \times \delta$.

This transmission signal is one having a frequency band as a base band wherein an amplitude thereof is coded by a special sequence. As to the coding process, it will be discussed later but the sequence employed therein is explained.

A finite length sequence having a length of 63 bits is used and it is produced by cutting one cycle of M-sequence (maximal length sequence) having a cycle length of 63 bits.

As to M-sequence, it is detailedly explained, for example, on pages 474-499 of "Coding Theory" coauthored by Hiroshi Miyagawa, Yoshihiro Iwataru and Hideki Iwai, published from Shokodo, Jun. 29, 1989 (Reference D) which reference was touched upon earlier. M-sequence is an infinite length cyclic sequence and its component constituting the sequence is a binary sequence comprising two elements. For the two elements, codes "+" and "−", or numerical values of "+1" and "−1" or "1" and "0" are assigned depending on the case. In the example shown in FIG. 8, a finite length sequence is produced by taking out one cycle from M-sequence having an infinite length and a cycle length of 63 bits.

Next, explanation is given with respect to an amplitude coding process using this finite length sequence. An amplitude is modulated to ±1 with their relative values per each unit time δ according to appearing order of the sequence elements "±" by assigning an amplitude "+1" and an amplitude "−1" to an element "+1" and an element "−1" constituting the finite sequence, respectively. These signals are referred to as coded signals.

In FIG. 9, abscissa is expressed, similar to FIG. 8 by a unit of bit and it will be regarded as a time if a unit time δ is assigned to a unit bit.

This compressed pulse is an example wherein a transmission signal coded in its amplitude by a finite length sequence of 64 bits. This sequence is produced by adding 1 bit to the finite length sequence of 63 bits used for producing the transmission signal shown in FIG. 8. Therefore, the pulse width of this transmission signal is 64δ. The pulse width of echo is almost equal to the above length.

As shown in FIG. 9, the majority of the compressed pulse energy is concentrated to the central time range (several bits × δ) in the drawing. The center signal portion having a large amplitude is referred to as a main lobe of a compressed pulse. The pulse width of the main lobe is small. This means that the energy of echo is substantially concentrated to a point on the time axis. Portions of signals having small amplitudes at the opposite sides are referred to as range sidelobes of a compressed pulse.

A transmission signal such as shown in FIG. 8 is produced from the signal source 5 and digital delay line 14 through the bipolar converter 12a and the transmitter 2. The ultrasonic probe 1 is driven by this signal.

The ultrasonic wave radiated from the ultrasonic probe 1 is reflected at the target 17 and received by the probe 1. The echo received by the probe 1 is transmitted to the multiplier 10a of the analog correlator 10.

The pulse width of the above echo is almost equivalent, in length, to that of the transmission signal. That is, energy of the echo is distributed almost uniformly over the time (approximately 63 × δ), that is the pulse width of the transmission signal.

On the other hand, the same signal as the above transmission signal is transmitted to the multiplier 10a of the analog correlator 10.

The analog correlator 10 performs a correlation operation between the echo and the transmission signal. With this correlation operation, the echo energy distributed approximately uniform over the time on the time axis equivalent in length to that of the transmission signal is compressed substantially to a single point on the time axis. The pulse obtained by the above operation is referred to a compressed pulse.

The compressed pulse obtained from the analog correlator 10 is transmitted to the display 11 and displayed as a final result.

The distance resolution of the conventional ultrasonic non-destructive inspecting apparatus explained above is dependent on a main lobe pulse width of a compressed pulse (simply referred to as a pulse width of a compressed pulse). While the pulse width of the transmission signal is wide, the pulse width of the compressed pulse is, as touched upon above, narrow. Therefore, in the conventional apparatus, the resolving power is obtained which is similar to that in the case of an ultrasonic non-destructive inspecting apparatus employing a pulse-echo method with the use of a transmission signal originally having a narrow pulse width.

On the other hand, an S/N ratio becomes higher as a mean energy of a transmission signal becomes larger. The mean energy of a transmission signal becomes larger as a pulse width of the transmission signal becomes wider. Therefore, in a conventional non-destructive inspecting apparatus, a higher S/N ratio can be obtained compared to that obtained by a pulse-echo method using a transmission signal originally having a narrow pulse width.

As explained above, a good resolution and a high S/N ratio can be obtained in a conventional ultrasonic non-destructive inspecting apparatus.

However, in a conventional non-destructive inspecting apparatus, there is a problem in that, if levels of the range sidelobes are high, a position of a reflecting body (such as a flaw, etc.) may be misrecognized as in a position corresponding to a time when a range sidelobe of a compressed pulse appears.

To avoid such a problem as above, it is necessary to lower levels of the range sidelobes of the compressed pulse. To such end, it is required to lower levels of range sidelobes in an autocorrelation function of a sequence used for coding a transmission signal.

In other words, as a sequence to be used for coding a transmission signal, it is necessary to use a sequence in which a level of an autocorrelation function range sidelobes is low.

Hereinafter, explanation is given referring to FIG. 10 with respect to range sidelobes of a compressed pulse and range sidelobes of an autocorrelation function of a sequence. As to definition regarding an autocorrelation function of a sequence there is a detailed description in Reference D.

FIG. 10 shows a wave form indicating an autocorrelation function of a finite length sequence used for coding the transmission signal shown in FIG. 8.

M-sequence is, as described on pages 479–483 of Reference D, the sequence wherein an autocorrelation function thereof possesses a sharp peak referred to as a main lobe and range sidelobes having low levels. However, as noted on page 489 of Reference D, if a finite length sequence is produced by picking up one cycle of a cyclic sequence having a low range sidelobe level, a range sidelobe level of an autocorrelation function of the finite length sequence produced as above is not necessarily low as shown in FIG. 10 even the range sidelobe level of an original cyclic sequence autocorrelation function is low.

It is described on pages 479–480 of Reference D that a range sidelobe level of M-sequence autocorrelation function is $1/n$ wherein a cycle length is expressed by "n" and a peak value of a main lobe is given as "1" by normalization. therefore, in the case where a cyclic length is 63 bits, a range sidelobe level is $1/63 = 0.0159$. However, it is noted by referring to FIG. 10 that, in the autocorrelation function of finite length sequence used for coding the transmission signal of FIG. 8, a range sidelobe level is at least more than 0.1 and larger, by one order, than the level of M-sequence autocorrelation function range sidelobes.

Thus, there is a problem in that, if a sequence produced as a finite length by cutting from M-sequence is used for coding a transmission signal, levels of a compressed pulse range sidelobes becomes high. The compressed pulse shown in FIG. 9 is an example that a range sidelobe level is high. Also, it is disclosed in Reference B that a trial was made with using a sequence cut off by 63 bits from M-sequence. In this case, it is disclosed that, while a shape (pattern) of range sidelobes was different from that of FIG. 9, the difference was not beyond 3 dB compared to the case of FIG. 9. In these examples, it is noted that, if a sequence having a low level in its autocorrelation function range sidelobes is not used as the sequence for coding a transmission signal, lowering a compressed pulse range sidelobe level is not possible.

From the foregoing, it is clear that it is considered to be best if a sequence is available which has completely no range sidelobe in its autocorrelation function. However, as disclosed in Reference D, there is no finite length binary sequence with zero range sidelobe.

However, as described in the same Reference D, there may be a case wherein, if respective autocorrelation functions of two finite length binary sequences each having the same length are summed, a range sidelobe will completely disappear after the summing operation. Two sequences constituting a pair having such a feature as above is referred to as a complementary sequence. As to the complementary sequence, it is disclosed in detail on pages 82-87 of "Complementary Series, IRE Transactions on Information Theory, vol. IT-7, April, 1961 by M. J. E. Golay. This complementary sequence is referred to either as Golay Complementary Sequence or simply Golay Code. Now, an autocorrelation function of a complementary sequence is explained referring to FIGS. 11(a), 11(b) and 12.

FIGS. 11(a) and 11(b) show wave forms of autocorrelation functions of 1st and 2nd sequences constituting, for example, a complementary sequence shown in Reference D. FIG. 12 shows a wave form indicating the result of the summing operation of autocorrelation functions of the 1st and 2nd sequences.

As seen from FIGS. 11(a) and 11(b), a high level is observed in the range sidelobes of both the autocorrelation functions. An autocorrelation function (hereinafter referred to as a composite autocorrelation function) obtained by a summing operation has, at the center as shown in FIG. 12, only a sharp peak corresponding to a main lobe and completely no range sidelobe.

In References A and C, an ultrasonic non-destructive inspecting apparatus is disclosed. Two sequences constituting a complementary sequence are alternately and repeatedly used and this matter is explained referring to FIGS. 13(a), 13(b) and 14.

FIGS. 13(a), 13(b) and 14 illustrate wave forms showing computer simulation results of 1st and 2nd compressed pulses and composite pulse disclosed in Reference C.

Two sequences constituting a complementary sequence are, hereinafter, referred to as 1st and 2nd sequences. Also, two transmission signals produced in a manner similar to that in the case of FIG. 8 are referred to as 1st and 2nd transmission signals, respectively. Two echoes obtained when the ultrasonic probe is driven by the 1st and 2nd transmission signals are referred to as 1st and 2nd echoes, respectively. Further, two compressed pulses obtained by a correlation process similar to FIG. 9 with the use of 1st the 2nd transmission signals are referred to as 1st and 2nd compressed pulses, respectively.

First and second transmission signals are alternately repeated with a certain cycle period. In the period when the ultrasonic probe 1 is driven by the 1st transmission signal, the 1st echo is obtained and this 1st echo is correlation processed within the same period with using the 1st transmission signal so that the 1st compressed pulse is obtained. Similarly, the 2nd echo is obtained in the period when the ultrasonic probe 1 is driven by the 2nd transmission signal and this 2nd echo is correlation processed within the same period with using the 2nd transmission signal so that the 2nd compressed pulse is obtained. Further, by making an integration time of the analog correlator 10 longer than the twice of the repetition period of transmission signals, an operation for summing the 1st and 2nd compressed pulses is carried out.

The result of summing the 1st and 2nd compressed pulses is referred to as a composite compressed pulse which is displayed on the display 11.

As shown in FIGS. 13(a) and 13(b), the levels of range sidelobes are high in both the 1st and 2nd compressed pulses. However, as shown in FIG. 14, in the composite compressed pulse only a main lobe appears at the center and there is completely no range sidelobe.

As explained above, the conventional ultrasonic non-destructive inspecting apparatus possesses a superior feature in that there is no range sidelobe.

However, a complementary sequence having a feature that there is no range sidelobe in its composite autocorrelation function is not always existing for all of natural numbers "n" representing the length of the sequence. A complementary sequence is existing for limited lengths. For example, below 50 in respect of the length, it exists, as disclosed in Reference D, with respect to the cases wherein N=2, 4, 8, 10, 16, 20, 26, 32 and 40. However, it is not clear in the cases wherein n=34, 36 or 50.

Accordingly, there has been a problem in the conventional ultrasonic non-destructive inspecting apparatus in that levels of range sidelobes are high and, in the case where a complementary sequence is used which can make the level of range sidelobes zero, a sequence length "n" is available only for limited numbers.

In the foregoing, discussion has been made rather at length with respect to prior art and several problems were touched upon. Those problems may be classified as follows.

I—Insufficient Accuracy in Detecting a Flaw and Insufficient Utilization of Transmission Energy;
II—Interferences; and
III—Limitation in Selecting Length of Complementary Sequence.

SUMMARY OF THE INVENTION

Accordingly, it has been desired to have a detecting apparatus for performing a non-destructive inspection which is free from the drawbacks above and, thus, it is an object of the present invention to provide a non-destructive detecting apparatus utilizing waves such as ultrasonic waves, electric waves or micro-waves which can overcome the drawbacks of prior art.

Further, it is an object of the present invention to provide a means for identifying kinds of flaws in the non-destructive detecting apparatus.

A non-destructive detecting apparatus is constructed, in accordance with the present invention, to comprise:
(i) a first transmission signal generator for generating a first transmission signal which has a wave form comprising smoothly curved portions;
(ii) a second transmission signal generator for generating a second transmission signal which has a wave form comprising smoothly curved portions;

(iii) a first transmitting means for transmitting waves to an object by said first transmission signal;

(iv) a second transmitting means for transmitting waves to said object by said second transmission signal;

(v) a first receiving means for receiving a first echo corresponding to said first transmission signal;

(vi) a second receiving means for receiving a second echo corresponding to said second transmission signal;

(vii) a first correlator for performing a first correlation operation with respect to said first echo;

(viii) a second correlator for performing a second correlation operation with respect to said second echo; and (ix) a processor for processing results of said first and second correlation operations, whereby a signal which has substantially zero range sidelobes is obtained.

According to further aspect of the present invention, another embodiment comprises:

(a) a transmission signal generating means for generating a plurality of more than three transmission signals;

(b) a transmitting means for transmitting waves to an object by said transmission signals;

(c) a receiving means for receiving echoes corresponding to said respective transmission signals;

(d) a correlation operation means for performing correlation operations with respect to said respective echoes; and (e) a processor for processing results of said correlation operations, whereby a signal which has substantially zero range sidelobe is obtained.

In the detecting apparatus according to the present invention, a wave form having a frequency component $f_0$ is generated with respect to either positive code or a negative code of a binary code sequence having a sharp autocorrelation function and the phase thereof is altered by 180° in correspondence to the positive or negative code.

With the above arrangement, almost all the energy of the transmission signal can be assigned to a frequency band passing through the probe so that the utilization of the transmission energy is improved.

In some of the embodiments, the signal, which has already passed through the signal transmitting passages such as the probe and specimen, etc. having different frequency characteristics, is used as a reference signal at the time of performing a correlation operation of a received signal so that a particular wave form may be emphasized.

Also, in some embodiments, a plurality of correlation operation portions are provided and the above reference signal added with frequency characteristics of several kinds of flaws are used as reference signals for the respective operation portions.

The present invention will be further explained referring to the accompanying drawings following a brief explanation of drawings summarized below.

BRIEF DESCRIPTION OF THE DRAWINGS

FIG. 14 shows a composite compressed pulse in a conventional ultrasonic non-destructive inspecting apparatus;

FIGS. 17(a) and (b) show a result of a correlation operation in the first embodiment of the present invention;

FIGS. 28(a) and (b) show a result of a correlation operation in the second embodiment of the present invention;

FIGS. 37 are drawings for explaining FIG. 38;

FIGS. 38 through 43 show a fifth embodiment according to the present invention;

FIG. 44 is a block diagram showing a sixth embodiment according to the present invention;

FIG. 50 shows a wave form of impulse response of an ultrasonic probe in the sixth embodiment of the present invention;

FIGS. 56(a) and (b) show drawings for explaining a multiple complementary sequence comprising four and six sequences;

DETAILED DESCRIPTION OF THE PREFERRED EMBODIMENTS

It is to be noted that the embodiments explained hereinafter with respect to ultrasonic waves are merely for the convenience and they are not limited to use ultrasonic waves but also applicable to use other transmission waves such as micro-waves or electric waves.

A construction of a first embodiment of the present invention is explained with reference to FIG. 15.

Figure 15:
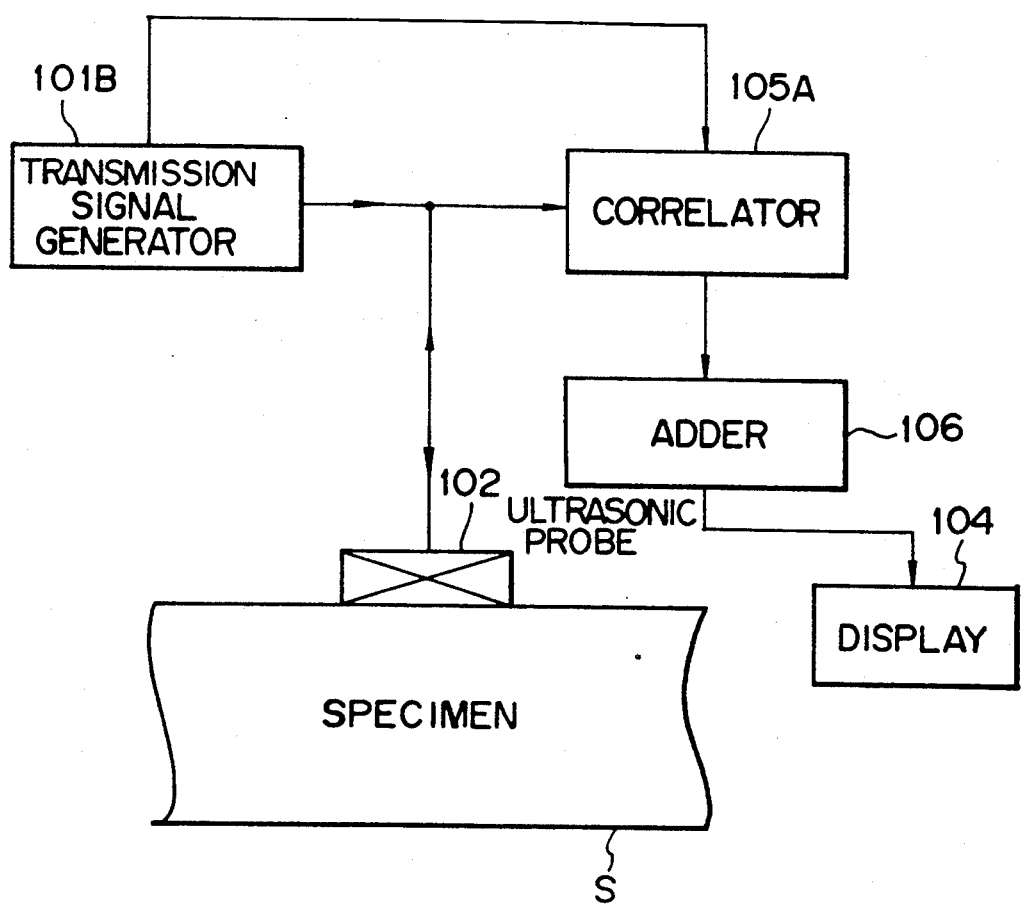
FIG. 15 shows a first embodiment according to the present invention in a block diagram.

FIG. 15 is a block diagram showing the first embodiment and an ultrasonic probe 102 and a display 104 are the same as those of prior art.

In FIG. 15, the first embodiment comprises the same components as those of prior art and others, namely, a transmission signal generator 101B, a correlator 105A coupled to the transmission signal generator 101B and the ultrasonic probe 102, and an adder 106 having a memory function and connected to the correlator 105A.

Incidentally, the ultrasonic probe 102 is connected to the transmission signal generator 101B and the display 104 is connected to the adder 106.

Next, an operation of the first embodiment is explained referring to FIGS. 16, 17, 18 and 19.

The transmission signal generator 101B generates transmission signals $S_a^*(t)$ and $S_b^*(t)$ and transmits them to the ultrasonic probe 102.

Figure 16A:
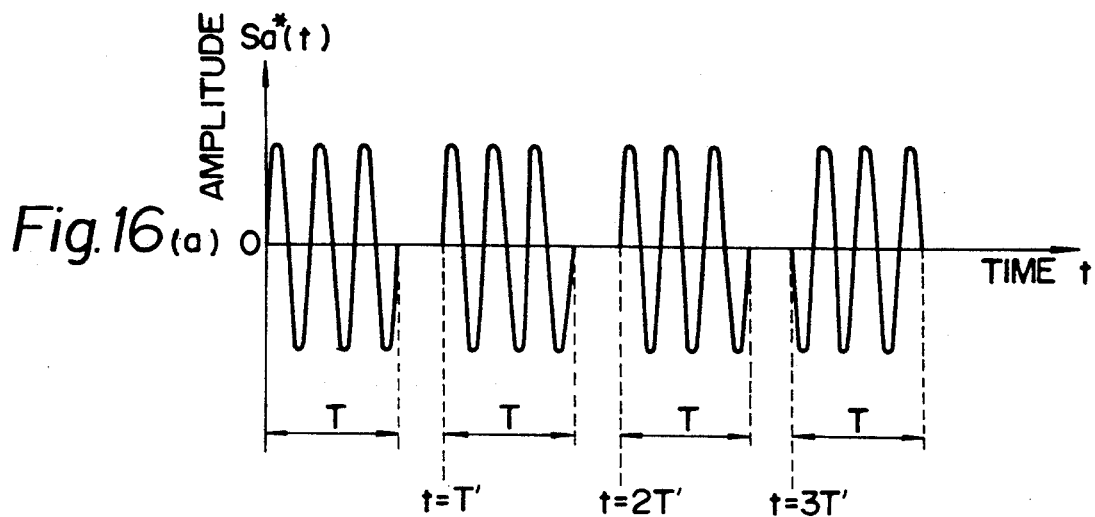
FIGS. 16(a) and (b) show a wave form of a transmission signal in the first embodiment of the present invention.
Figure 16B:
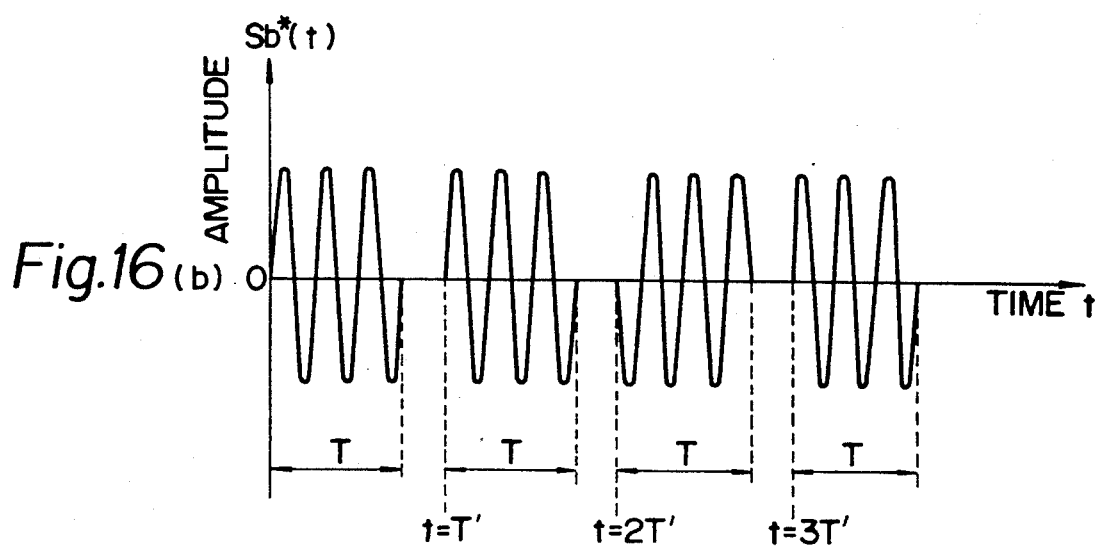

As shown in FIGS. 16(a) and (b), the transmission signal $S_a^*(t)$ employs $(+, +, +, -)$ as a 1st sequence A and the transmission signal $S_b^*(t)$ employs $(+, +, -, +)$ as a 2nd sequence B, the 1st and 2nd sequences A and B constituting a complementary sequence. For the positive sign "+", $\sin 2\pi f_0 t$ ($0 \leq t \leq T$) is assigned and for the negative sign "−", $-\sin 2\pi f_0 t$ ($0 \leq t \leq T$) is assigned and the above sinusoidal wave portions are arranged on the time axis in the appearing order of the signs, wherein t is a time variable, T a fixed time and $f_0$ a fixed frequency.

The ultrasonic probe 102 is driven by the above transmission signal $S_a^*$, radiates ultrasonic waves towards a specimen S, receives a reflection echo $G_a^*(t)$ reflected at some reflecting portion inside the specimen and transmits it to the correlator 105A The same signal as the above transmission signal is also transmitted to the correlator 105A.

The correlator 105A performs a correlation operation between the reflection echo $G_a^*(t)$ and the transmission signal $S_a^*(t)$. The result $\rho_a^*$ of the correlation operation is expressed by the following equation:

$$\rho_a^*(t) = \int G_a^*(t') S_a^*(t'-t) dt' \quad \text{[integrating range:} -\infty \sim \infty] \tag{101}$$

Similarly, in the next time phase, the ultrasonic probe 102 is driven by the above transmission signal $S_b^*(t)$ and the correlator 105A performs a correlation operation between the reflection echo $G_b^*(t)$ and the transmission signal $S_b^*(t)$ and its result $\rho_b^*(t)$ is expressed by $$\rho_b^*(t) = \int G_b^*(t') S_b^*(t')(t'-t) dt' \quad \text{[integrating range:} -\infty \sim \infty] \tag{102}$$

The adder 106 sums the results of correlation operations of equations (101) and (102) and transmits it to the display 104 which displays $$\rho_a^*(t) + \rho_b^*(t).$$

Incidentally, the adder 106 stores $\rho_a^*(t)$ in itself until $\rho_b^*(t)$ is transmitted.

An operational principle of the first embodiment according to the present invention is explained hereunder.

If the 1st sequence A and the 2nd sequence B are in a complementary relationship, the transmission signals $S_a*(t)$ and $S_b*(t)$ are also in a complementary relationship whereby range sidelobe levels become theoretically zero.

Autocorrelation functions of the transmission signals $S_a*(t)$ and $S_b*(t)$ are expressed, in the following description, by $\rho_a*(\tau)$ and $\rho_b*(\tau)$, respectively. These $\rho_a*(\tau)$ and $\rho_b*(\tau)$ are defined as follows:

$$\rho_a*(\tau) = \int S_a*(t) S_a*(t-\tau) dt \text{ [integrating range:} -\infty \sim \infty] \quad (103)$$

$$\rho_b*(\tau) = \int S_b*(t) S_b*(t-\tau) dt \text{ [integrating range:} -\infty \sim \infty] \quad (104)$$

Figure 18:
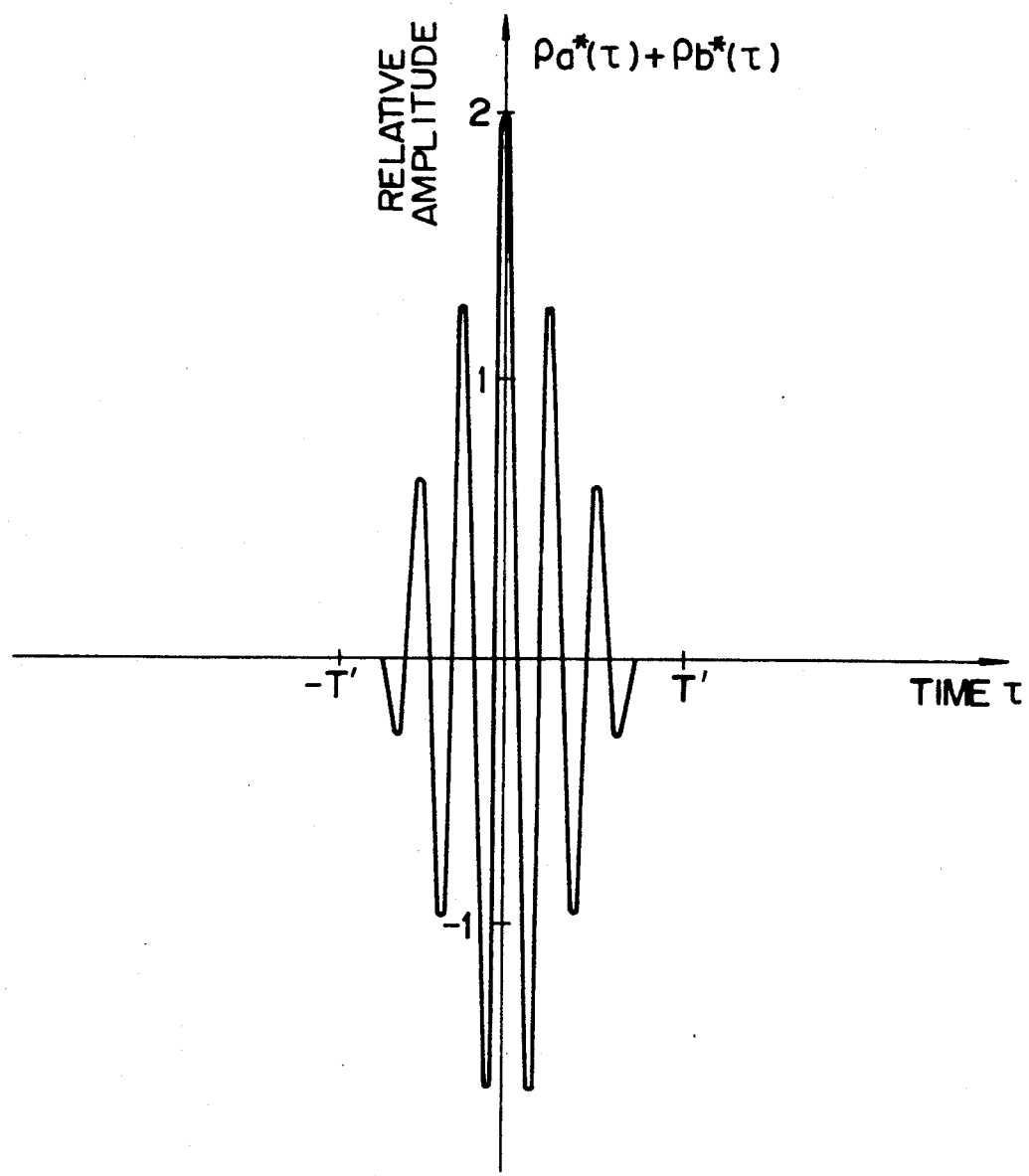
FIG. 18 shows a summing result of correlation operations in the first embodiment of the present invention.

As shown in FIGS. 17(a) and (b), comparison between the autocorrelation functions $\rho_a*(\tau)$ and $\rho_b*(\tau)$ reveals that their amplitudes are the same in respect of their primary lobes as well as they range sidelobes while their phases are the same in respect of their primary lobes but are opposite in respect of their range sidelobes. Accordingly, sidelobe level become zero as shown in FIG. 18, when the autocorrelation functions $\rho_a*(\tau)$ and $\rho_b*(\tau)$ are summed. In other words, if the 1st sequence A and the 2nd sequence B are in a complementary relationship, the transmission signals $S_a*(t)$ and $S_b*(t)$ are in the same relationship.

In FIGS. 16(a) and (b), there is shown a case wherein an interval T' that is an arranging interval of $\sin 2\pi f_0 t$ and $-\sin 2\pi f_0 t$ is larger than an interval T. However, the relationship explained above is also applicable to a case wherein an arrangement interval T' equals to T. Also there is shown a case wherein a cycle number of $\sin 2\pi f_0 t$ and $-\sin 2\pi f_0 t$ is 3 ($= f_0 T$) but the relationship explained above holds regardless of a cycle number.

Now consideration is given to a case where ultrasonic waves are used in a non-destructive inspection.

Let's express a round trip time of a ultrasonic wave between the ultrasonic probe 102 and a reflecting portion within the specimen S by $t_0$. When the probe 102 is driven by the signal $S_a*(t)$, the reflection echo is approximately expressed as $S_a*(t-t_0)$. If a correlation operation is carried out between the reflection echo $S_a*(t-t_0)$ and the transmission signal $S_a*(t)$, the right hand side of the following equation is obtained.

$$\int S_a*(t-t_0) S_a*(t-\tau) dt = \rho_a*(\tau - t_0) \text{ [integrating range:} -\infty \sim \infty] \quad (105)$$

Similarly, the reflection echo is approximately expressed as $S_b*(t-t_0)$ when, at the next time phase, the ultrasonic probe 102 is driven by the transmission signal $S_b*(t)$. If a correlation operation is carried out between the reflection echo $S_b*(t-t_0)$ and the transmission signal $S_b*(t)$, the right hand side of the following equation is obtained.

$$\int S_b*(t-t_0) S_b*(t-\tau) dt = \rho_b*(\tau - t_0) \text{ [integrating range:} -\infty \sim \infty] \quad (106)$$

When the results of the above correlation operations are summed, the following is obtained.

$$\rho_a*(\tau - t_0) + \rho_b*(\tau - t_0).$$

This result is the same as a case where the wave form shown in FIG. 18 is shifted by $t_0$ along the time axis. That is, it has a primary lobe at $\tau = t_0$ and zero range sidelobe levels. Therefore, a position of the reflection body can be determined by detecting the time when the primary lobe appears.

Figure 19:
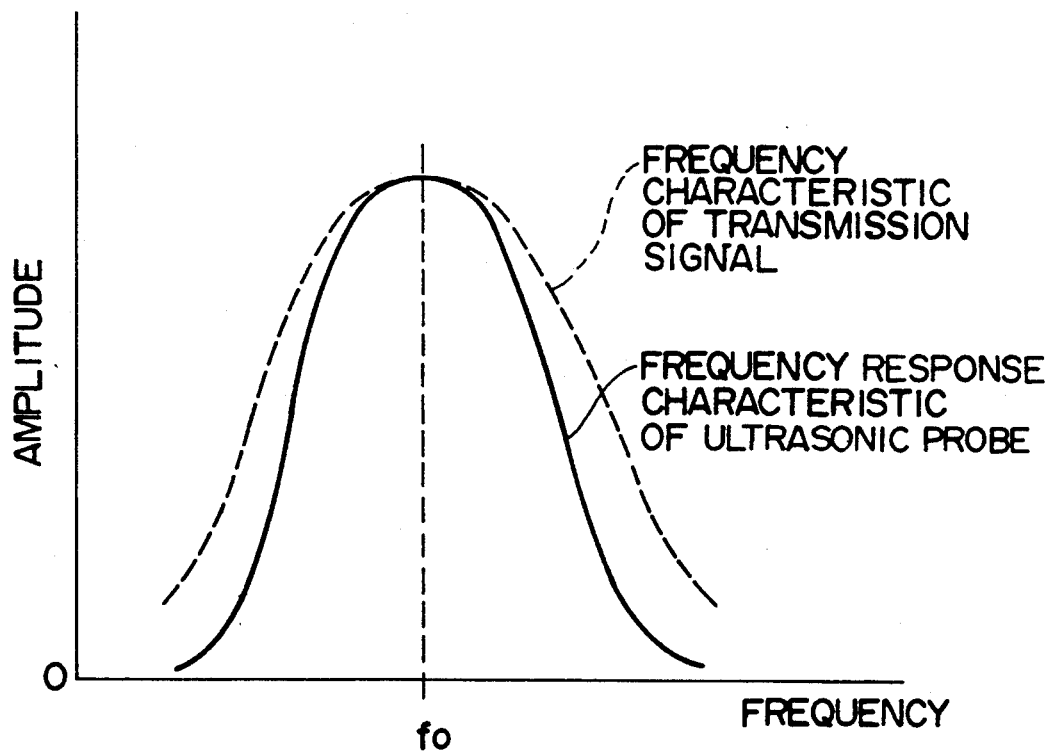
FIG. 19 shows frequency characteristics of a transmission signal and an ultrasonic probe in the first embodiment of the present invention.
Figure 20:
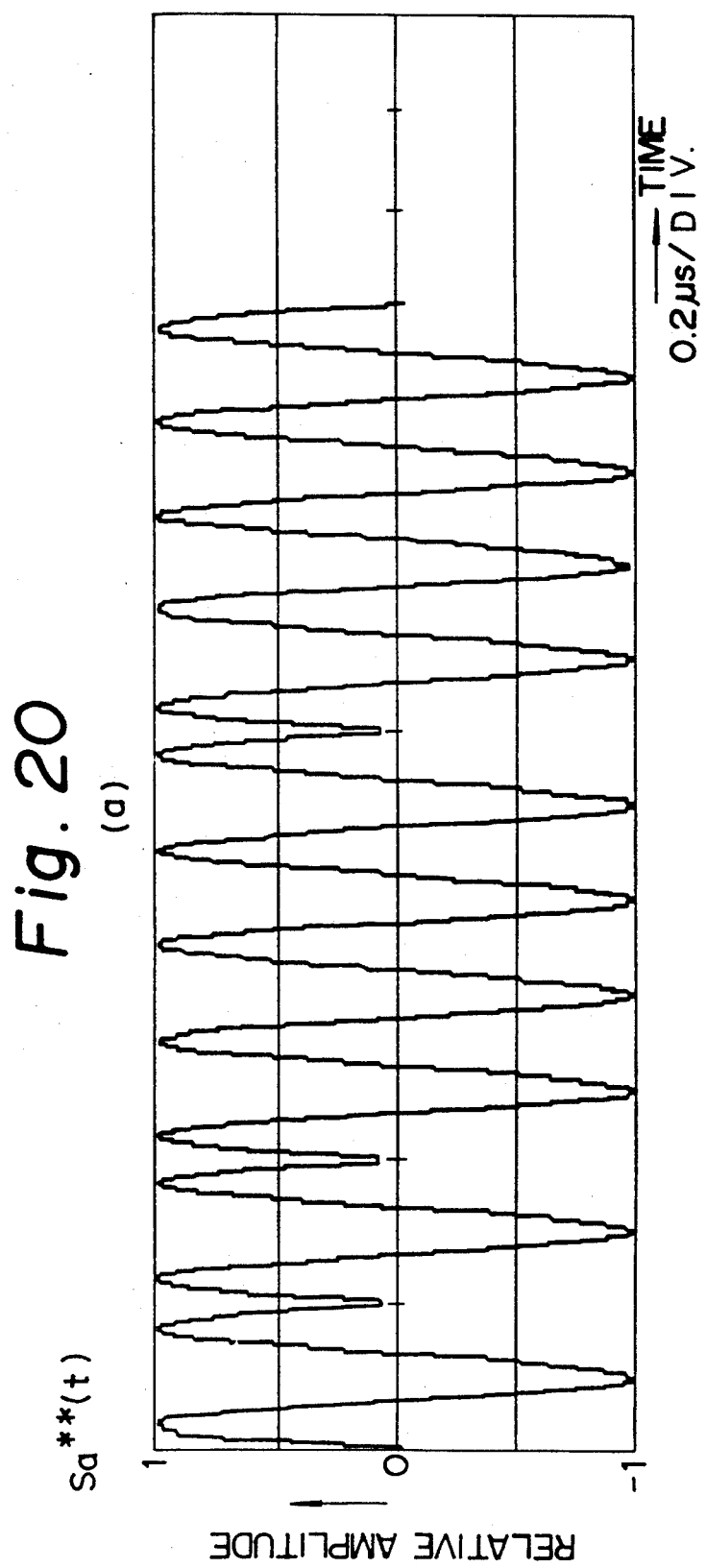
FIGS. 20(a) and (b) show a wave form of another transmission signal in the first embodiment of the present invention.
Figure 20B:
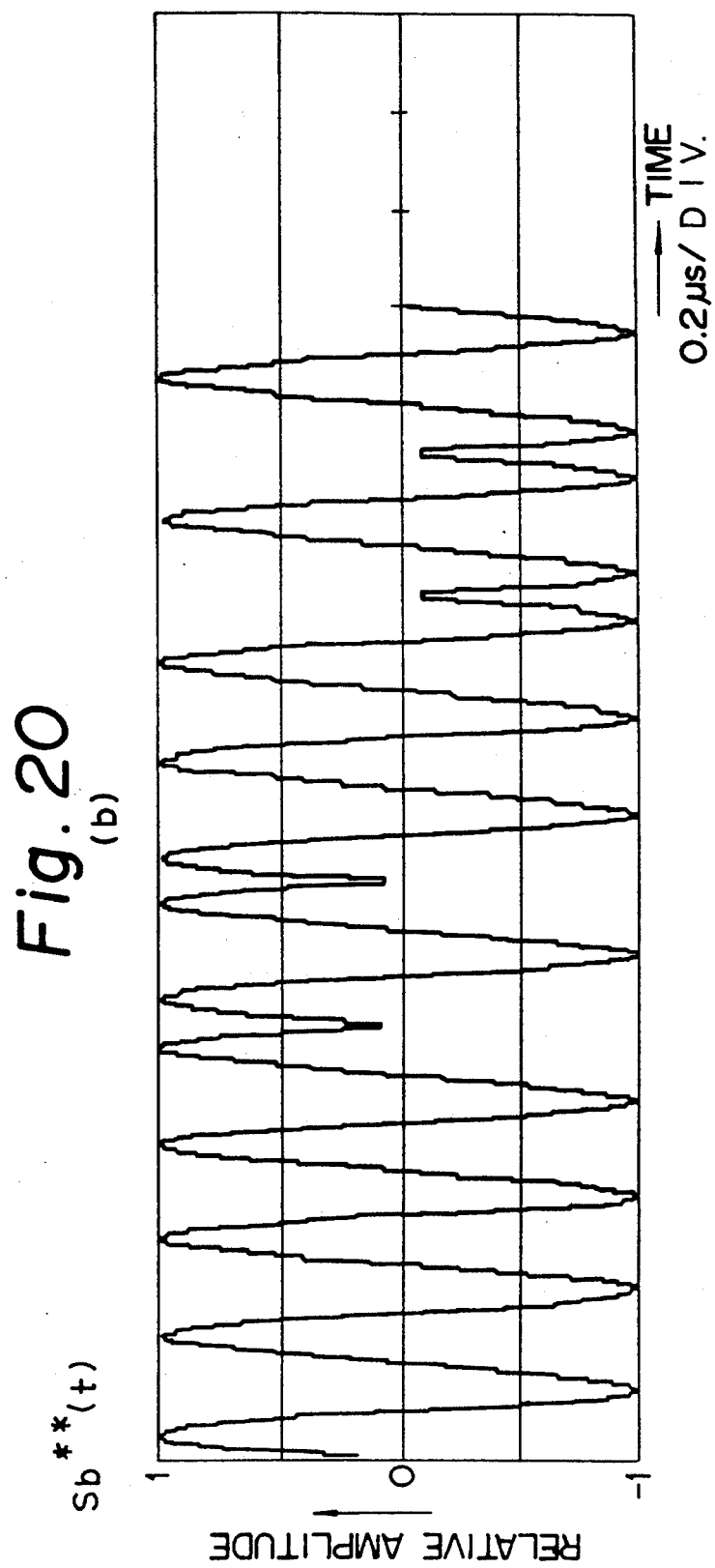

An advantageous effect obtained in the first embodiment according to the present invention is explained hereunder. If the frequency $f_0$ of the transmission signals $S_a*(t)$ and $S_b*(t)$ is set at near the center frequency of the ultrasonic probe 102, the frequency characteristics of the transmission signals $S_a*(t)$ and $S_b*(t)$ and the frequency response characteristic of the ultrasonic probe 102 become as shown in FIG. 19. The transmission signals $S_a*(t)$ and $S_b*(t)$ have substantially no energy in the low frequency region and, so most of the energy passes through the ultrasonic probe 102. Therefore, compared to prior art, efficiency for utilizing energy in the first embodiment is made higher.

Next, in order to evaluate the improvements in the first embodiment with respect to range sidelobes and S/N ratios, the operation under the following conditions is explained referring to FIGS. 20, 21, 22 and 23.

An ultrasonic probe, so-called a broad band probe, having a center frequency of 5 MHz and a relative band width of 60% or more was used as the ultrasonic probe 102 and steel was employed as the specimen S.

As a complementary sequence, the following sequences were employed, each having a length of 8.

$$A = (+, +, +, -, +, +, -, +)$$

$$B = (+, -, +, +, +, -, -, -)$$

As the transmission signals $S_a(t)$ and $S_b(t)$ corresponding to these complementary sequences A and B, respectively, signals shown in FIGS. 20(a) and (b) were employed wherein $f_0 = 5$ MHz, $f_0 T = 1.5$.

An interval T' between the unit wave forms (the sinusoidal wave portions) was set to be equivalent to T.

At first, the ultrasonic probe 102 was driven by the transmission signal $S_a(t)$ and the reflection echo $G_a(t)$ such as shown in FIG. 21(a) was measured.

Similarly, the reflection echo $G_b(t)$ such as shown in FIG. 21(b) was measured by using the transmission signal $S_b(t)$.

The reason why the wave forms of the reflection echoes $G_a*(t)$ and $G_b(t)$ are different from those of the transmission signals $S_a(t)$ and $S_b(t)$ is due to a filtering function of the ultrasonic probe 102 with a finite band width. This filtering function operates doubly since the transmission signals $S_a(t)$ and $S_b(t)$ pass through the ultrasonic probe 102 twice, that is, at the time of transmitting and at the time of receiving.

By performing the correlation operation between the transmission signal $S_a(t)$ and the reflection echo $G_a(t)$, the result shown in FIG. 22(a) was obtained. Similarly, by performing the correlation operation between the transmission signal $S_b(t)$ and the reflection echo $G_b(t)$, the result shown in FIG. 22(b) was obtained.

Figure 23:
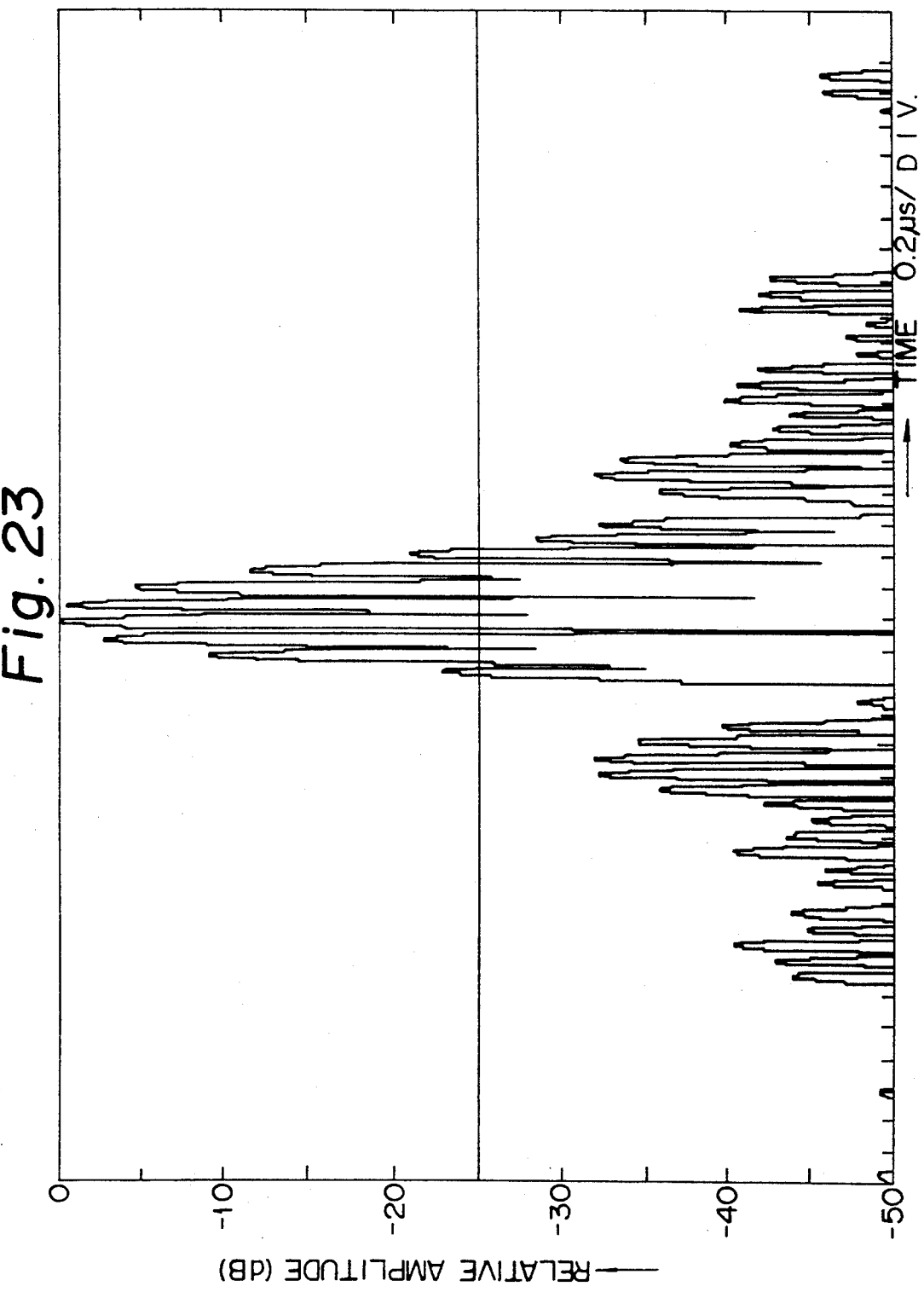
FIG. 23 shows a summing result of another correlation operation in the first embodiment of the present invention.

Then, by summing the above two operation results, the result shown in FIG. 23 was obtained. The levels of range sidelobes are below $-32$dB which is relatively low, and the result also shows that the S/N ratio is higher than 32 dB.

Figure 61:
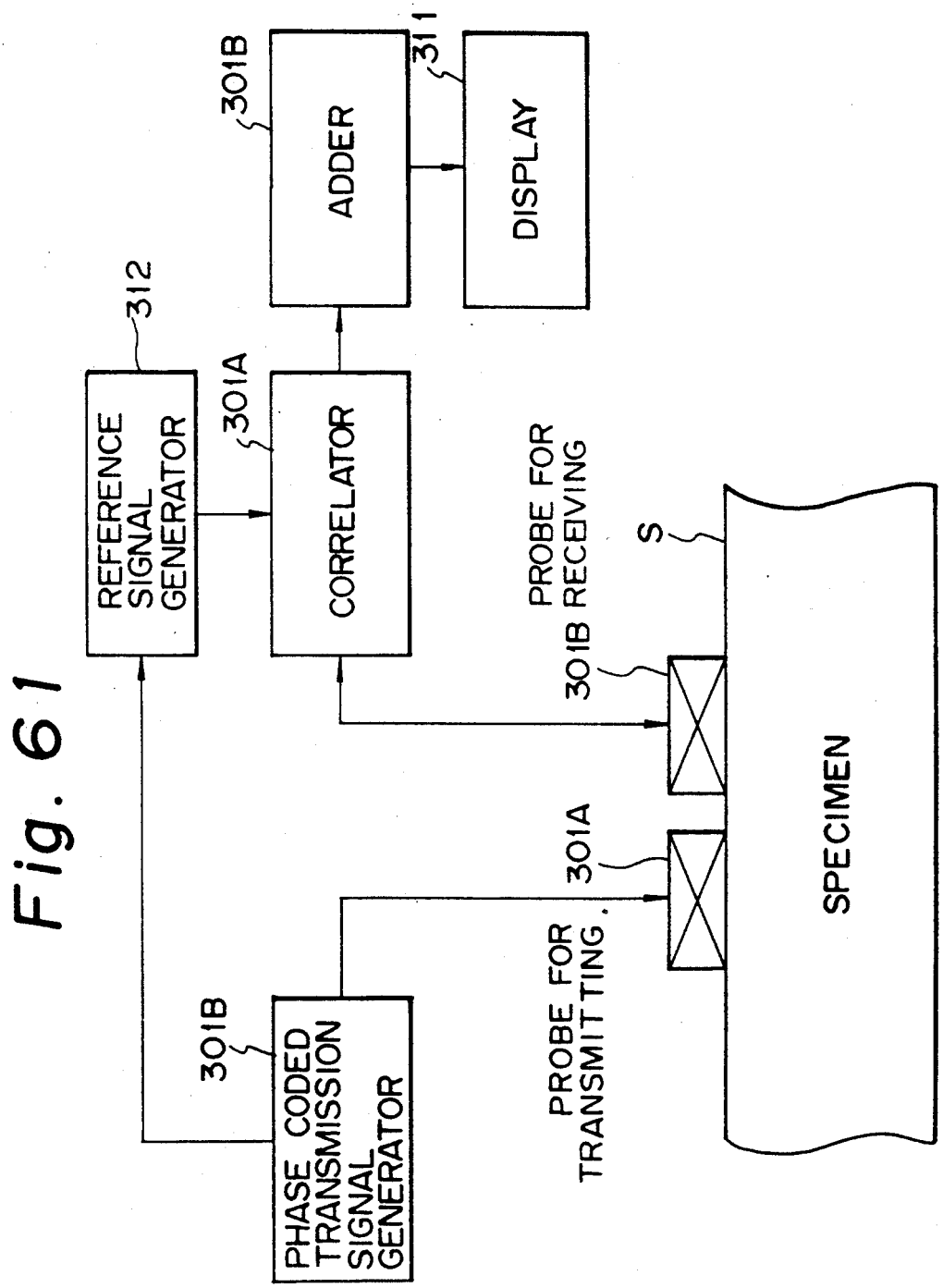
FIG. 61 shows a tenth embodiment according to the present invention.
Figure 62:
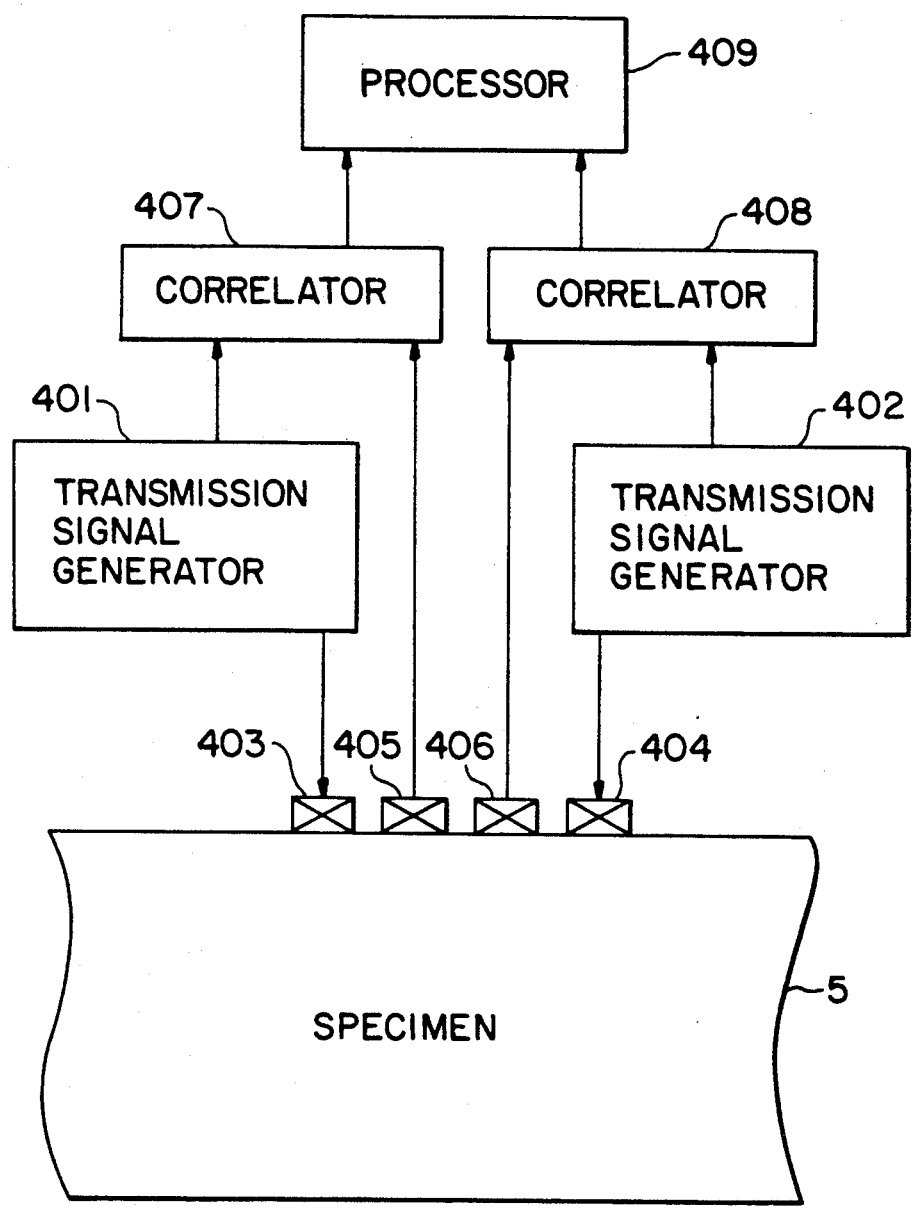
FIG. 62 shows another version of FIG. 15.

FIG. 61 is a block diagram of a detecting apparatus including a first transmission signal generator 401 for generating a first transmission signal which has a wave form comprising smoothly curved portions, a second transmission signal generator 402 for generating a second transmission signal which has a wave form comprising smoothly curved portions, a first transmitting means 403 for transmitting waves to an object by the first transmission signal, a second transmitting means 404 for transmitting waves to the object by the second transmission signal, a first receiving means 405 for receiving a first echo corresponding to the first transmission signal, a second receiving means 406 for receiving a second echo corresponding to the second transmission signal, a first correlator 407 for performing a first correlation operation with respect to the first echo, a second correlator 408 for performing a second correlation operation with respect to the second echo, and a processor 409 for processing results of the first and second correlation operations, whereby a signal which has substantially zero range sidelobes is obtained. As shown in FIG. 15, a single generator can be utilized as the first and second transmission signal generating means. Also, a single transmitting means can be utilized as the first and second transmitting means. A single receiver can be utilized as the first and second receiving means. A single correlator can be utilized as the first and second correlation operation means. The transmitting means and the receiving means can be constituted by a single common transmitting receiving means. The results of the first and second correlation operations can be substantially in complementary relationship. The first and second transmission signals can be substantially in complementary relationship. Each of the first and second transmission signals can have a wave form constituted by substantially sinusoidal portions. The first and second transmission signals can be alternately generated in timing. A center frequency of each of the transmission signals can be determined by frequency response characteristics of the transmitting means, frequency response characteristics of the object and frequency response characteristics of the receiving means whereby a signal to noise ratio is maximized. Waves transmitted from the transmitting means to the object can be ultrasonic waves. The first and second transmission signals can correspond to a first and a second sequence respectively where such first and second sequences are substantially in complementary relationship. The first correlation operation can be performed between the first echo and a first reference signal, and the second correlation operation can be performed between the second echo and a second reference signal. The first and second reference signals can be the first and second transmission signals, respectively. The first reference signal can be a first echo related to the first transmission signal from the surface or the bottom of the object, and the second reference signal can be a second echo related to the second transmission signal from the surface or the bottom of the object. As another alternative, the first reference signal can be one computed based on frequency response characteristics of a signal path from an output portion of the first transmission signal generator through the object to an input portion of the first correlator and the first transmission signal, and the second reference signal can be one computed based on frequency response characteristics of a signal path from an output portion of the second transmission signal generating means through the object to an input portion of the second correlator and the second transmission signal. Each of the frequency characteristics can then include frequency response characteristics relating to reflection of a reflection body in the object. The first reference signal can instead be an echo from a portion of a trial object when waves are transmitted to the object from the first transmitting means by the first transmission signal, and the second reference signal can be an echo from the portion of the trial object when waves are transmitted to the trial object from the second transmitting means by the second transmission signal. The first reference signal can be a signal which has the same wave form as the first echo has, and the second reference signal can be a signal which has the same wave form as the second echo has.

Figure 1:
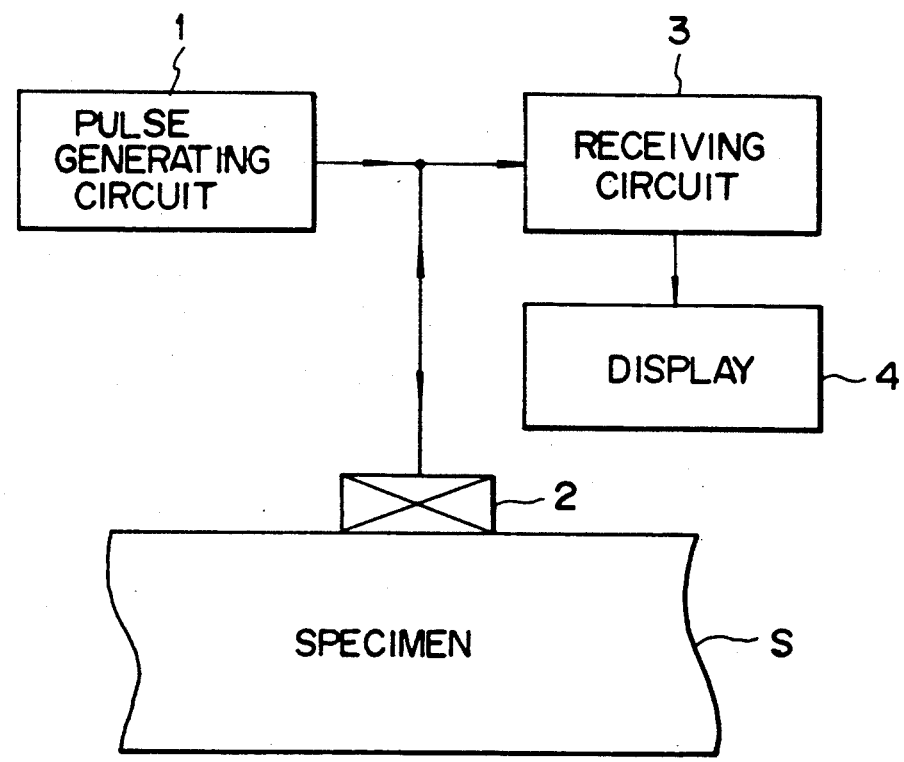
FIG. 1 shows a conventional ultrasonic non-destructive inspecting apparatus in a block diagram.
Figure 2A:
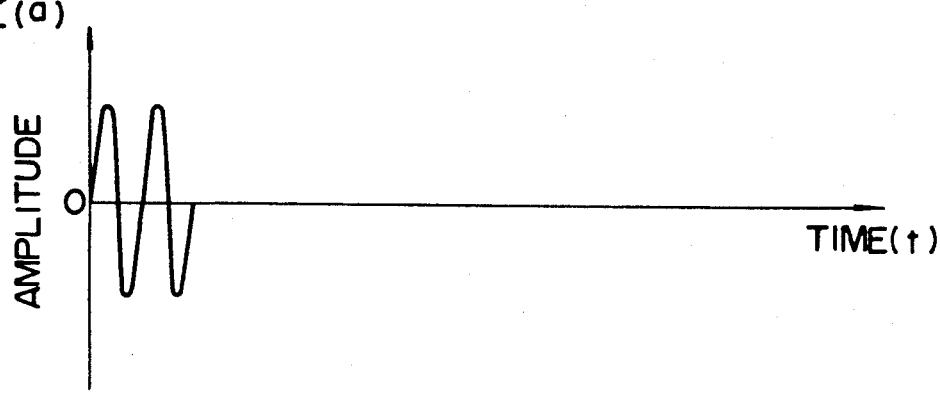
FIGS. 2(a)–(c) explain an operation of the conventional ultrasonic non-destructive inspecting apparatus.
Figure 2B:
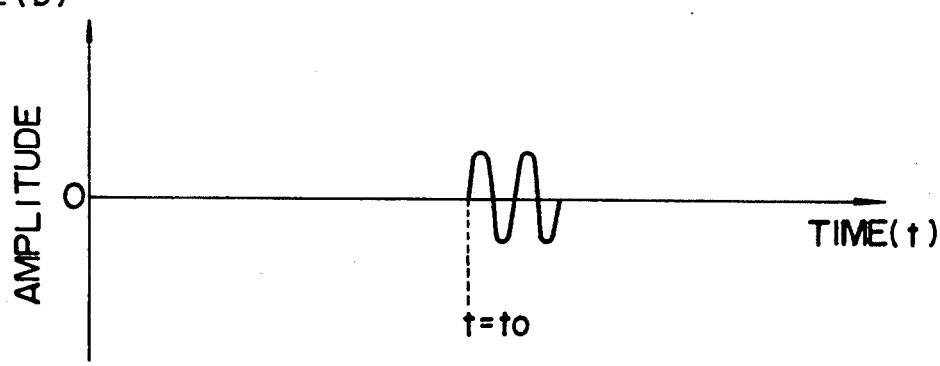
Figure 2C:
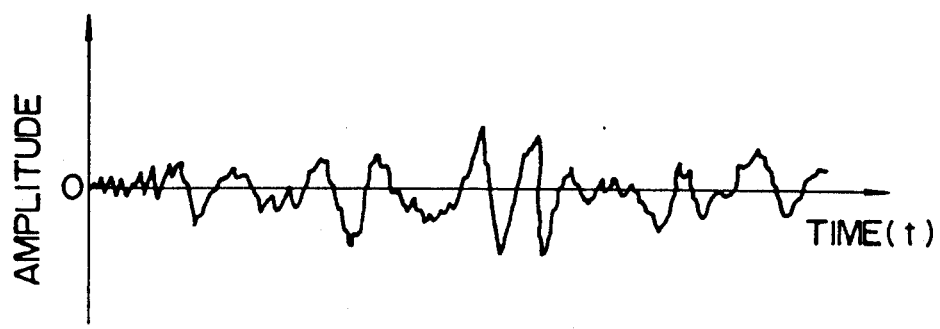
Figure 24:
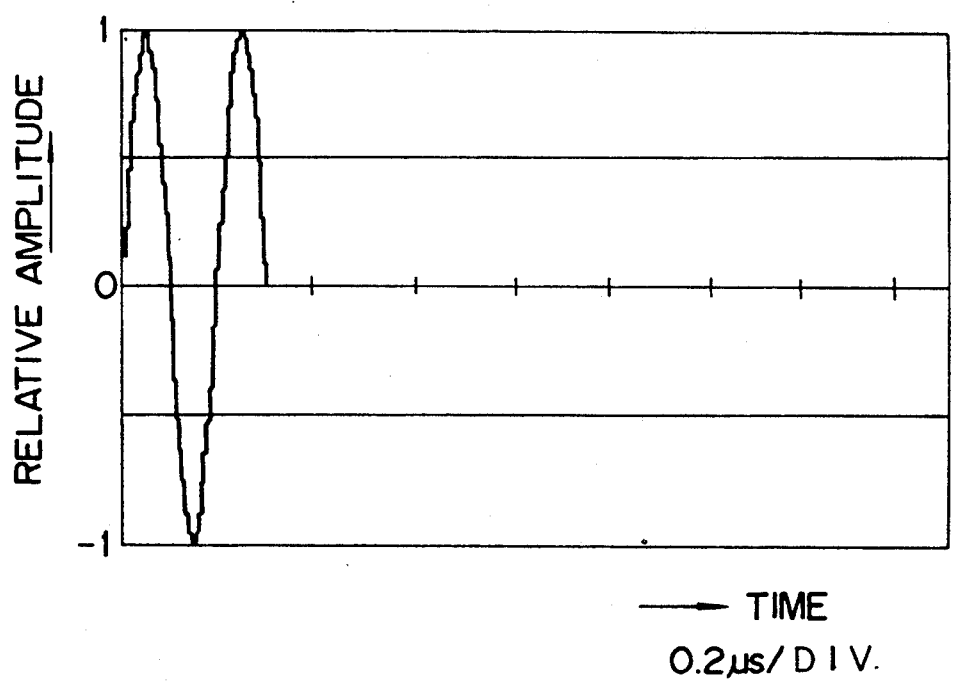
FIGS. 24(a) and (b) show a wave form indicating an operation of a conventional ultrasonic inspecting apparatus.
Figure 24:
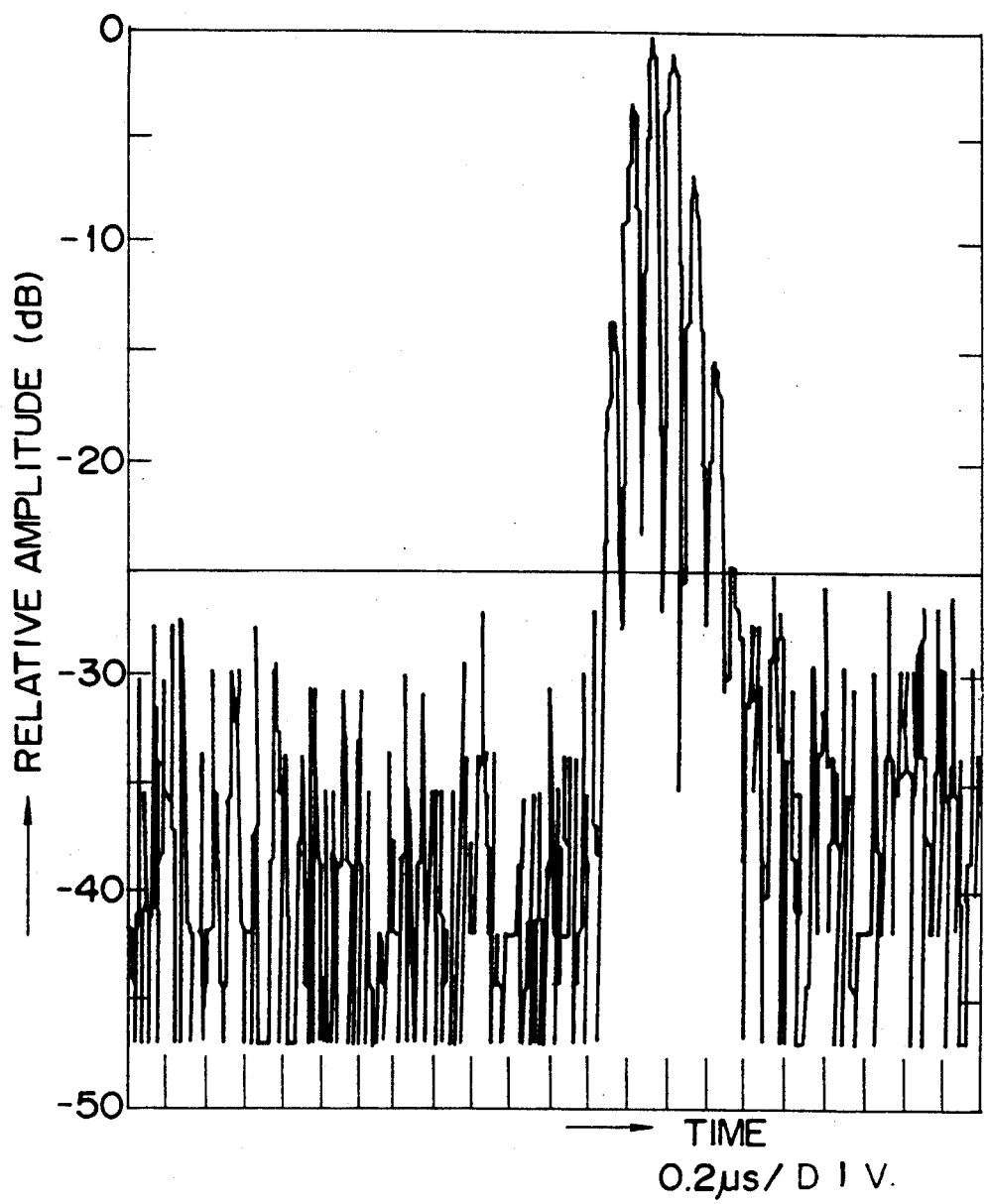

Further, for the sake of comparison, an operation of the conventional apparatus of an impulse type shown in FIG. 1 is explained referring to FIGS. 24(a) and (b). Incidentally, the ultrasonic probe 102 and the specimen S are the same as those in the first embodiment.

By the signal shown in FIG. 24(a), the ultrasonic probe 102 was driven. This signal is the same with respect to its wave form and its peak amplitude as those of the unit portion of the transmission signals $S_a^{}(t)$ and $S_b^{}(t)$.

The reflection echo shown in FIG. 24(b) was measured. On this echo, noises were seriously superimposed and an S/N ratio was only about 25 dB.

Therefore, it is noted that, upon comparing the results shown in FIGS. 23 and 24(b), the first embodiment according to the present invention achieves an advantageous effect in that an S/N ratio is improved by around 7 dB, and also achieves an advantageous effect in that the efficiency of utilizing transmission energy is made higher as shown in FIG. 19.

Figure 25:
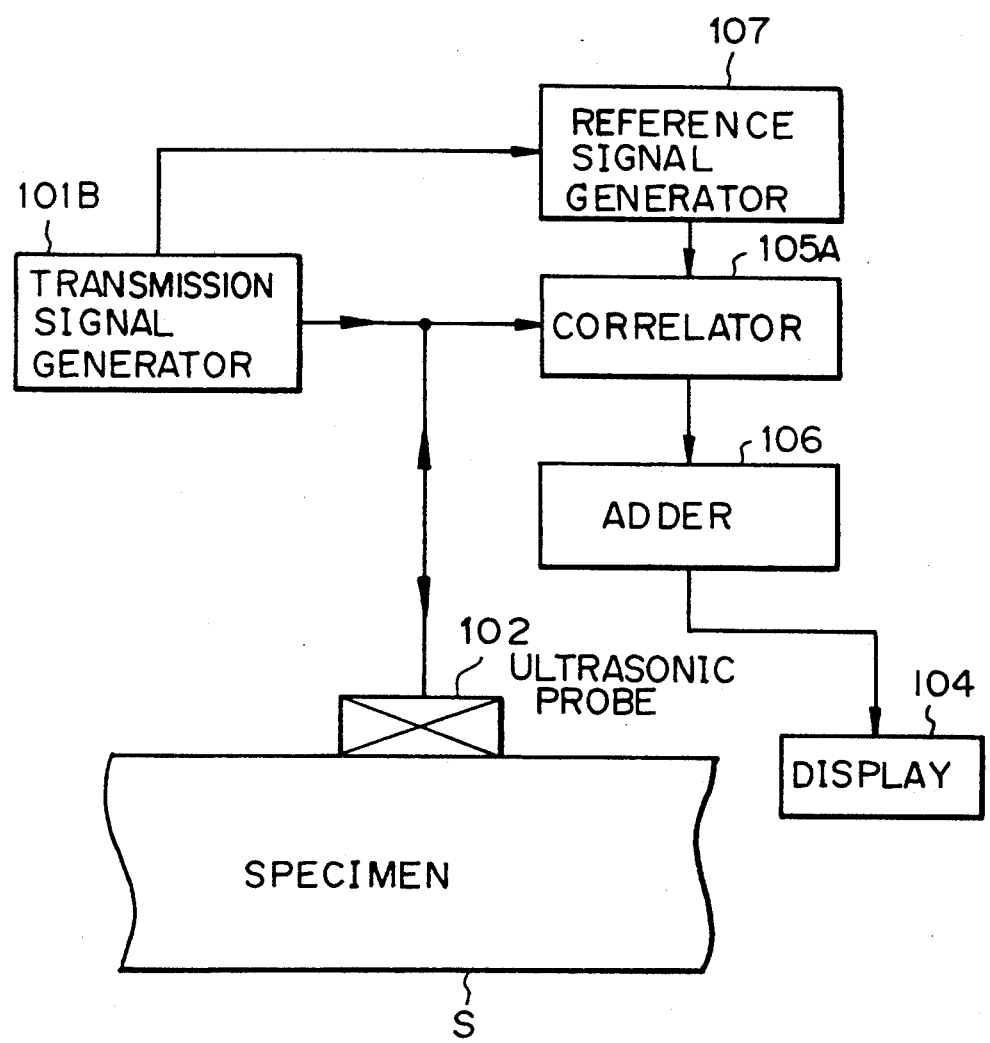
FIG. 25 shows a second embodiment according to the present invention in a block diagram.

A construction of the second embodiment according to the present invention is explained referring to FIG. 25 wherein a transmission signal generator 101B, an ultrasonic probe 102, a correlator 105A, an adder 106 and a display 104 are the same as those in the first embodiment.

In the second embodiment shown in FIG. 25, it is constructed by the same components as those in the first embodiment and, as different components, a reference signal generator 107 an input side and an output side of which are connected to the transmission signal generator 101B and the correlator 105A, respectively. An operation of the second embodiment is explained referring to FIGS. 26 and 27.

Incidentally, the operating conditions are the same as those in the case of the first embodiment.

At first, the transmission signal generator 101B generates transmission signals $S_a^{}(t)$ and $S_b^{}(t)$ to drive the ultrasonic probe 102. These transmission signals $S_a^{}(t)$ and $S_b^{}(t)$ are the same as those in the first embodiment.

The ultrasonic probe 102 is driven by the transmission signals $S_a^{}(t)$ and $S_b^{}(t)$, transmits ultrasonic waves to the specimen S, receives their reflection echoes $G_a^{}(t)$ and $G_b^{}(t)$ and transmits them to the correlator 105A.

On the other hand, the reference signal generator 107 generates reference signals $h_a(t)$ and $h_b(t)$ based on the transmission signals $S_a^{}(t)$ and $S_b^{}(t)$ respectively and transmits them to the correlator 105A.

These reference signals $h_a(t)$ and $h_b(t)$ are signals obtained by passing the transmission signals $S_a^{}(t)$ and $S_b^{}(t)$ twice respectively through the ultrasonic probe 102 exhibiting filtering function at the time of both transmitting and receiving.

That is, let us express the filtering characteristics (impulse response characteristics) of the ultrasonic probe 102 exhibited at the time of transmitting and receiving by $U_1(t)$ and $U_2(t)$, respectively. Then the reference signals are expressed by the following equations.

$$h_a(t) = \int\int S_a^{**}(t')U_1(t''-t')U_2(t''-t)dt'dt''$$
[integrating range: $-\infty \sim \infty$] (107)

$$h_b(t) = \int\int S_b^{**}(t')U_1(t''-t')U_2(t''-t)dt'dt''$$
[integrating range: $-\infty \sim \infty$] (108)

Incidentally, the reference signals $h_a(t)$ and $h_b(t)$ actually used are those obtained beforehand by measuring the reflection echo from the bottom surface of the specimen when the ultrasonic probe 102 is driven by the transmission signals $S_a^{}(t)$ and $S_b^{}(t)$, respectively. The reason why such reference signals were chosen is that the reflection echo from the bottom surface of the specimen S is equivalent to the signal obtained by passing the transmission signals $S_a^{}(t)$ and $S_b^{}(t)$ through the ultrasonic probe 102 having the filtering function twice and that the reflection echo from the bottom surface can be measured with a high S/N ratio.

The correlator 105A performs correlation operations between the reflection echoes $G_a^{}(t)$ and $G_b^{}(t)$ and the reference signals $h_a(t)$ and $h_b(t)$ with a variable $\tau$ being changed. The equations regarding the above correlation operations are given as follows:

$$\int G_a^{**}(t)h_a(t-\tau)dt \text{ [integrating range: } -\infty \sim \infty\text{]} \quad (109)$$

$$\int G_b^{**}(t)h_b(t-\tau)dt \text{ [integrating range: } -\infty \sim \infty\text{]} \quad (110)$$

The actual integrating ranges in the equations (109) and (110) were limited to finite ranges. That is, ranges where the reference signals may be, without no serious harm, regarded as substantially zero were cutted off. In other words, if symbols $T_a$ and $T_b$ are assigned to time width, respectively wherein the reference signals $h_a(t)$ and $h_b(t)$ cannot be regarded as zero, the following integrating ranges were employed in the above equations (109) and (110), respectively.

$$-T_a/2+\tau \sim T_a/2+\tau,$$

$$-T_b/2+\tau \sim T_b/2+\tau.$$

FIGS. 26(a) and (b) show the results of the correlation operations according to the equations (109) and (110) with the use of the above integrating ranges.

Finally, the adder 106 sums the results of the correlation operations according to the equations (109) and (110).

Figure 27:
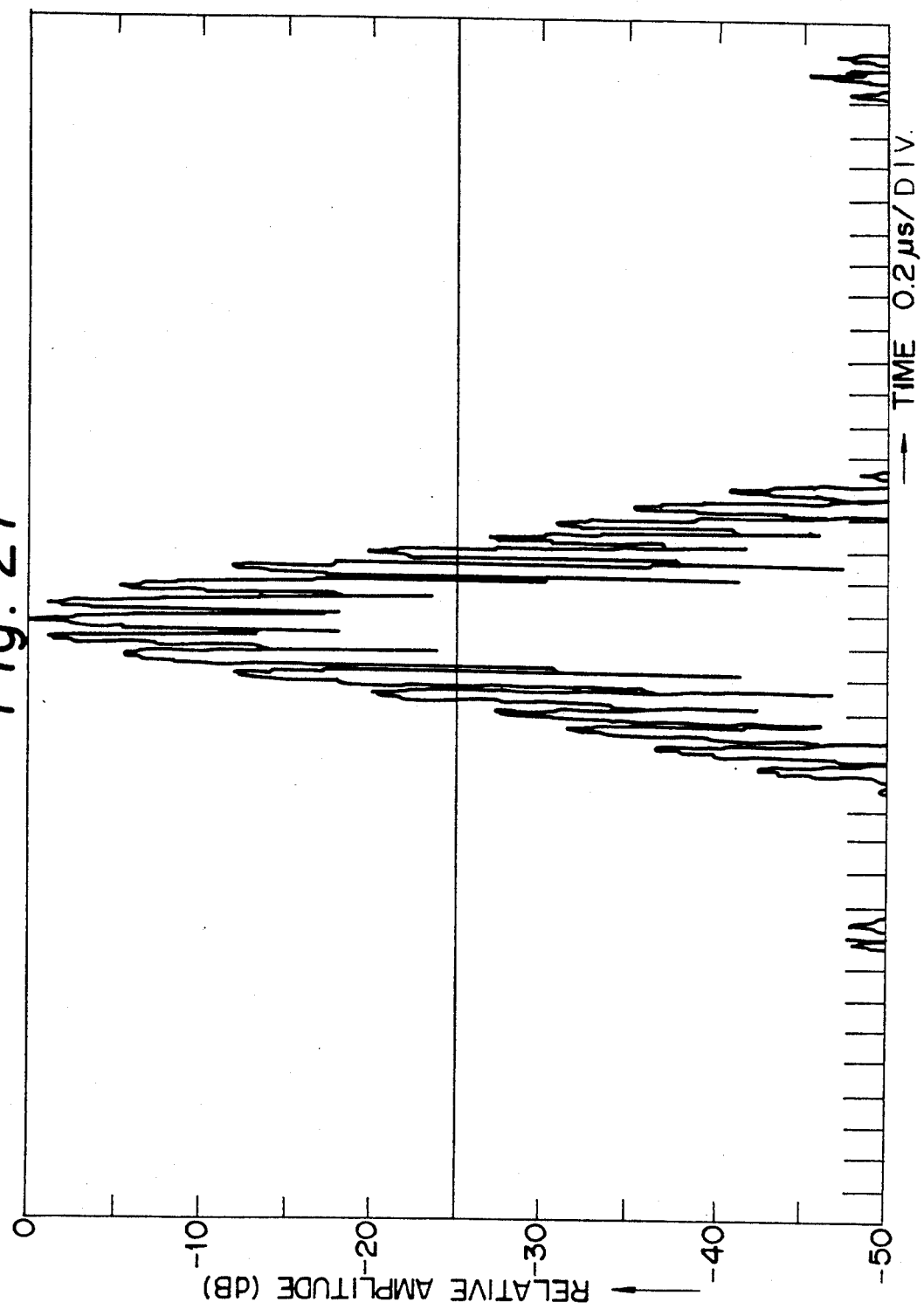
FIG. 27 shows a wave form of a summing result of correlation operations in the second embodiment of the present invention.

That is, the result of the correlation operation according to the equation (109) is stored in an internal memory of the adder 106 and, in the next time phase, the result of the correlation operation according to the equation (110) and the stored result of the equation (109) are summed. FIG. 27 shows the result of the summing operation.

Upon comparing this result with the result, shown in FIG. 23, of the correlation operations and the summing operation in the first embodiment wherein the levels of the range sidelobes are below $-32$ dB, it is noted that the levels of range sidelobes are below $-48$ dB in FIG. 27 and the level of range sidelobes is improved approximately by 16 dB in the second embodiment.

Since the second embodiment according to the present invention is constructed as above, it is useful even under unfavorable condition where an S/N ratio is inferior and achieves an advantageous effect in that the levels of range sidelobes can be remarkably lowered.

Incidentally, in the first and second embodiments, the signals were all digitized and correlation operations and summing operations were performed using a computer.

As a means for performing a correlation operation, several kinds of means may be considered. Two practical means for performing a correlation operation are explained referring to FIGS. 28 and 29.

Figure 28:
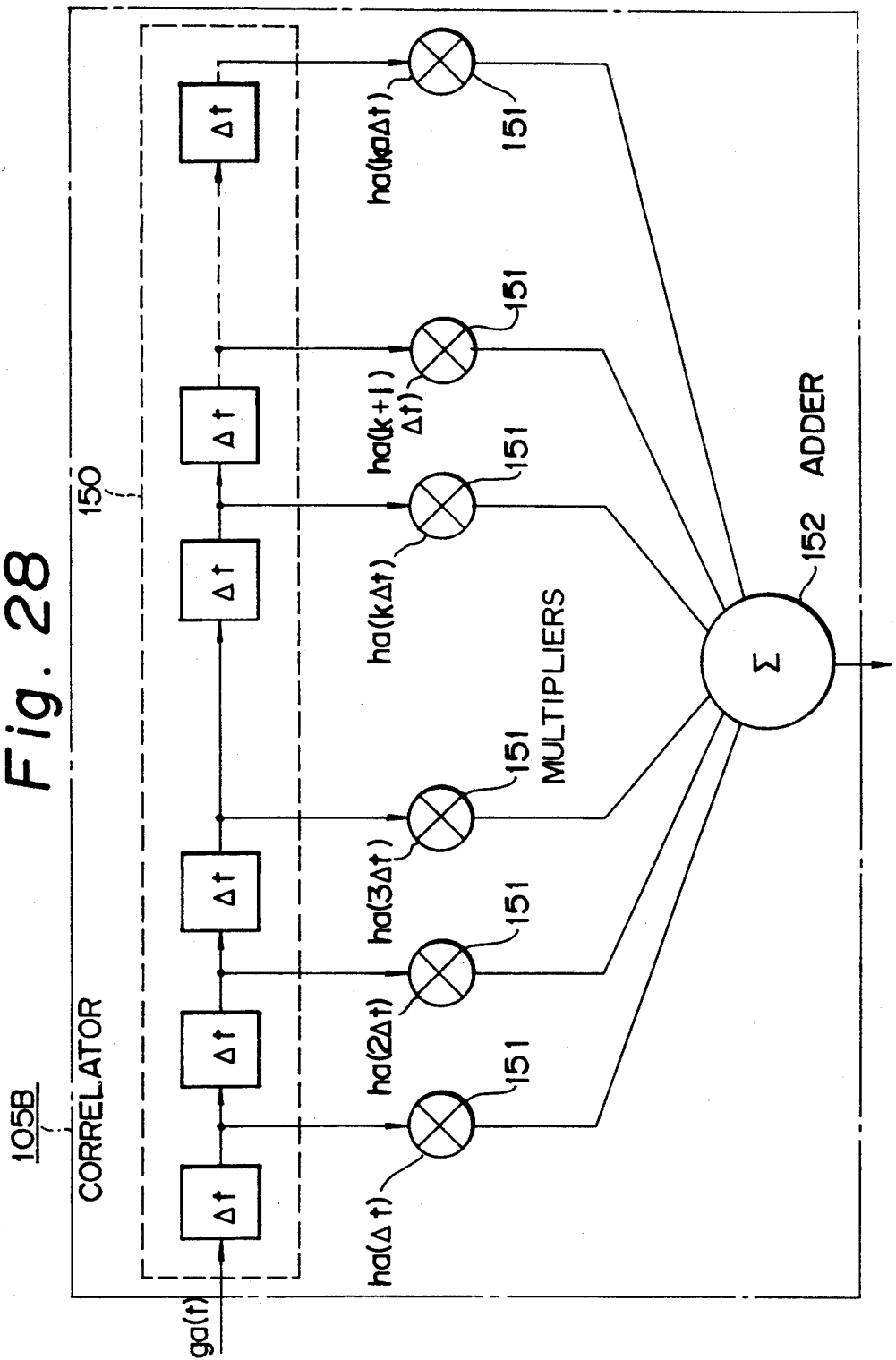
FIG. 28 is a block diagram showing an example of a correlator of the present invention.

In FIG. 28, a correlator 105B comprises a tapped delay line 150 connected to the ultrasonic probe 102, plural number ($K_a$) of multipliers 151 connected to the tapped delay line 150 and an adder 152 connected to the multiplier 151.

This correlator 105B performs a correlation operation with utilizing the feature of the equation (109) which may be modified as follows:

That is the equation (109) can be modified as noted below.

$$\int G_a^{**}(t)h_a(t-\tau)dt \text{ [integrating range: } -\infty \sim \infty\text{]} \quad (111)$$
$$= \int G_a^{**}(t+\tau)h_a(t)dt \text{ [integrating range: } -\infty \sim \infty\text{]}$$
$$\approx \int G_a^{**}(t+\tau)h_a(t)dt \text{ [integrating range: } 0 \sim T_a\text{]}$$
$$\approx \Sigma G_a^{**}(k\Delta t + l\Delta t)h_a(k\Delta t) \text{ } [k=1 \sim K_a]$$

wherein
k, l: integer
$\Delta t$: sampling interval
$k_a$: constant
$t = k\Delta t$,
$\tau = l\Delta t$, and
$T_a = K_a \Delta t$.

In the correlator 105B, $\Delta t$ is a delay time between the taps of the tapped delay line 150 and $K_a$ is a total number of taps. When the reflection echo $G_a^{**}(t)$ is inputted to the tapped delay line 150, an output of a tap, for example, of the kth tap is multiplied with a pre-known weight $h_a(k\Delta t)$ by the multiplier 151. Thereafter, the adder 152 sums outputs from all the taps and the result thereof is equal to the above equation (111)

Also, the equation (110) can be modified as follows:

$$\int G_b^{**}(t)h_b(t-\tau)dt \text{ [integrating range:}$$
$$-\infty \sim \infty] \approx \Sigma G_b^{**}(k\Delta t)h_b(k\Delta t) \text{ } [k=1 \sim K_b] \quad (112)$$

wherein $T_b K_b \Delta t$.

The respective correlation operations of the equations (1111) and (112) may be performed at different timing phases. In this case, it is possible to use the same and single correlator 105B and simply replace the weights $h_a(k\Delta t)$ in the same construction by the weights $h_b(k\Delta t)$, respectively.

Also the same result and effect can be expected with utilizing two systems comprising another tapped delay line, another multipliers and another adder in addition to the tapped delay line 150, multipliers 151 and the adder 152 for performing the two correlation operations independently.

Figure 29:
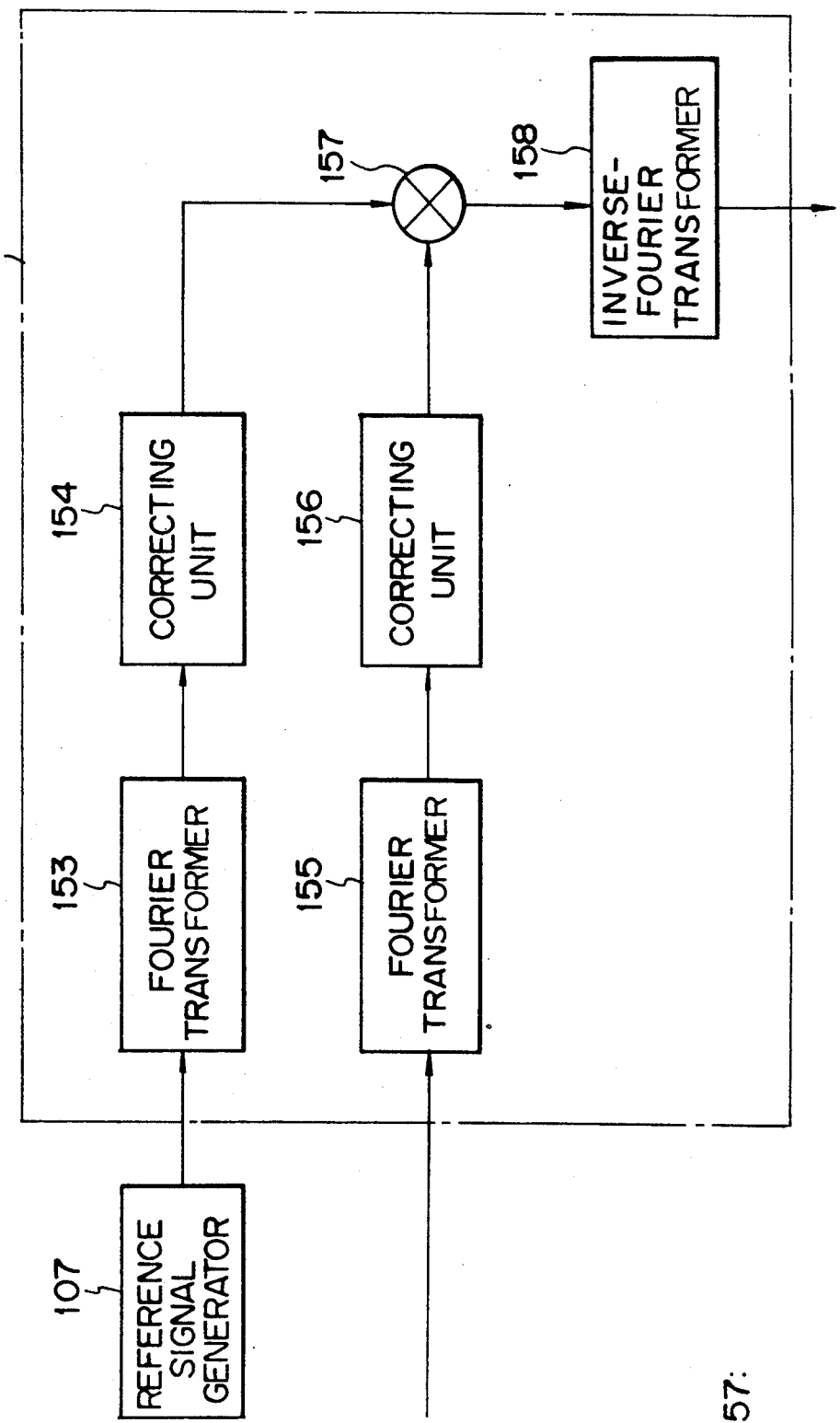
FIG. 29 is a block diagram showing another example of a correlation of the present invention.

In FIG. 29, another correlator 105C is shown and it comprises a Fourier transformer 153 connected to the reference signal generator 107, a corrector 154 connected to the Fourier transformer 153, a Fourier transformer 155 connected to the ultrasonic probe 102, a corrector 156 connected to the Fourier transformer 155, a multiplier 157 connected to the correcting units 154 and 156 and an inverse-Fourier transformer 158 connected to the multiplier 157.

This correlator 105C utilizes the fact that the results of the correlation operations expressed by the equations (109) and (110) are equivalent to results obtained by Fourier transforming the respective signals with following multiplication and further inverse-Fourier transforming.

That is, the Fourier transformer 153 transforms the reference signals $h_a(t)$ and $h_b(t)$ from the reference signal generator 107 and the Fourier transformer 155 transforms the reflection echoes $G_a^{}(t)$ and $G_b^{}(t)$. The correcting units 154 and 156 can correct frequency response characteristics of the specimen S, such as frequency characteristics of ultrasonic attenuation, also can correct the frequency response characteristics of the ultrasonic probe 102.

The multiplier 157 performs multiplication between the corrected reflection echo $G_a^{}(t)$ and the corrected reference signal $h_a(t)$ and similarly multiplication between the corrected reflection echo $G_b^{}(t)$ and the corrected reference signal $h_b(t)$.

The inverse-Fourier transformer 158 performs inverse-Fourier transformation of the result of the above multiplication.

This correlator 105C can, for the reason explained hereinafter, reduce the levels of range sidelobes to zero, i.e. an ideal state. That is, the correcting units 154 and 156 can also correct the frequency response characteristics, i.e. filtering characteristics, of the ultrasonic probe 102. For example, the reference signals $h_a(t)$ and $h_b(t)$ are, as shown in equations (107) and (108), dependent on the impulse responses $U_1(t)$ and $U_2(t)$ of the ultrasonic probe 102. Therefore, if the impulse responses $U_1(t)$ and $U_2(t)$ are corrected so that they approximate as possible as close to $\delta$ function in the time domain, the reference signals $h_a(t)$ and $h_b(t)$ become close to the transmission signals $S_a^{}(t)$ and $S_b^{}(t)$, respectively. On the other hand, reflection echoes $G_a^{}(t)$ and $G_b^{}(t)$ are also corrected regarding the specimen S and the ultrasonic probe 102. Accordingly, it is possible to approximate the level of range sidelobes to an ideal state, i.e. zero as shown in FIG. 18.

While, in the correlator 105C explained above, the reference signals $h_a(t)$ and $h_b(t)$ were Fourier transformed by the Fourier transformer 153, the similar effect and advantage can also be expected by transmitting the computed results of the Fourier transforms of the reference signals $h_a(t)$ and $h_b(t)$ to the multiplier 157 at a proper time. In this case, the computed results are previously obtained by Fourier transformation and stored at appropriate memories.

In the correlator 105C explained above, two correcting units 154 and 156 are employed; however, a single correcting unit may be connected to a rear stage of the multiplier 157 to achieve the anticipated same effect.

In the above explanation regarding the correlators 105B and 105C, correlation operations between the reflection echoes and reference signals are explained; however, they may be utilized to perform correlation operations between the reflection echoes and the transmission signals. In the latter case, portions corresponding to the reference signals may be replaced by the transmission signals. The correlators 105B and 105C may be constructed by means of either software or hardware. It has been confirmed that the respective embodiments explained above can also achieve the same several effects and advantages as those explained under the following conditions.

The test was practiced with a cycle number $f_0T$ being changed in the range of 0.5~3.0 by each increment of 0.5 and further with an interval $T'$ between sinusoidal wave portions for each cycle number $f_0T$ being changed in a range of $F_0T \sim f_0T+2.0$ by each increment of 0.5.

The test was also practiced using metals exhibiting a high attenuation such as an austenite stainless steel and a titanium alloy, etc. as a specimen S.

Further, in the second embodiment, actual measured data of the reflection echoes from the bottom surface of the specimen S were employed as the reference signal $h_a(t)$ and $h_b(t)$; however, the similar effect can be expected by using data obtained from the following calculation. That is, if material constants of the specimen S and components constituting the ultrasonic probe 102 are known, the impulse response characteristics of the ultrasonic probe 102 and the frequency response characteristics derived by Fourier transformation thereof can be obtained by calculations, for example, noted on pages 762–767 of "Non-Destructive Test", Vol. 30, No. 10, 1981, and also the frequency response characteristics of the specimen S can be calculated.

A third embodiment according to the present invention will be explained referring to FIG. 30.

Figure 30:
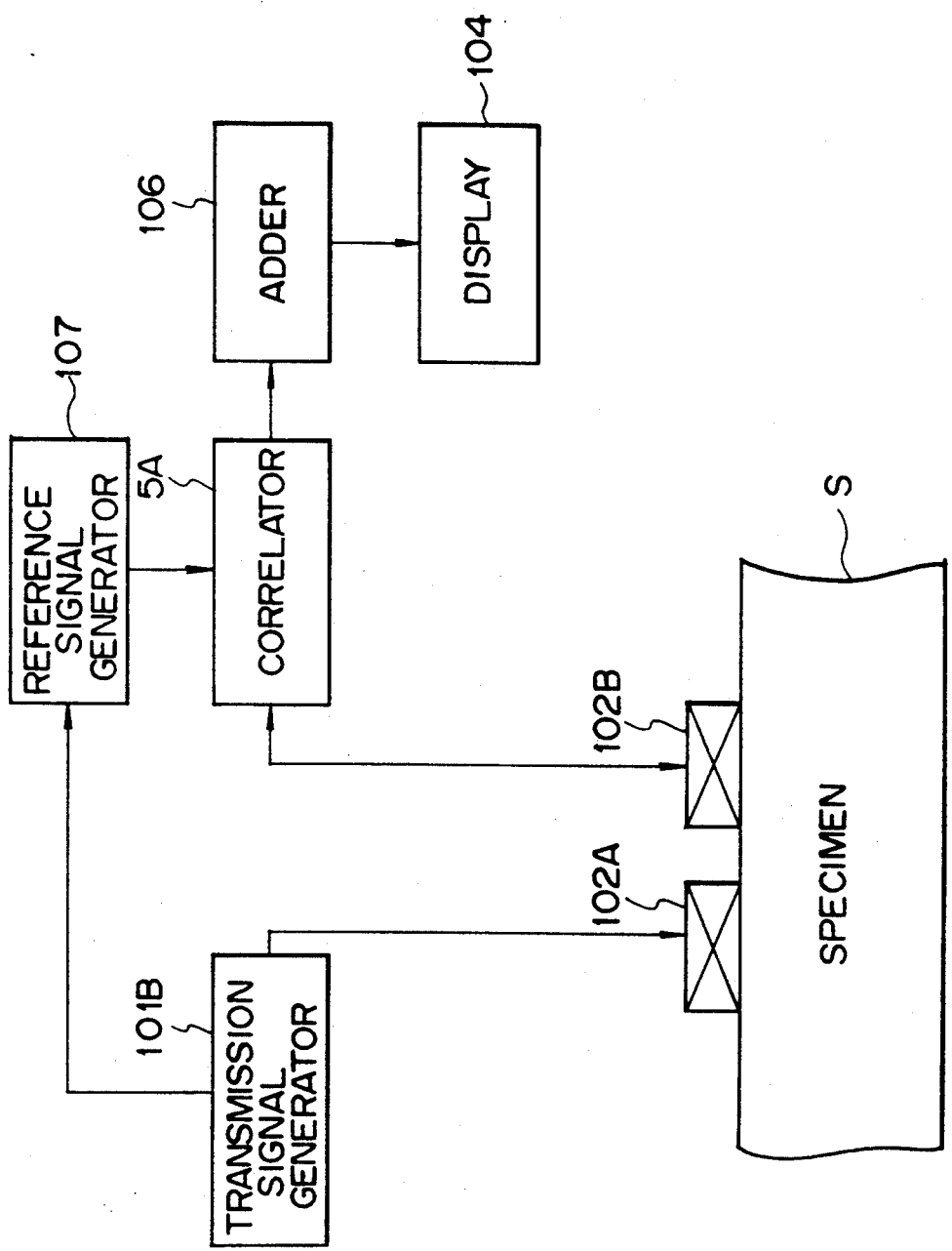
FIG. 30 shows a third embodiment according to the present invention.

In FIG. 30, the third embodiment of the present invention comprises the same elements are those in the second embodiment (except for the probe), and others, namely a transmitting ultrasonic probe 102A connected to the transmission signal generator 101B and a receiving ultrasonic probe 102B connected to the correlator 105A.

In the third embodiment, the impulse responses of the ultrasonic probes 102A and 102B are used as $U_1(t)$ and $U_2(t)$, respectively, in the equations (107) and (108).

The third embodiment exhibits the similar effect and advantage as those in the second embodiment.

It is, of course, possible, to apply the transmitting ultrasonic probe 102A and the receiving ultrasonic probe 102B to the first embodiment of the present invention.

Figure 31:
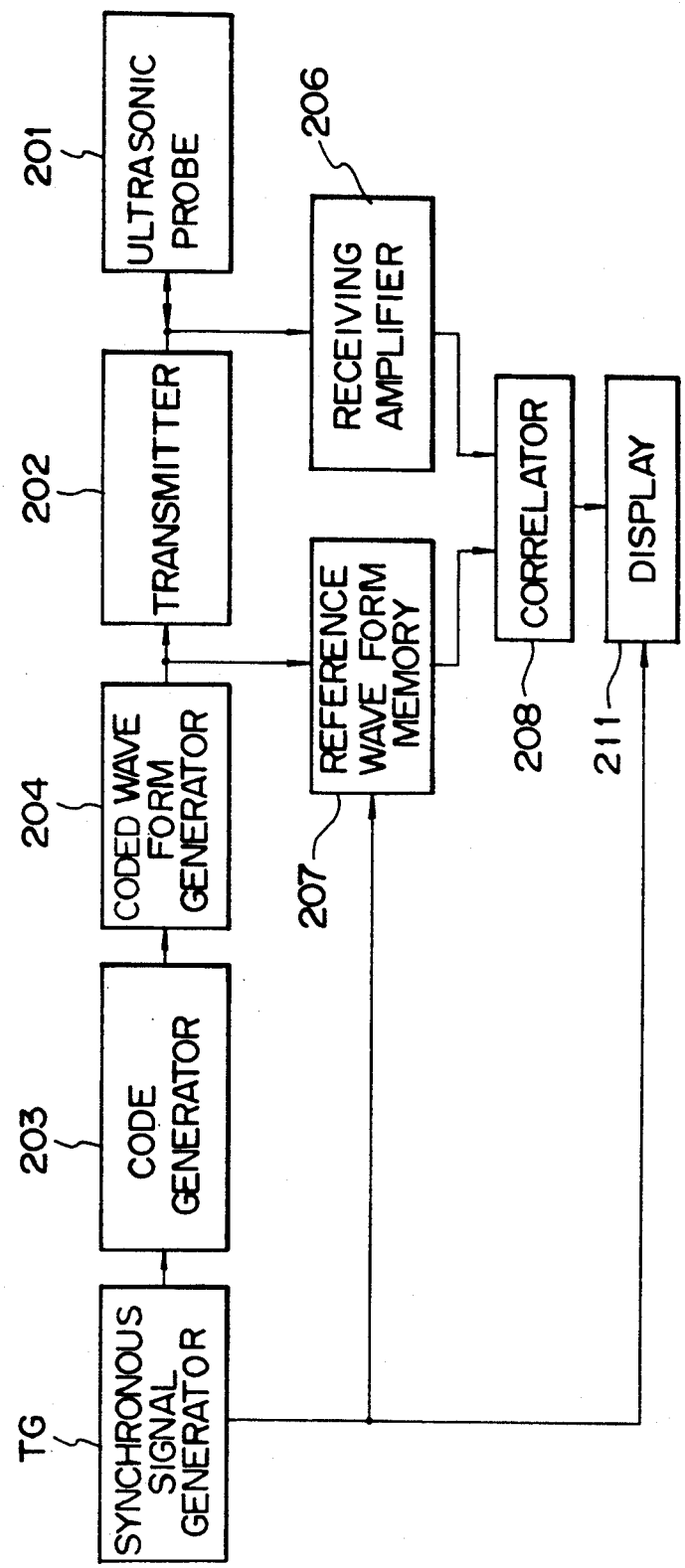
FIG. 31 shows a construction of a fourth embodiment according to the present invention.

In FIG. 31, a fourth embodiment according to the present invention is shown in a block diagram schematically illustrating its construction. An ultrasonic probe 201, a transmitter 202 and a display 211 are the same as those in the prior art explained. TG designates a synchronous signal generator for controlling transmitting times, 203 a code generator connected to the synchronous signal generator TG and adapted to generate a finite binary sequence, 204 a coded wave form generator adapted to be inputted with the binary sequence having positive and negative values from the code generator 203 for generating wave forms having a frequency component $f_0$ and phases of which are changed by 180° in correspondence to the positive value or the negative value of the binary sequence, 206 an amplifier for amplifying flaw signals received by the ultrasonic probe 201, 207 a wave form memory for normalizing and storing the transmission signals generated at the coded wave form generator 204 and for outputting them when required, and 208 a correlator for performing a correlation operation between the flaw signal outputted from the amplifier 206 and the reference wave form stored in the reference signal memory 207.

FIGS. 32 are drawings for explaining an operation of the fourth embodiment shown in FIG. 31. FIG. 32(a) shows a synchronous signal generated from the synchronous signal generator TG. FIG. 32(b) a sequence having a sharp autocorrelation function (a Barker sequence in this instance) outputted from the code generator 203, FIG. 32(c) a signal generated at the coded wave form generator 204, FIG. 32(d) a flaw signal inputted into the correlator 208 from the amplifier 206, and 32(e) an output signal from the correlator 208.

Figure 33:
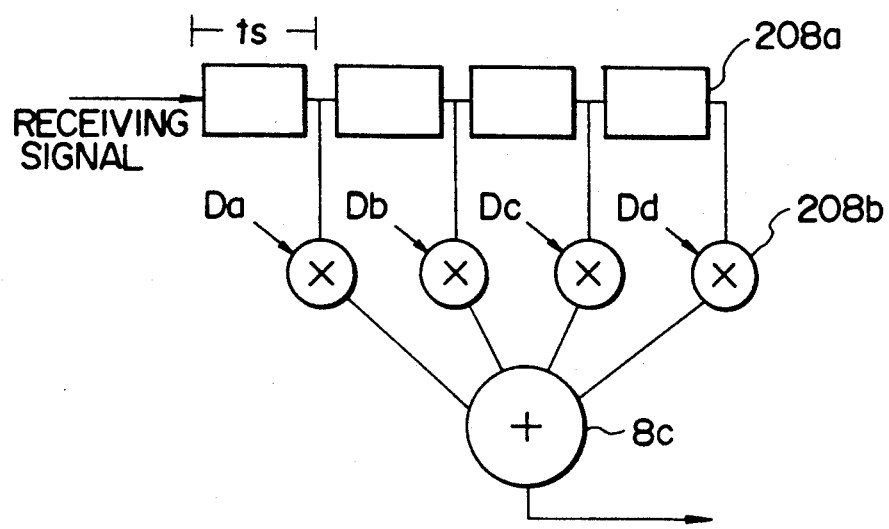

FIG. 33 is a drawing for explaining a construction of the correlator 208 wherein 208a are delay elements employing a shift register etc. and having a unit delay time, for example, in an order of $1/5 \sim 1/10$ of $1/f_0$, 208b multipliers each for performing a multiplication with data from the delay element 208a and reference wave form data $D_a$-$D_d$ stored in the reference wave form memory 207, and 208c an adder for summing all the results from the multipliers 208b.

Figure 32A:
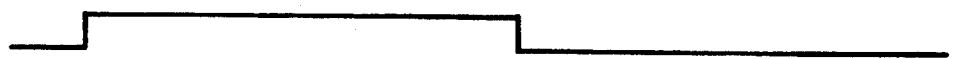
FIGS. 32 through 34 are drawings for explaining an operation and advantageous effect of FIG. 31.
Figure 32B:
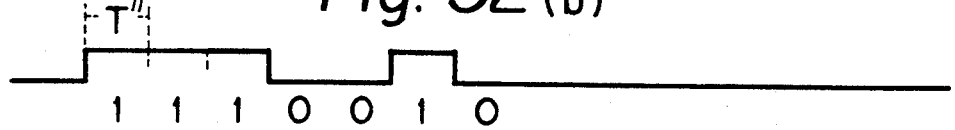
Figure 32C:
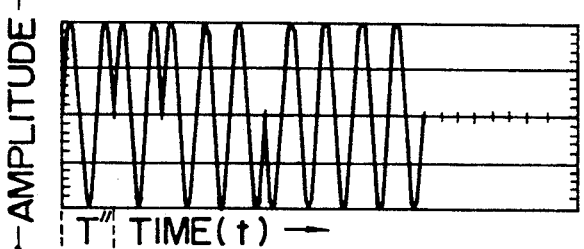
Figure 32D:
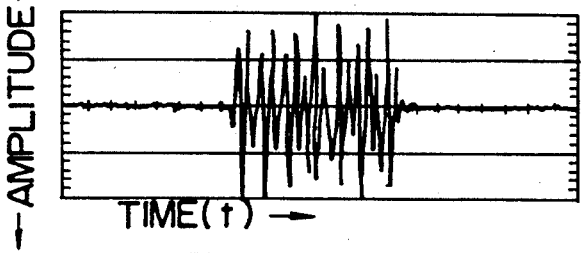
Figure 32E:
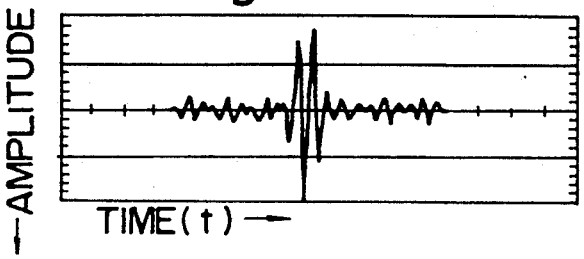

In the ultrasonic inspecting apparatus constructed as above, the coded generator 203, into which the synchronous signal shown in FIG. 32(a) generated at the synchronous signal generator TG is inputted, outputs a finite binary sequence of positive and negative values with keeping one value during a predetermined unit time T''. The output wave form of the code generator 203 is shown in FIG. 32(b). As means for generating sequences, a presettable shift register, etc. is utilized with using a shift clock unit of a unit time T''. A sequence with the unit time T'' generated at the code generator 203 is inputted into the coded wave form generator 204. A wave form having a frequency component $f_0$ is generated in the coded wave form generator 204 with a phase of 0° in case of the positive value and a phase of 180° in case of the negative value for a period of unit time T'', respectively. An example of the wave form generated at such occasion as above is shown in FIG. 32(c). In this instance, a cycle of a sine-wave is assigned in the case of positive value and a sine-wave shifted by 180° in the case of negative value. As a means for generating the wave forms as above, it is possible to employ memories with stored data of wave forms for each of positive and negative values and with the function of being read out per each value and a digital-analog converter.

The transmission signal generated at the coded wave form generator 204 is amplified at the transmitter 202 and applied to the probe 201 as well as stored in the reference wave form memory 207. If a digital system is employed regarding a system for generating the transmission signal at the wave form generator 204, storing is effected in a digital memory. Also, in the case of an analog system, storing is made in a digital memory by using an analog-digital converter.

The transmission signal applied to the probe 2011 is inputted, after being converted to an ultrasonic signal into a specimen wherein it is reflected by a reflecting body such as a flaw and returned to the probe 201. A flaw signal converted to an electric signal by the probe 201 is amplified to a predetermined level by the amplifier 206 and inputted into the correlator 208. The correlator used herein is not one used in prior art, in which an operation of the equation (3) is processed with a low speed by varying "k" for each repeating period of transmission, but it is a high speed correlator constructed, as shown in FIG. 33, to have a necessary number of multipliers and an adder for the outputs of the multipliers.

An operation of the correlator 208 is explained referring to FIG. 33.

The receiving signal outputted from the amplifier 206 is converted to a digital signal by utilizing an analog-digital converter, etc. wherein it is converted to digital values with a sampling period $t_s$. In this instance, a sampling frequency becoming as $t_s$ in the time domain may be chosen, in accordance with the sampling definition regarding a pulse wave form, to be in an order of $5 \sim 10$ times of the frequency $f_0$ used in the coded wave form generator 204. These wave form data are inputted in the delay lines 208a, utilizing such as shift registers and outputted from the respective steps of the delay lines 208a as $a_j + |k|$ shown in the equation (3). The receiving signals $a_j + |k|$ outputted at the respective steps are multiplied by respectively provided multipliers 208b with $a_j$ as in the equation (3) stored in the reference wave form memory 207. Upon summing all these results by the adder 208c, the result thereof is outputted per every sampling unit of $t_s$ by performing the operation of the right side of the equation (3) at one time. In the above description, $a_j$ is arbitrarily and not limited to $\pm 1$.

With the steps above, the transmission signal shown in FIG. 32(c) having its center component frequency $f_0$ is impressed to the probe 201 and, if the frequency $f_0$ is matched with a center frequency of the probe 201, the relationship shown in FIG. 19 is established. The transmission signal is different from a conventional transmission signal and has almost no energy in the low frequency range. Thus, almost all the energy of the transmission signal passes through the probe 201 and, therefore, it has become possible, compared to prior art wherein a transmission signal utilizing the uniform transmission voltage has been used, to pass a transmission signal with high efficiency through the ultrasonic probe so as to improve an S/N ratio over prior art.

Incidentally, in the fourth embodiment, the transmission signal was employed as the reference wave form for the correlator, and actual received signal wave form may vary to some extent depending on frequency response characteristics of the probe shown in FIG. 19 and those of the specimen constituting a passage through which the ultrasonic wave propagates.

Figure 34A:
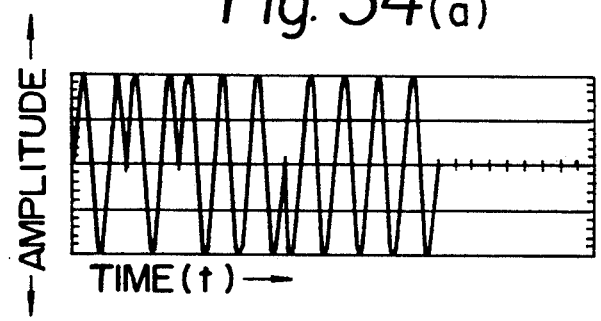
Figure 34B:
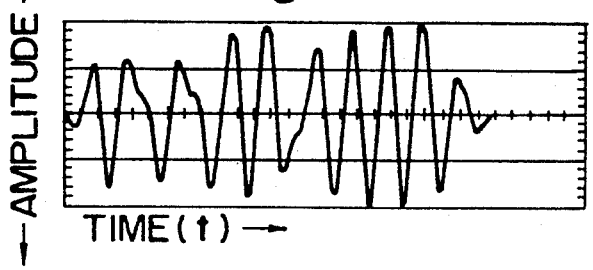

FIG. 34 show the results of actual measurement regarding variation of receiving wave forms how they were changed in the actual passage. In this instance, a so-called broad band probe having its central frequency at 5 MHz was used. FIG. 34(a) shows a wave form of the transmission signal and FIG. 34(b) shows a wave form received as the bottom surface echo from a steel plate of 25 mm thickness. In view of the principle of correlation process, the correlator 208 is characterized in that it delivers the maximum output when the same signal as the inputted receiving signal is used as a reference signal. Therefore, it has become possible according to the above embodiment to make a level of the signal after a correlation process higher and obtain a higher S/N ratio in the case where the correlation process is carried out with the wave form of FIG. 34(b) than in the case wherein a correlation process is carried out with the wave form of FIG. 34(a), the wave form such as shown in FIG. 34(b) being found by measuring the changes of transmission signal waveform depending on the frequency response characteristics along the signal passage with using standard test pieces under the preferable condition [such as in FIG. 34(b)].

Figure 35:
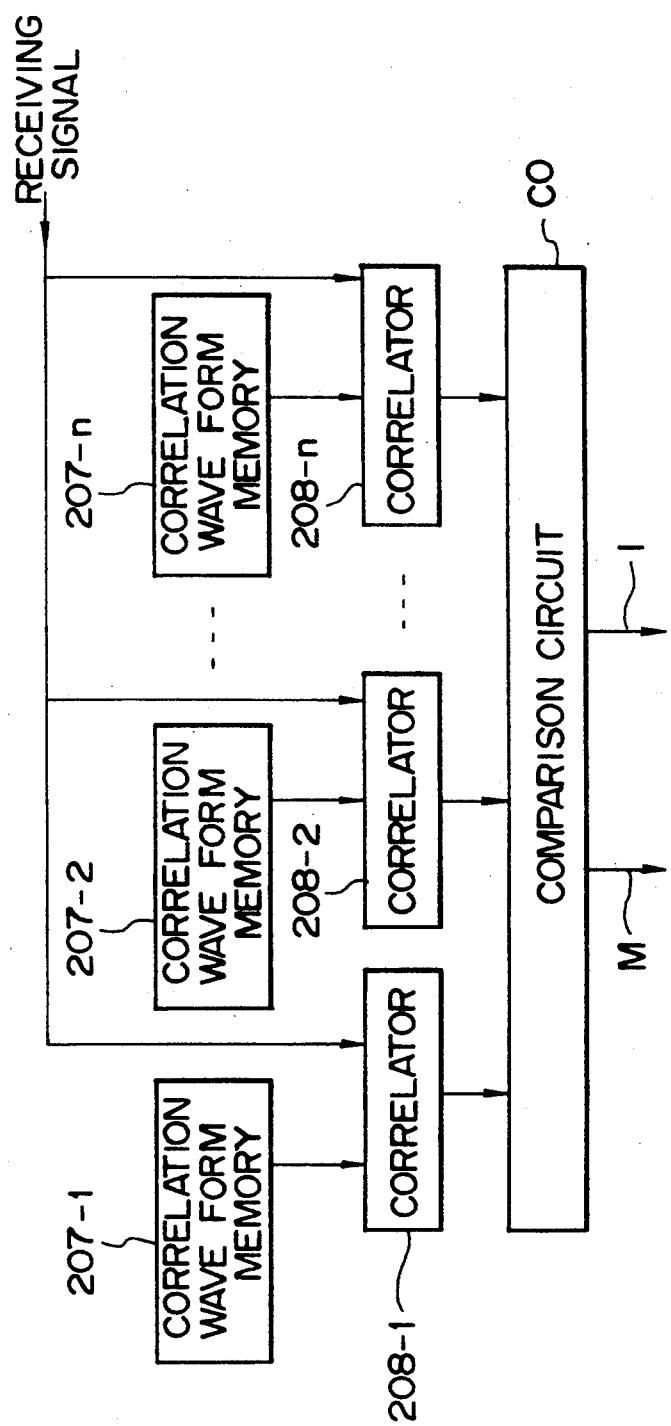
FIG. 35 shows a modified form according to the present invention.

While the present invention contributes, as explained above, to raise a level of a flaw signal contained in a receiving signal, it also provide a further advantage by constructing its wave form memory and correlator as shown in FIG. 35. The construction shown in FIG. 35 is to classify wave forms of the reflection echoes from the specimen by utilizing the features of the correlator 208 wherein 207-1, 207-2, ..., 207-n are reference wave form memories for storing reference wave forms derived from the frequency response characteristics of the ultrasonic wave propagating passages as well as the frequency response characteristics of reflectors in the specimen; 208-1, 208-2, ..., 208-n correlators corresponding to the reference wave form memories 207-1, 207-2, ..., 207-n; and CO a comparator for outputting the maximum value M of the outputs from correlators 208-1, ..., 208-n upon comparison thereof as well as outputting the reference wave form that gives maximum output as a classified flaw information.

The above is a process utilizing the features of the correlator in that the largest S/N ratio is obtained when the transmission signal and the reference signal have the same wave form. Therefore, it is possible to classify the flaws to some extent in real time by storing plural reflection signals previously obtained such as reflection signals from laminated planes or non-directional flaws in the correlation wave form memories 207-1, ..., 207-n, performing the respective correlation processes in the correlators 208-1, ..., 208n and comparing the degrees of the respective outputs for the same echo.

Figure 3A:
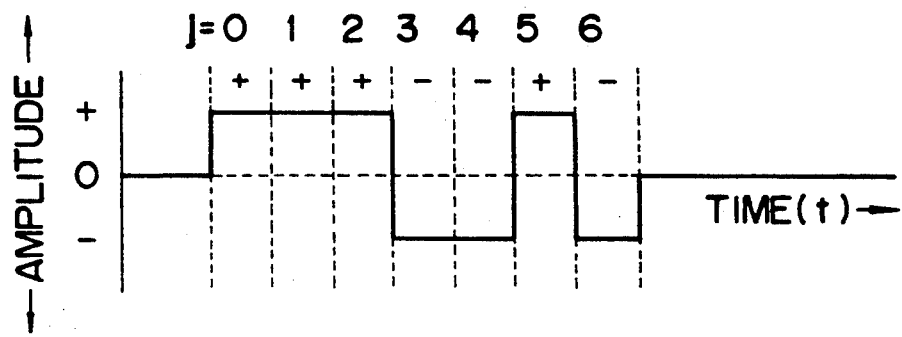
FIGS. 3(a) and (b) are graphs showing an operational principle of a Barker series.
Figure 3B:
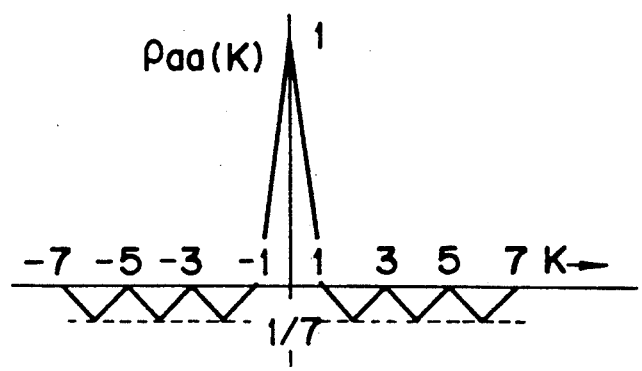
Figure 4A:
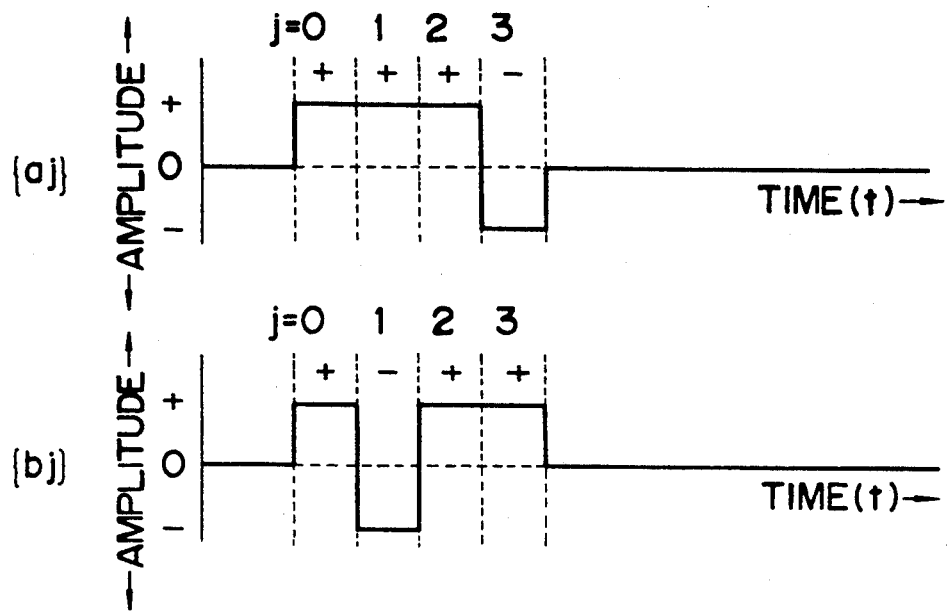
FIGS. 4(a), (b) and (c) are graphs showing a complementary sequence for explaining a conventional example.
Figure 4B:
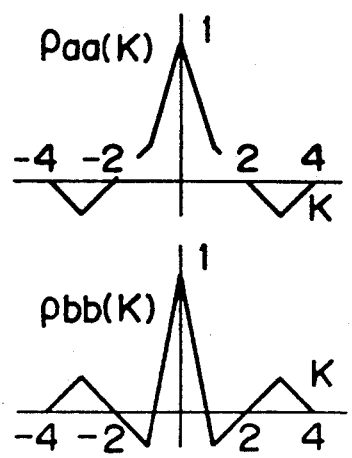
Figure 4C:
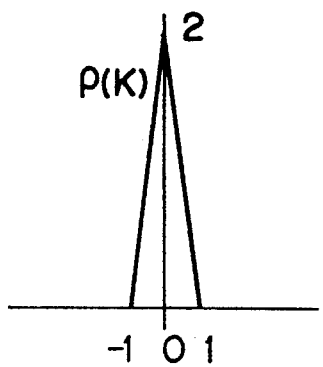

Incidentally, the sequences noted below are Barker sequences having the same autocorrelation function shown in FIG. 3(b).

$$a1_j = + + + - - + -$$

$$a2_j = + - + + - - -$$

Figure 36A:
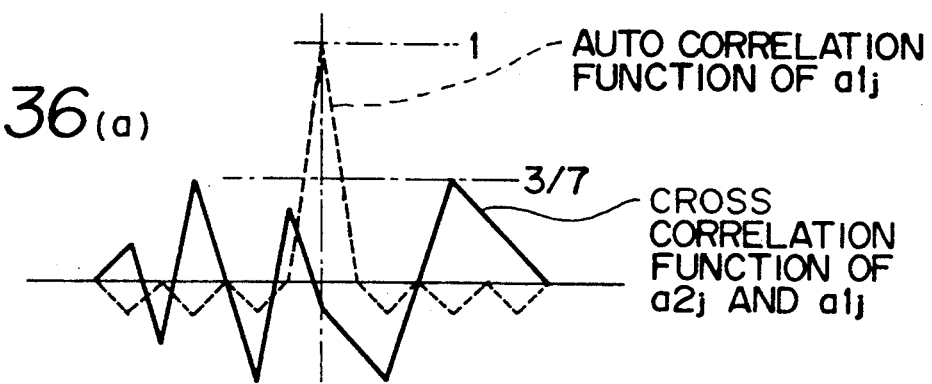
FIGS. 36(a) and (b) show another advantageous effect of FIG. 31.
Figure 36B:
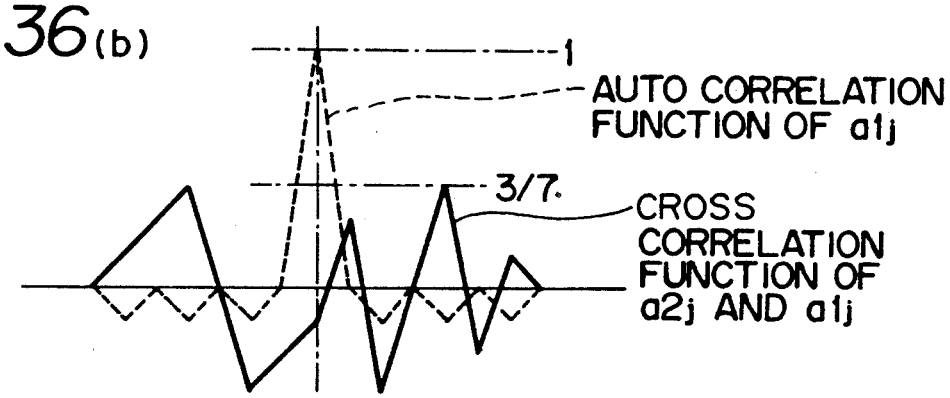

FIG. 36 are the results of the correlation operations of the sequences $a1_j$ and $a2_j$ wherein FIG. 36(a) is the result of the operation for the sequence $a1_j$ with using the sequence $a2_j$ as the reference signal and FIG. 36(b) is the result of the operation for the sequence $a2_j$ with using the sequence $a1_j$ as the reference signal. As seen from these drawings, there will be no high peaks in the correlation between the different sequences even though they have the same autocorrelation function.

Now, it is reminded that the problem regarding the reverberation echo is a phenomenon that the ultrasonic signal generated in the previous transmission cycle causes interference. An operation of the ultrasonic inspecting apparatus is explained in which the above problem is solved. As seen from FIG. 36, the reverberation echo coded at the previous transmission is reduced by approximately 7 dB if a different sequence having the same autocorrelation function as above is generated by switching over per each of the transmission repetition with the synchronous signal from the synchronous signal generator TG and also the reference wave form of the reference wave form memory 207 is changed in accordance with the sequence of the transmission wave form.

Further, a flaw detection signal is enhanced and an S/N ratio is improved as explained above if a signal having provide a frequency response characteristic along an ultrasonic wave passage is set to a reference signal.

Incidentally, Barker sequence explained hereinabove surely possesses a sharp autocorrelation function: however, as seen from FIG. 3(b), it has sidelobe levels of 1/n. Therefore, there is a problem when a flaw echo adjacent a large bottom echo is to be classified in a vertical flaw detection system. In such a case as above, it is possible to cope with the problem of sidelobes with using a complementary sequence. It has been considered that there is only a way of using the sum of two sequences in order to cancel sidelobes: however, the inventors have discovered that the sum of more than four kinds of autocorrelation functions such as $\rho_{aa}(k)$, $\rho_{bb}(k)$, $\rho_{cc}(k)$ and $\rho_{dd}(k)$, i.e.

$$\rho(k) = \rho_{aa}(k) + \rho_{bb}(k) + \rho_{cc}(k) + \rho_{dd}(k) \tag{201}$$

becomes zero at all points other than at k=0. Since this matter has not been referred to in the literature available heretofore, these sequences $\{a_j\}$, $\{b_j\}$, $\{c_j\}$ and $\{d_j\}$ are referred to, in this description, as multiple complementary sequence or n-complementary sequence. FIG. 37(a) shows an example of multiple complementary sequence wherein n=4 and indicates signals of binary sequence expressed by the equation (202).

$$\{a_j\} = - - + +$$

$$\{b_j\} = - + - +$$

$$\{c_j\} = - + + -$$

$$\{d_j\} = + + + + \tag{202}$$

FIG. 37(b) shows autocorrelation functions of $\{a_j\}$, $\{b_j\}$, $\{c_j\}$ and $\{d_j\}$ calculated based on the equation (3) in the range of $-n \leq k \leq n$.

FIG. 37(c) shows the sum $\rho(k)$ of the respective autocorrelation functions calculated based on the equation (201). As seen from this drawing, it is theoretically possible to make the levels of range sidelobes zero in the multiple complementary sequence. This is explained more elaborately later.

Figure 21:
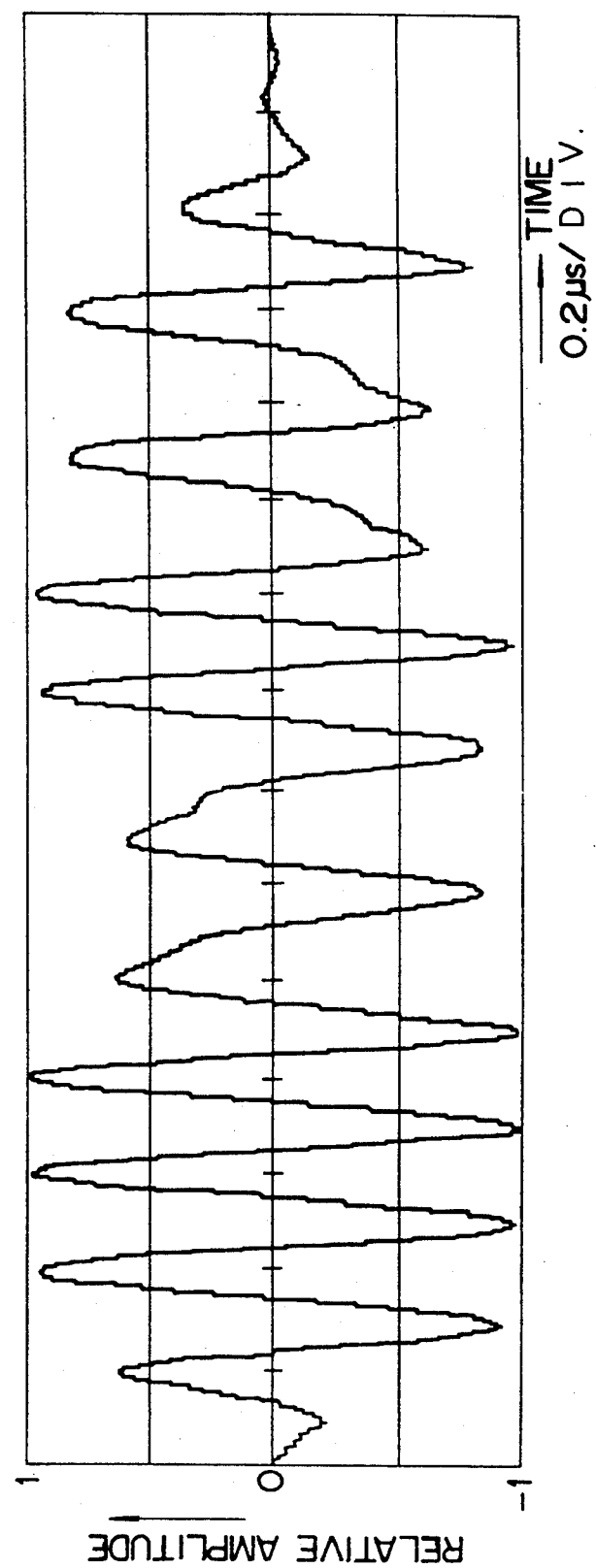
FIGS. 21(a) and (b) show a wave form of another reflection echo in the first embodiment of the present invention.
Figure 22:
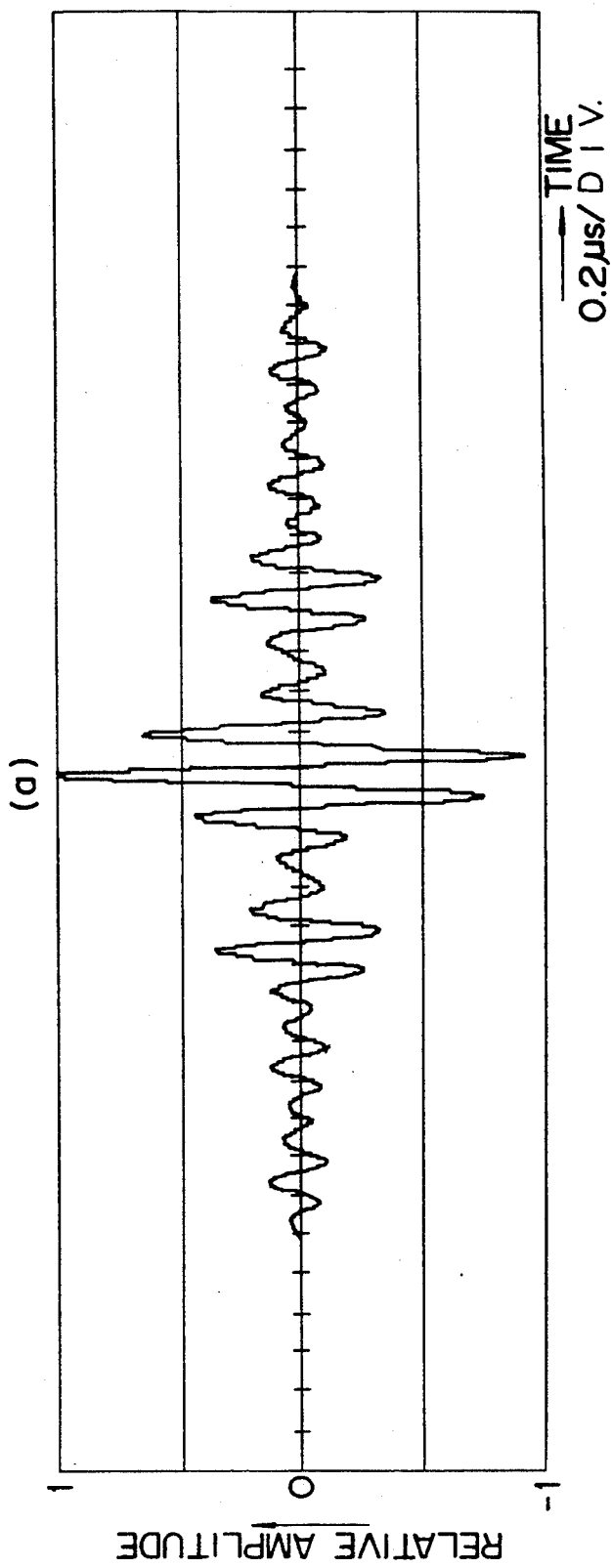
FIGS. 22(a) and (b) show a wave form of another correlation operation results in the first embodiment of the present invention.
Figure 22:
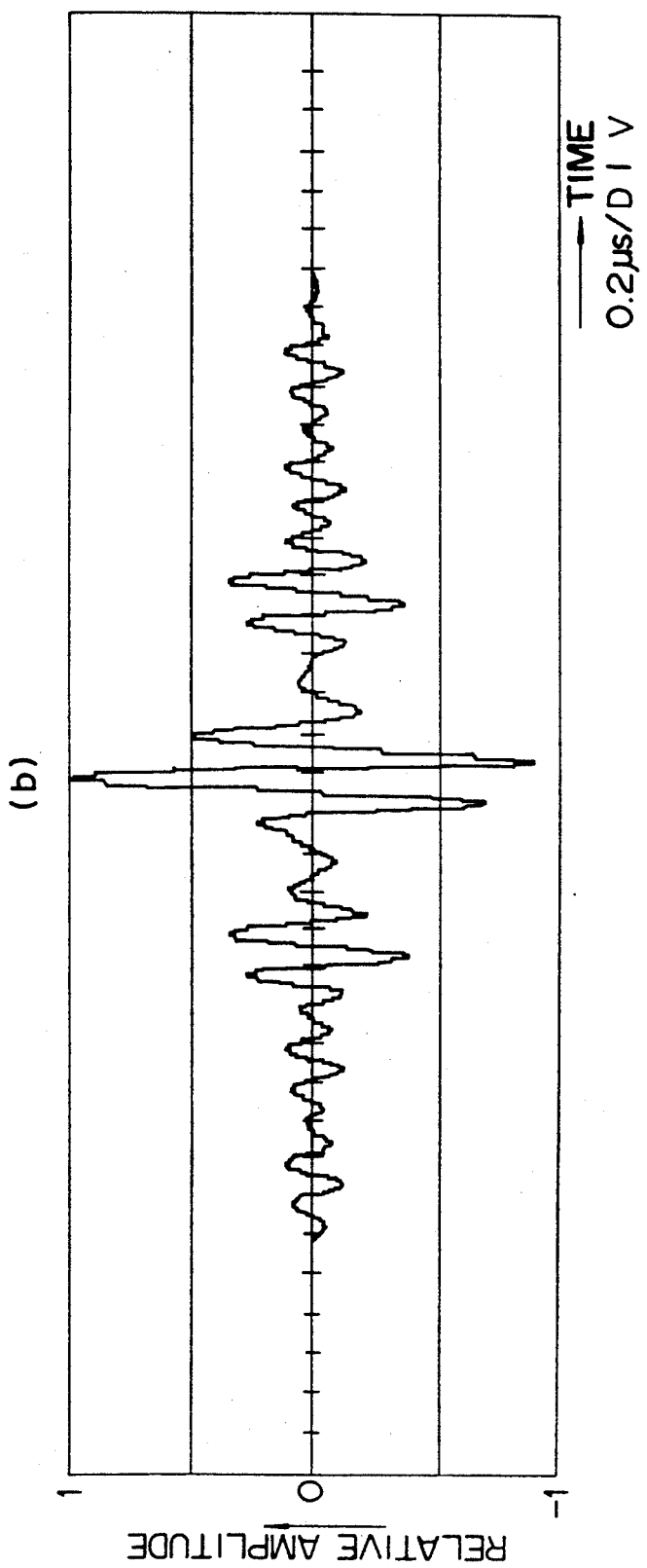
Figure 38:
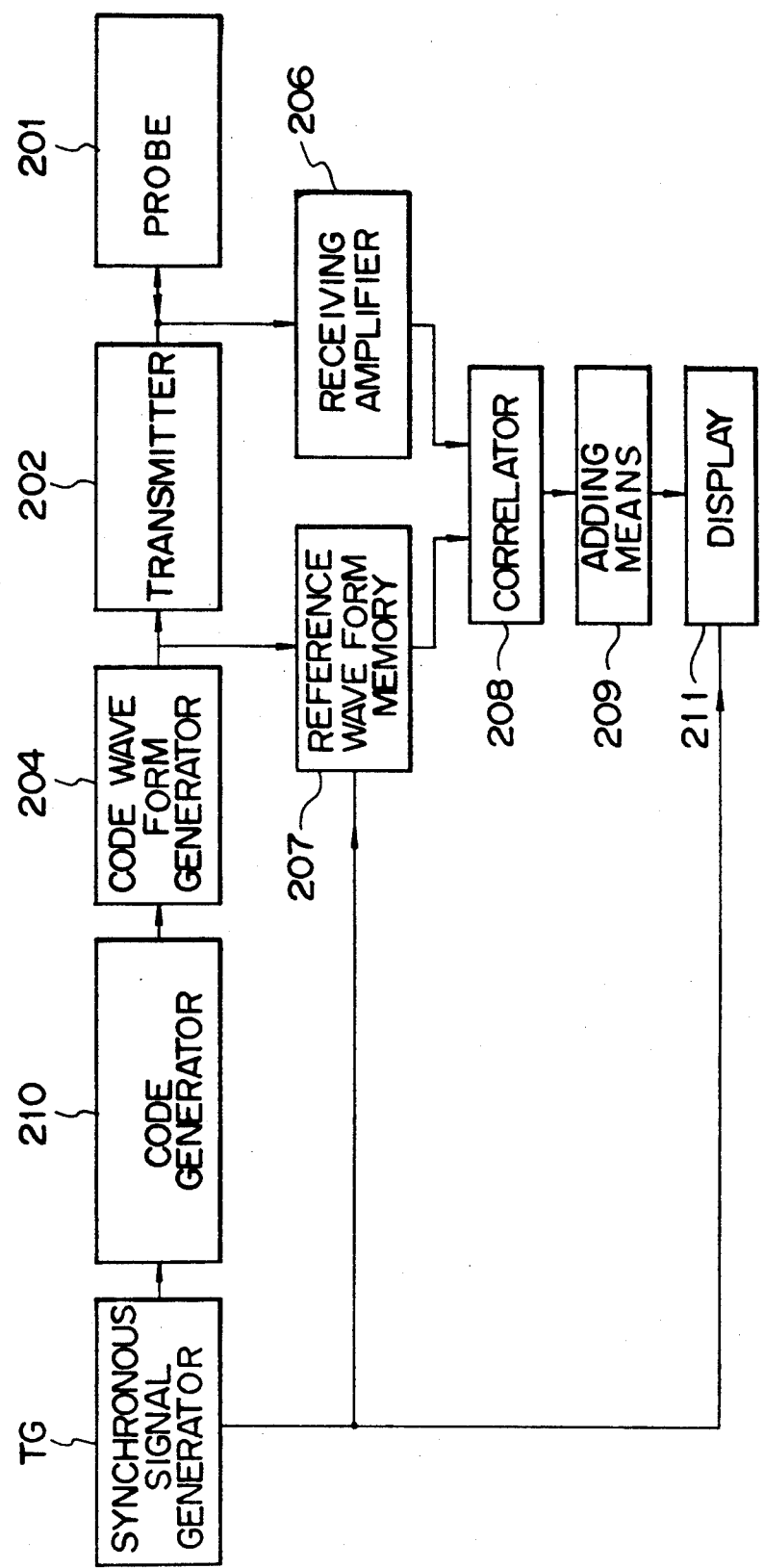

FIG. 38 shows a fifth embodiment representing the above idea wherein 201, 202, 204, 206, 207, 208, TG and 211 are the same as those shown in FIG. 21, 210 is a code generator connected to the synchronous signal generator TG and adapted to output a finite binary sequence having positive and negative values at every T" time and connected to the code wave form generator 203. The code generator 210 outputs the sequence by sequentially changing the respective sequences of the complementary sequence or multiple complementary sequence with a transmission signal repeating cycle and 209 is an adding means for summing correlation wave forms derived from the respective sequences.

Figure 39:
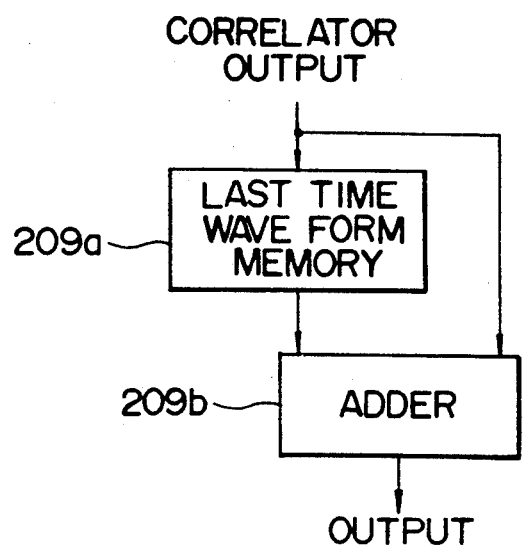

FIG. 39 is a drawing for explaining an operation of the adding means 209 wherein it is intended in this instance to explain the adder for the complementary sequence. 209a is a last time wave form memory constructed by utilizing, for example, a shift register, and 209b is an adder for summing the outputs of the last time wave form memory and the correlator 208.

The operation of the fifth embodiment is almost the same as that explained in connection with FIG. 31 and, therefore, the operation is explained for the portions different from those in FIG. 31.

A sequence generated at the code generator 210 is transmitted, transformed as a transmission signal by the coded wave form generator 204, to the probe 201 though the transmitter 202. An ultrasonic wave signal reflected within a specimen is amplified at the receiving signal amplifier 206 and its correlation operation with the output of the reference wave form memory 207 is performed by the correlator 208. The result of the operation is stored in order in the last time wave form memory 209a constructed by utilizing, for example, a shift register or the like and the last time wave form after the correlation operation is outputted synchronously with the instant wave form. If a sequence used in the instant transmission signal is $\{a_j\}$, then the last time transmission signal is, in the case of the complementary sequence, the signal coded by $\{b_j\}$. Therefore, the adder performs the operation expressed in the equation (6). Accordingly, the signal outputted from the adder 206 is a signal wherein range sidelobes are improved. Incidentally, in the case of n-complementary sequence, a necessary number of last time wave form memories 209a are prepared and their respective outputs are summed by the adder 209b.

The use of a complementary sequence of n-complementary sequence having the above described features surely improves the range sidelobes as well as provides further characteristic advantage. For example, if an outside electric noise of a quite large level while having no-correlation with the sequence is intermixed, the noise may be reduced to the level determined by the sequence length n, but, in some case, an S/N ratio at an enough level may not be assured. In such case, if the advantageous feature of utilizing the summed result with respect to a number of sequences is employed, it achieves further effects that the outcoming electric noise can be further reduced to the level determined by 2 in the case of using a complementary sequence in flaw detection and to the level determined by 4 in the case of using the n-complementary sequence shown in FIG. 37, as well as that the range sidelobes are improved. Incidentally, while the similar effects can be expected with a mere averaging process, the use of sequences with different autocorrelation functions at each of repetitions theoretically achieves further advantageous effect in that it can also reduce the outcoming electric noise having a periodicity feature.

Figure 40A:
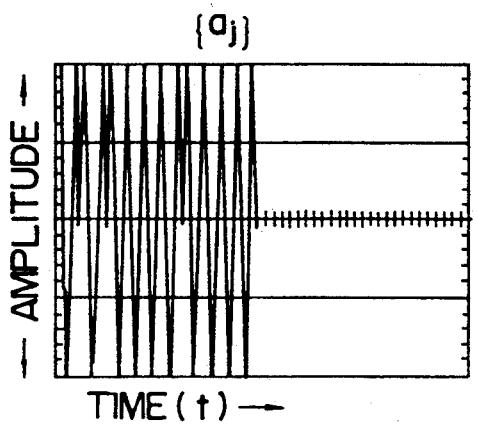
Figure 40B:
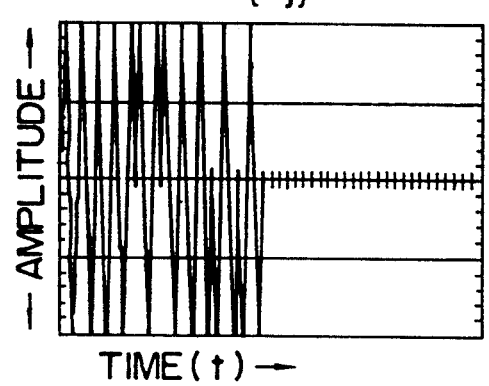
Figure 42A:
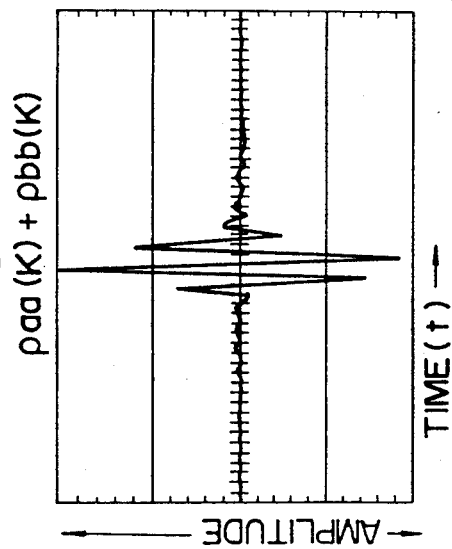
Figure 42B:
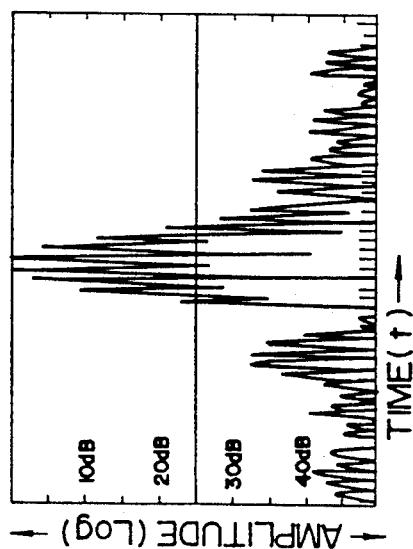
Figure 42C:
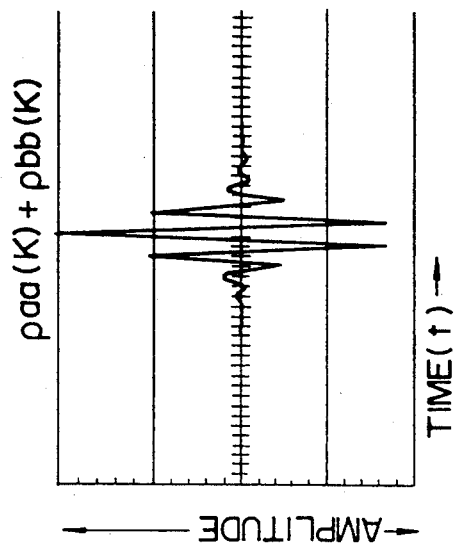
Figure 42D:
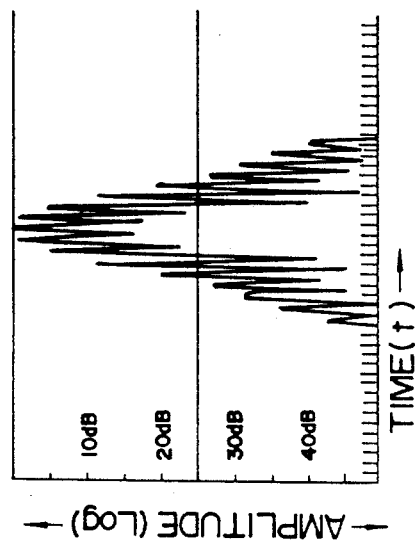

Further, in the present invention explained above, if a reference signal is arranged so that it bears the frequency response feature of a passage through which the ultrasonic wave propagates, a flaw detection signal is enhanced and an S/N ratio is improved as explained hereinabove. However, arrangement for providing the frequency response feature of the ultrasonic wave propagating passage to the complementary sequence or n-complementary sequence achieves further advantageous effect. FIGS. 40(a) and (b) show transmission signals in the case where a complementary sequence with n=8 is used, FIGS. 41(a) and (b) show receiving signals of bottom echoes from a plate having thickness of 25 mm by using transmission signals of FIGS. 40, FIGS. 42(a) and (b) show the sum of the correlation processed wave forms of the receiving signals shown in FIGS. 41 with transmission signals shown in FIG. 40 as reference signals in linear and logarithmic scales, respectively, FIGS. 42(c) and (d) show the sum of the correlation processed wave forms in linear and logarithmic scales, respectively, which are obtained by the receiving wave forms as shown in FIG. 41, taken under the similar conditions with using the transmission signals shown in FIGS. 41 and reference signals. Upon comparing the above experimental results, it is noted that the range sidelobes are improved by nearly 17 dB if a reference signal is arranged so that it bears a frequency response characteristic of a passage through which ultrasonic waves propagate, that is, the transmission signals propagate.

The present invention achieves, as explained above, improvements of S/N ratios by enhancement of flaw detection signals and/or reduction of noises and unintended signals received from outside. Now, the present invention is further reviewed for the case where a specimen exhibiting large attenuation of an ultrasonic wave, such as stainless steel and/or cast iron is employed.

The graph shown in FIG. 43 illustrates a frequency response characteristic A of the ultrasonic probe, a frequency response characteristic B of the specimen and a combined frequency response characteristic C. In the foregoing, explanation has been made that an energy transmitting efficiency is made maximum where the transmission signal generated at the coded wave form generator 204 is matched, as shown in FIG. 43, to the center frequency $f_p$ of the probe. However, in the instant example where the attenuation within the specimen is to be considered, there may be case that the frequencies providing the maximum efficiency are not matched depending on the attenuation (frequency response characteristic) of the specimen to the central frequency of the probe. In such a case as above, energy of the transmission signal can be more efficiently directed to the body of the specimen to improve an S/N ratio of the receiving signal if a frequency of the transmission signal generated at the coded wave form generator 204 is not matched with the central frequency ($f_p$) of the probe but is matched with the central frequency ($f_o$) of the frequency response characteristic of the combination of the probe and specimen.

Figure 5:
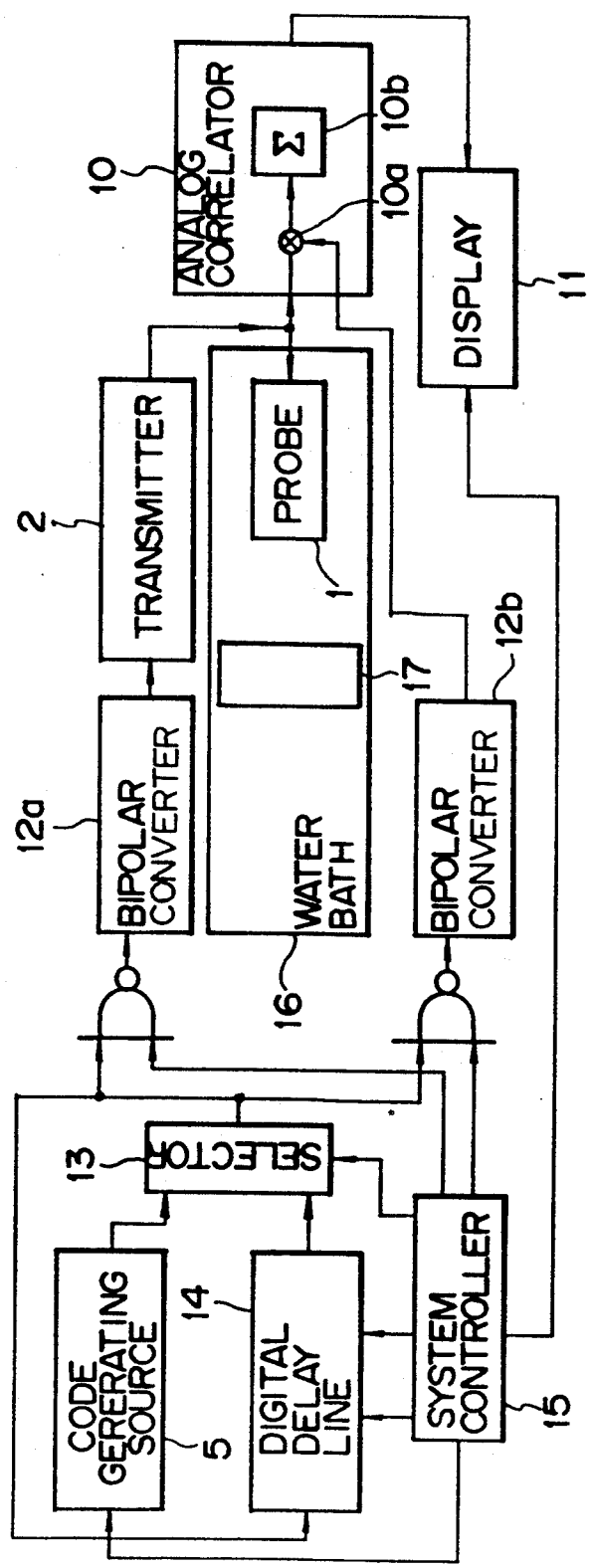
FIG. 5 shows a conventional ultrasonic inspecting apparatus having a function of correlation operation.
Figure 6:
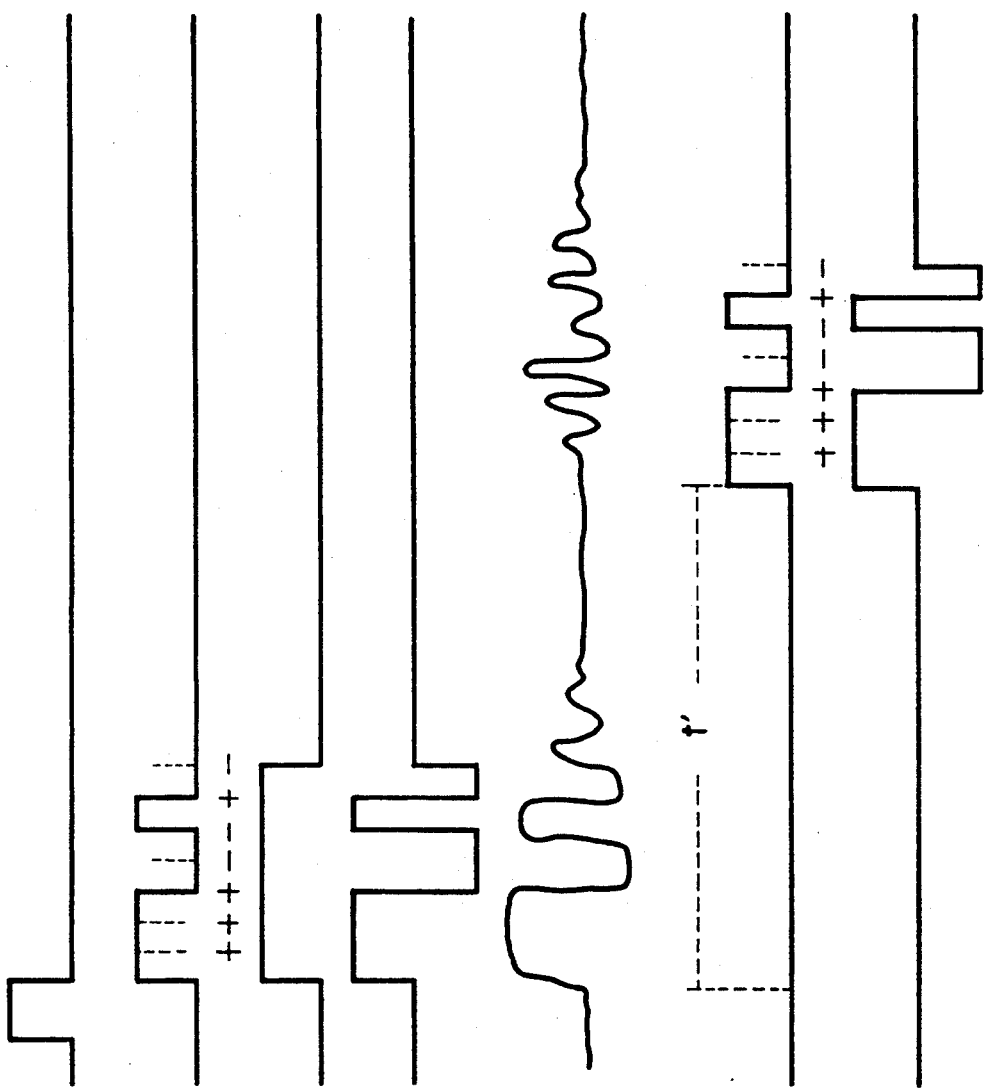
FIG. 6 are drawings for explaining the operation of FIG. 5.
Figure 7:
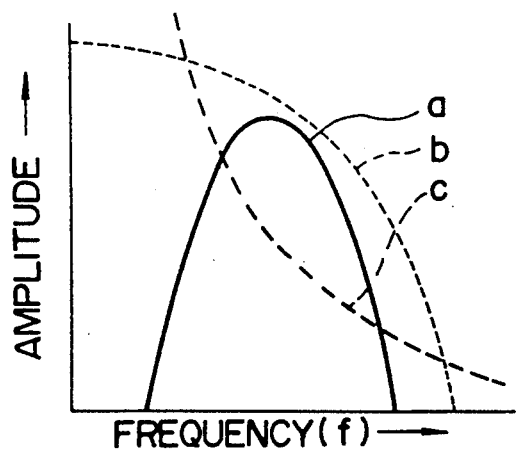
FIG. 7 is a drawing for explaining a problem of prior art.
Figure 8:
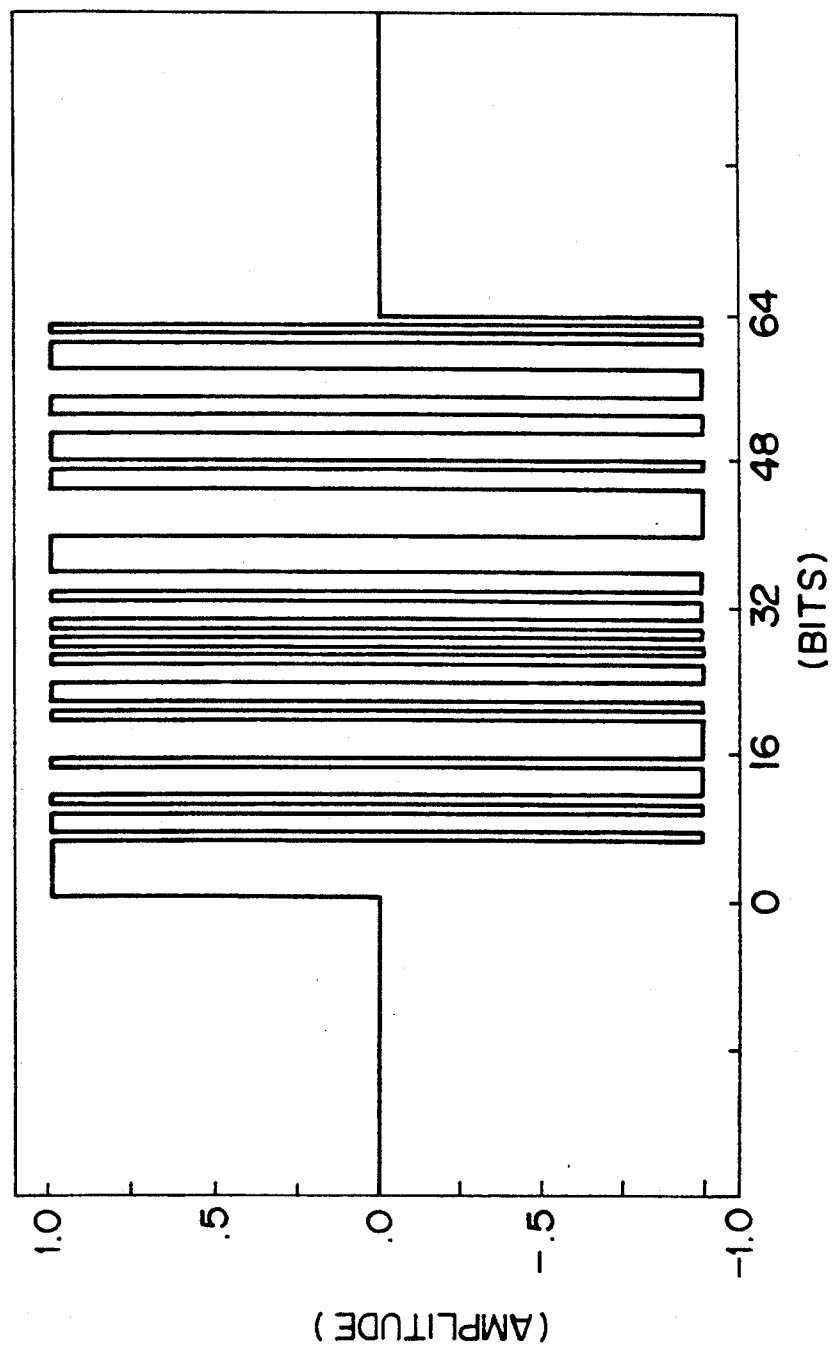
FIG. 8 shows a wave form of a transmission signal in a conventional ultrasonic non-destructive inspecting apparatus.
Figure 9:
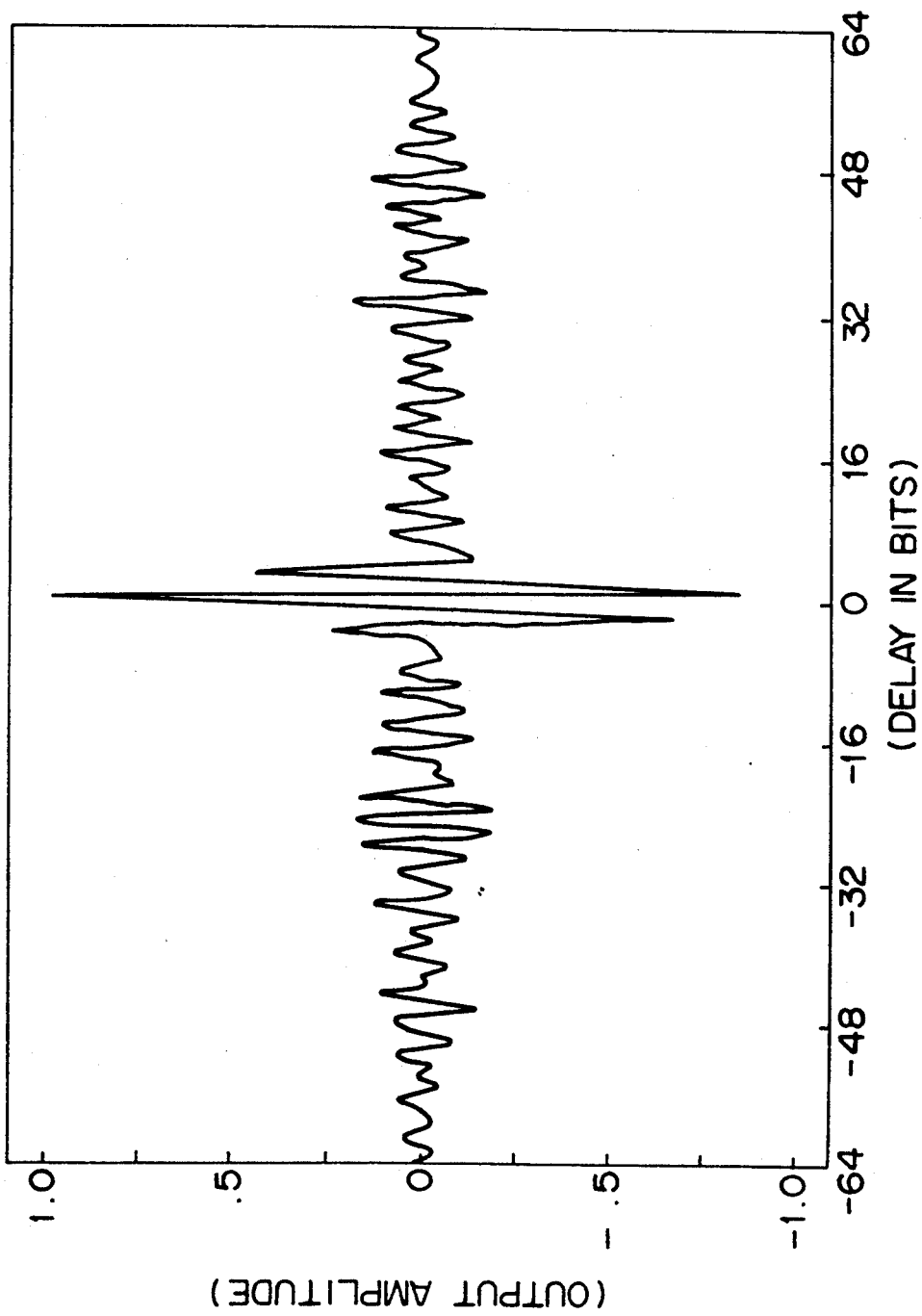
FIG. 9 shows a wave form of a compressed pulse in a conventional ultrasonic non-destructive inspecting apparatus.
Figure 10:
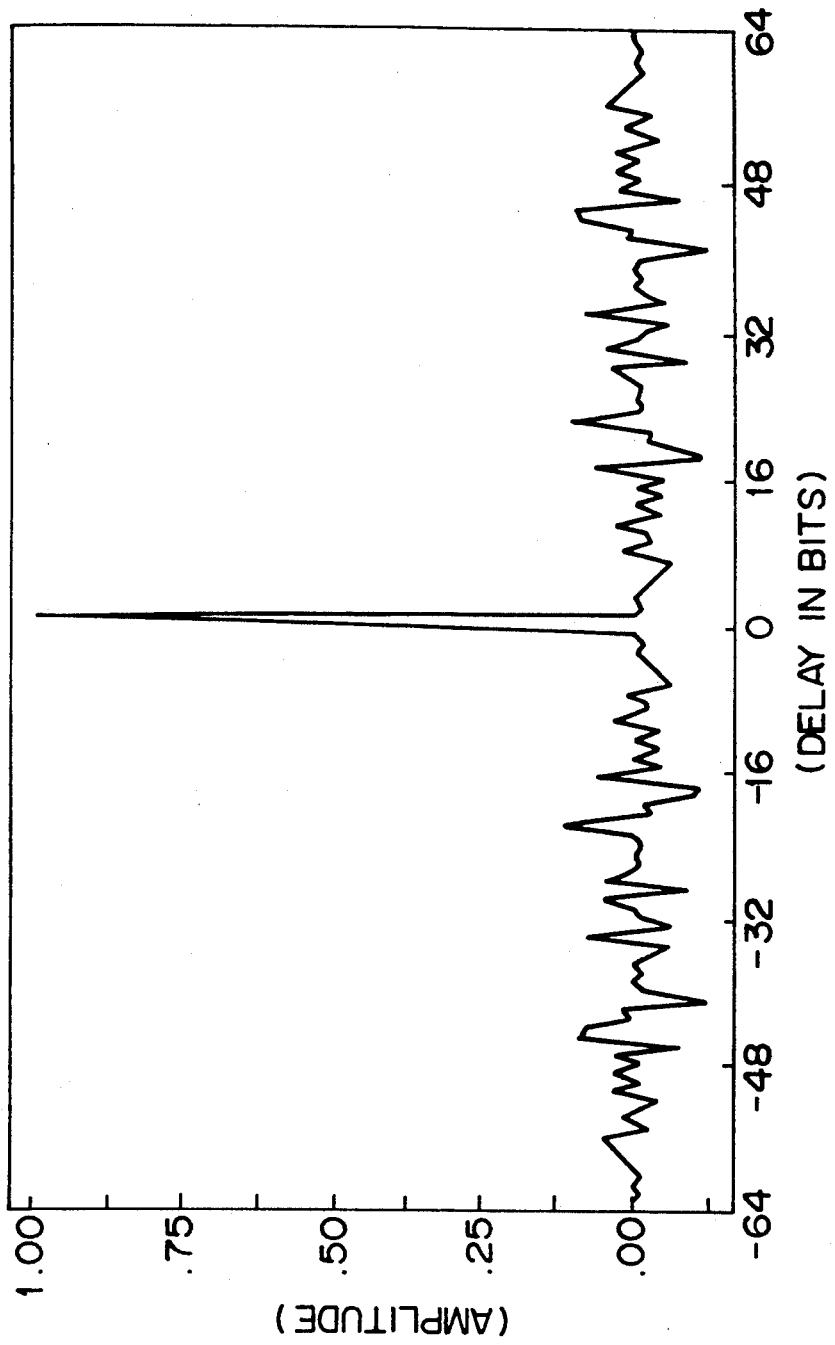
FIG. 10 is a wave form of a finite length sequence autocorrelation function in a conventional ultrasonic non-destructive inspecting apparatus.
Figure 11:
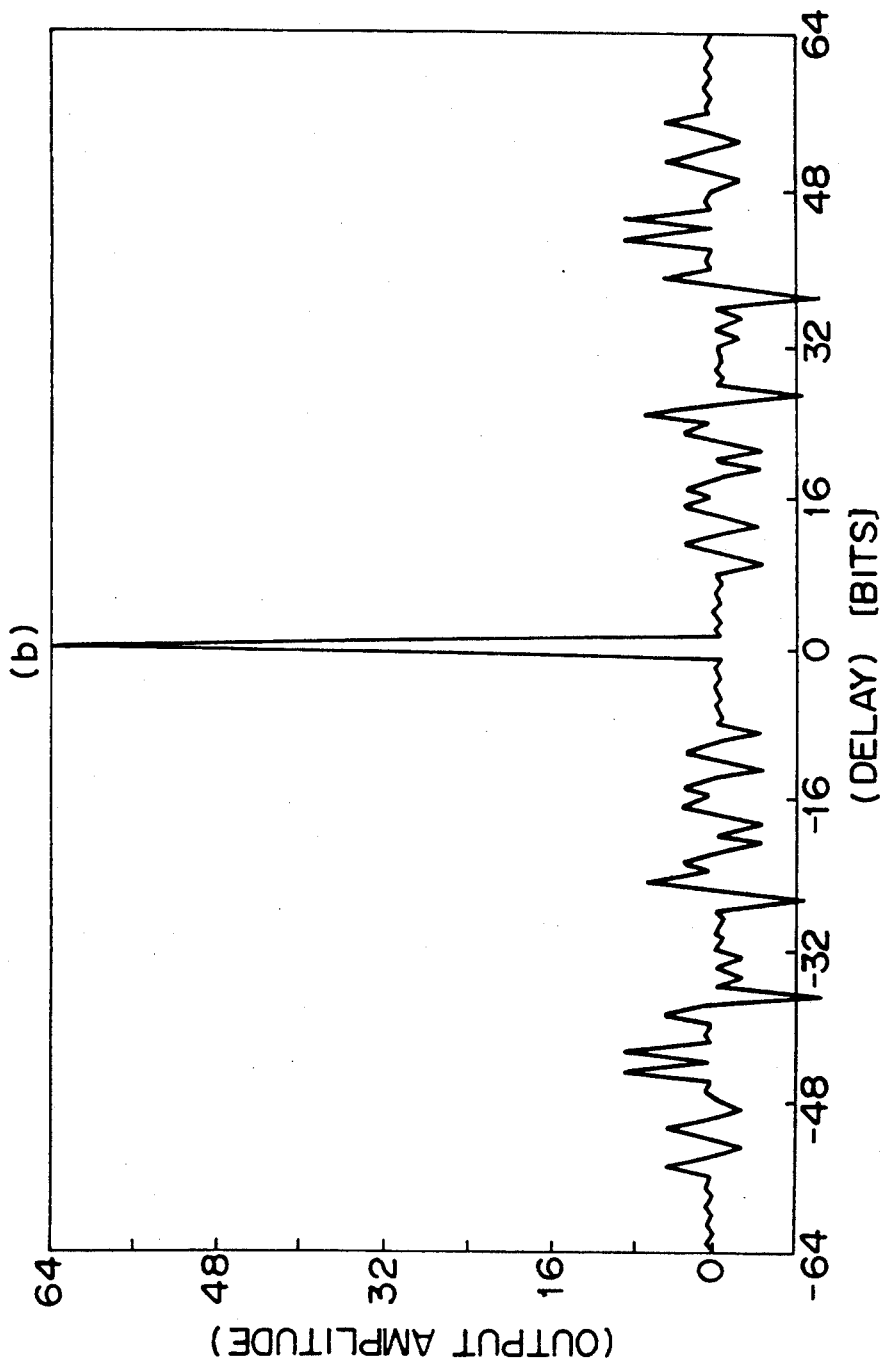
FIGS. 11(a) and (b) are wave forms of a complementary sequence autocorrelation function in a conventional ultrasonic non-destructive inspecting apparatus.
Figure 12:
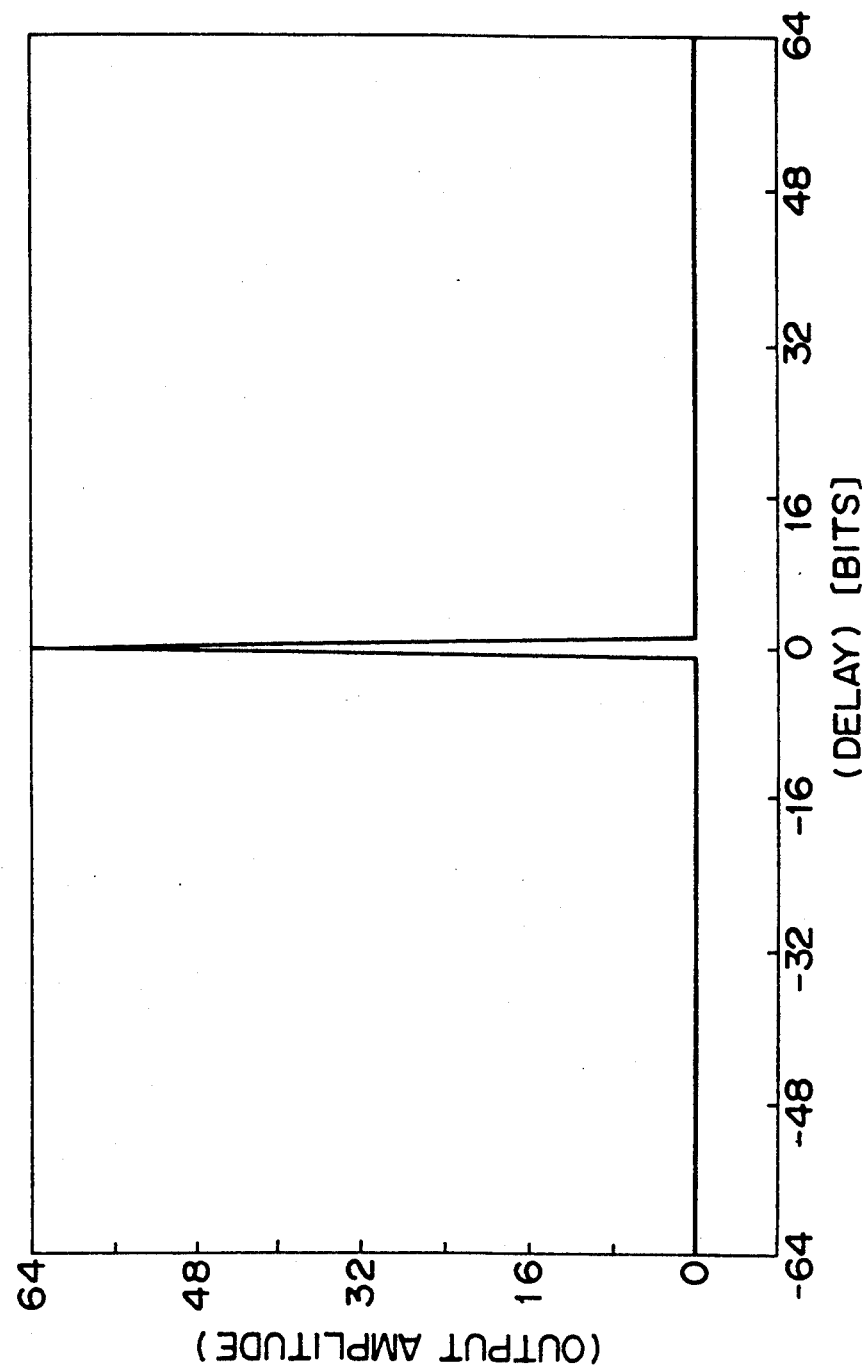
FIG. 12 shows a summing result of autocorrelation functions of a complementary sequence in a conventional ultrasonic non-destructive inspecting apparatus.
Figure 13B:
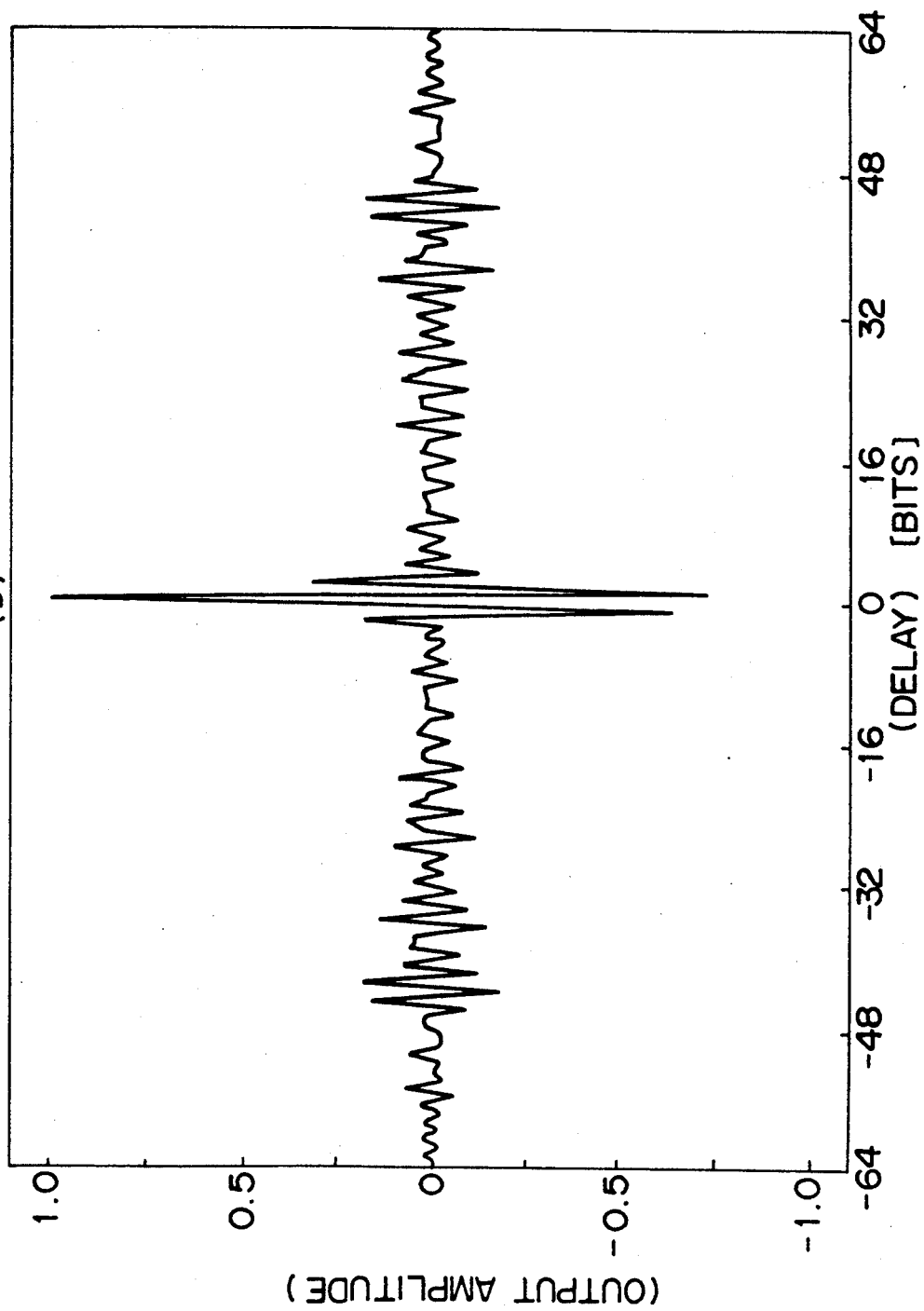
FIGS. 13(a) and (b) show a compressed pulse in a conventional ultrasonic non-destructive inspecting apparatus.

Further example of the present invention is explained as a sixth embodiment shown in FIG. 44 where a multiple complementary sequence is employed so as to cancel range sidelobes. The term "multiple complementary sequence" or "n-complementary sequence" used herein means that, compared to an ordinary complementary sequence comprising two sequences each having the same length, it comprises even number (4 or more than 4) of sequences each having the same length and a range sidelobe completely disappears when the respective autocorrelation functions of the sequences are summed. We have discovered such sequences exist. In FIG. 44, an ultrasonic probe 301 and a display 311 are the same as that shown in FIG. 5. Thus, this embodiment comprises the same components as those employed in prior art and others, namely an amplitude coding transmission signal generator 305A, a correlator 310A connected to the amplitude coding transmission signal generator 305A and the ultrasonic probe 301 and an adder 310B including a memory means connected, at its input side, to the correlator 310A and, at its output side, to the display 311.

Incidentally, the ultrasonic probe 301 is also connected to the amplitude coding transmission signal generator 305A and contacted with the specimen S.

Figure 45:
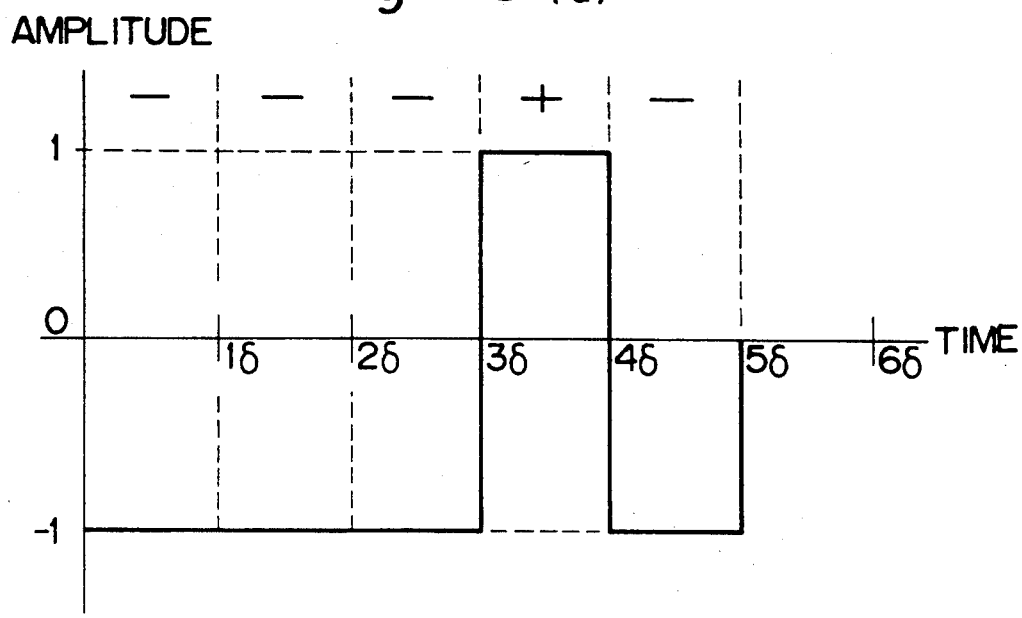
FIGS. 45(a), (b), (c) and (d) show a wave form of a transmission signal in the sixth embodiment of the present invention.
Figure 45:
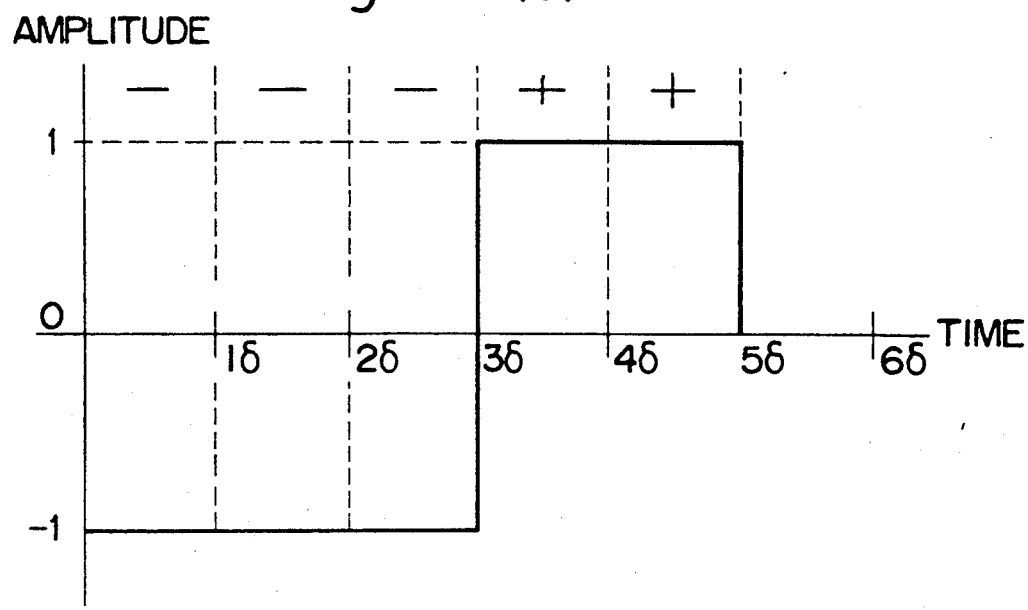
Figure 45C:
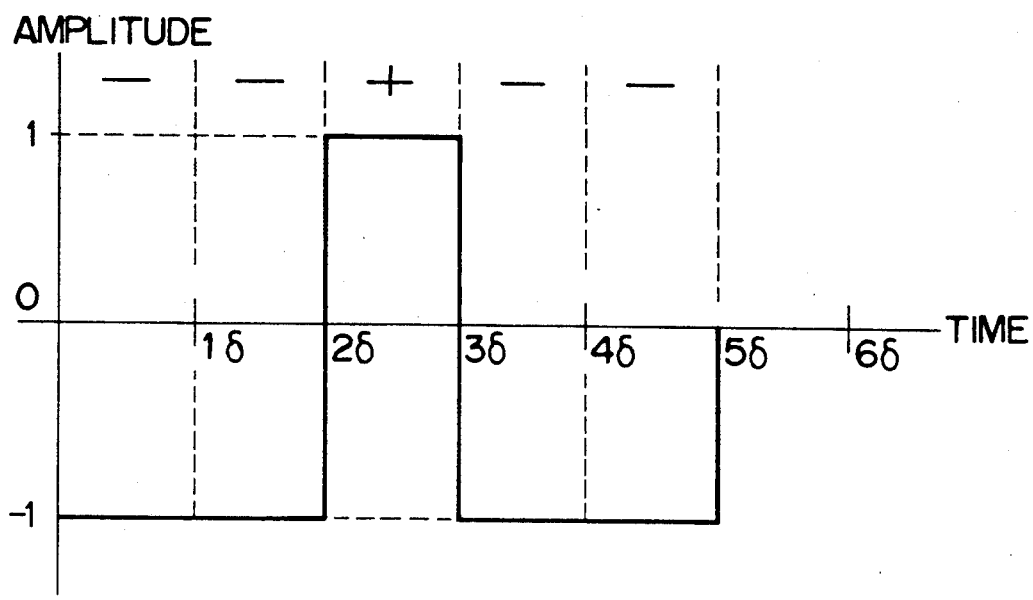
Figure 45D:
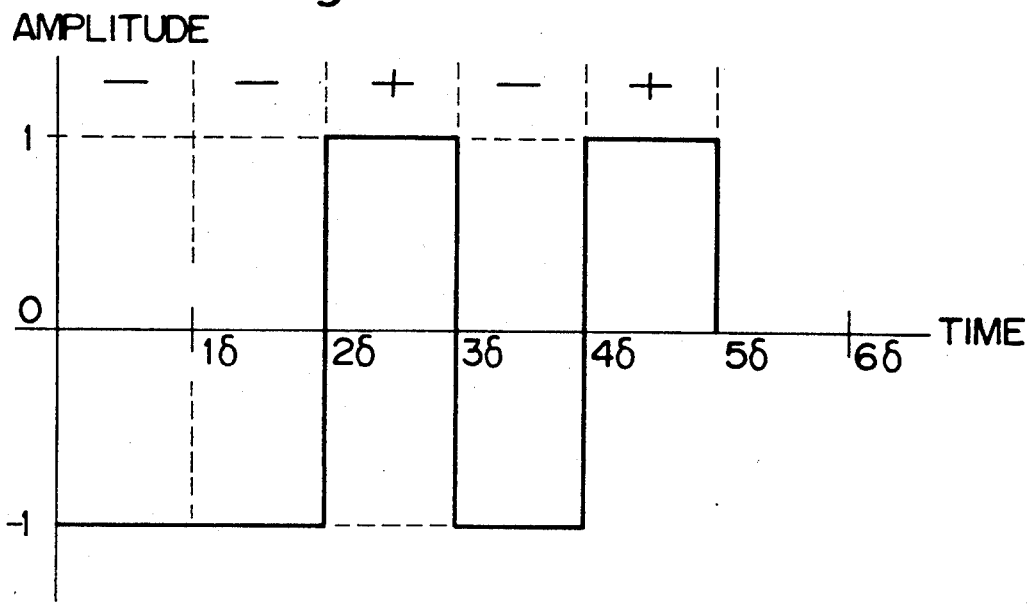
Figure 46:
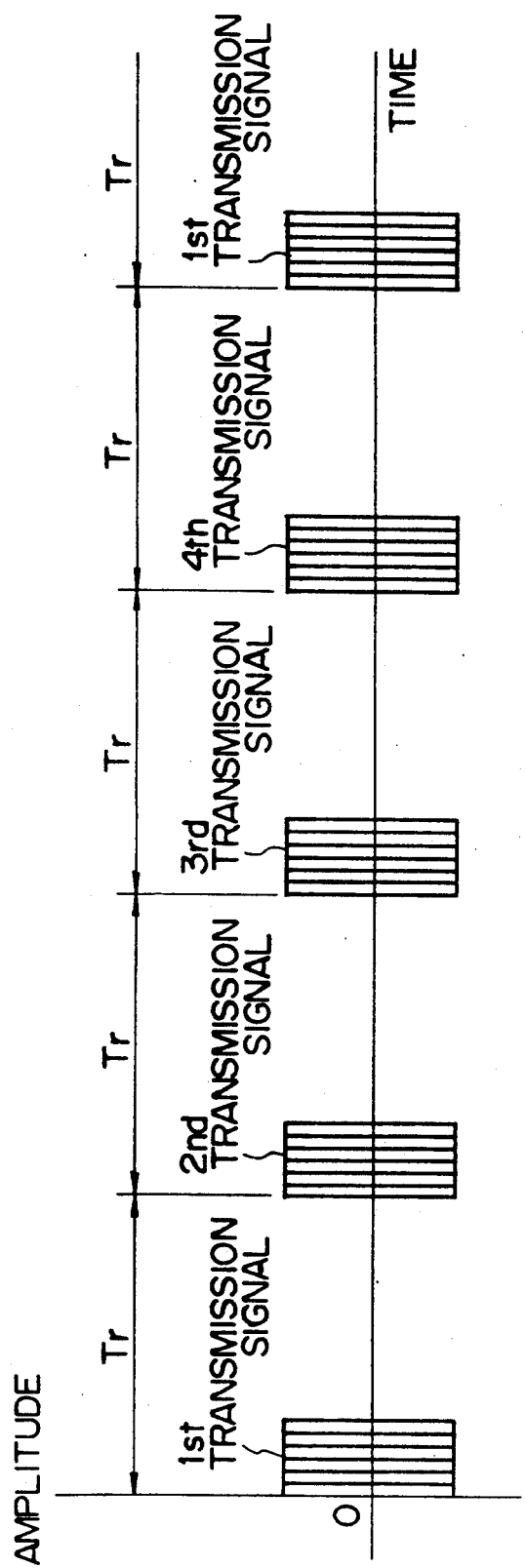
FIG. 46 shows four transmission signals in the sixth embodiment of the present invention.
Figure 47:
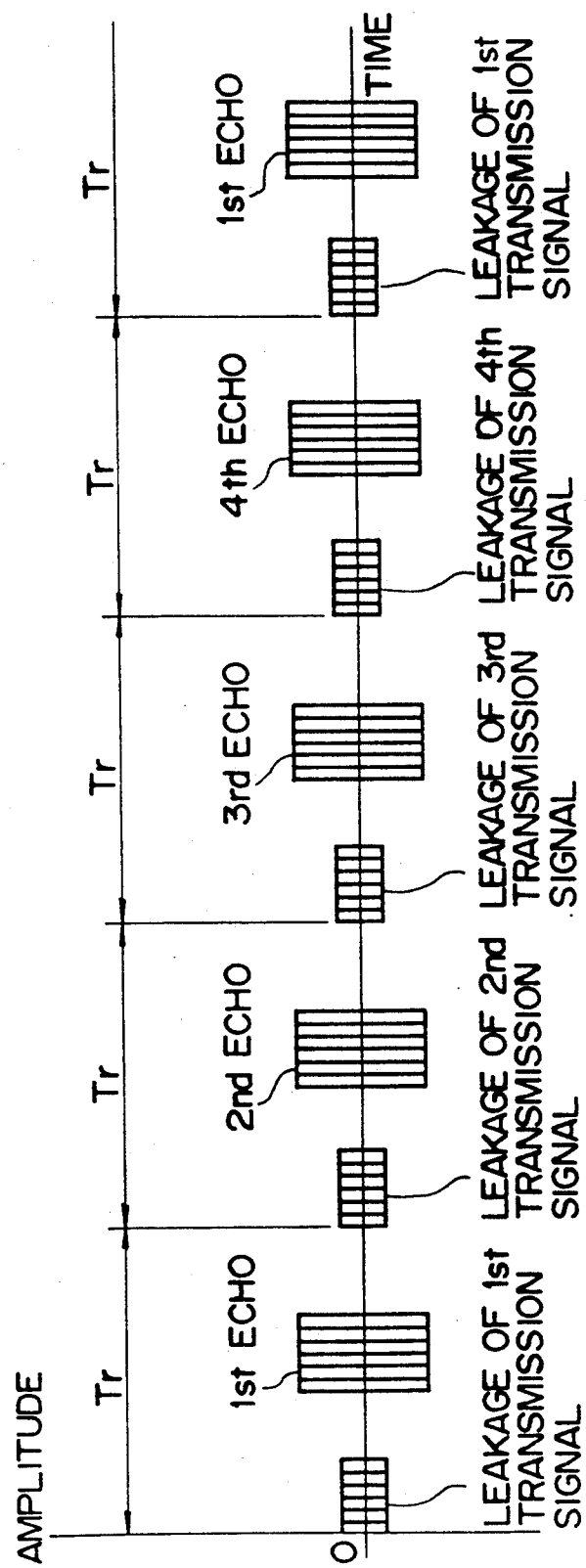
FIG. 47 shows four echoes in the sixth embodiment of the present invention.
Figure 48:
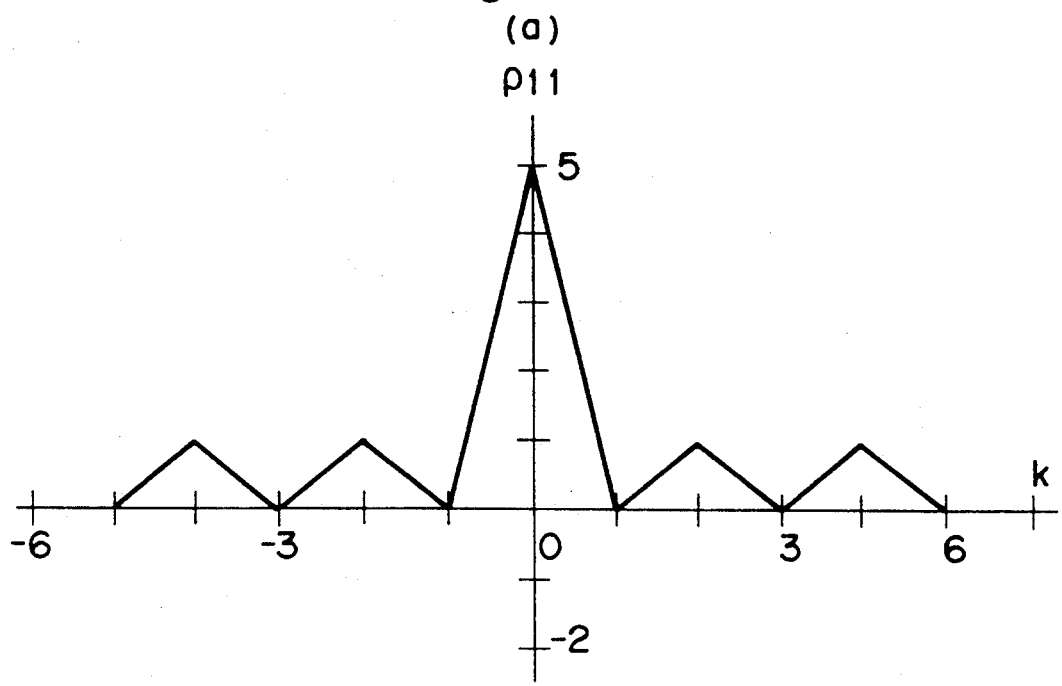
FIGS. 48(a), (b), (c) and (d) show operation results of autocorrelation functions of 1st, 2nd, 3rd and 4th sequences in the sixth embodiment of the present invention.
Figure 48:
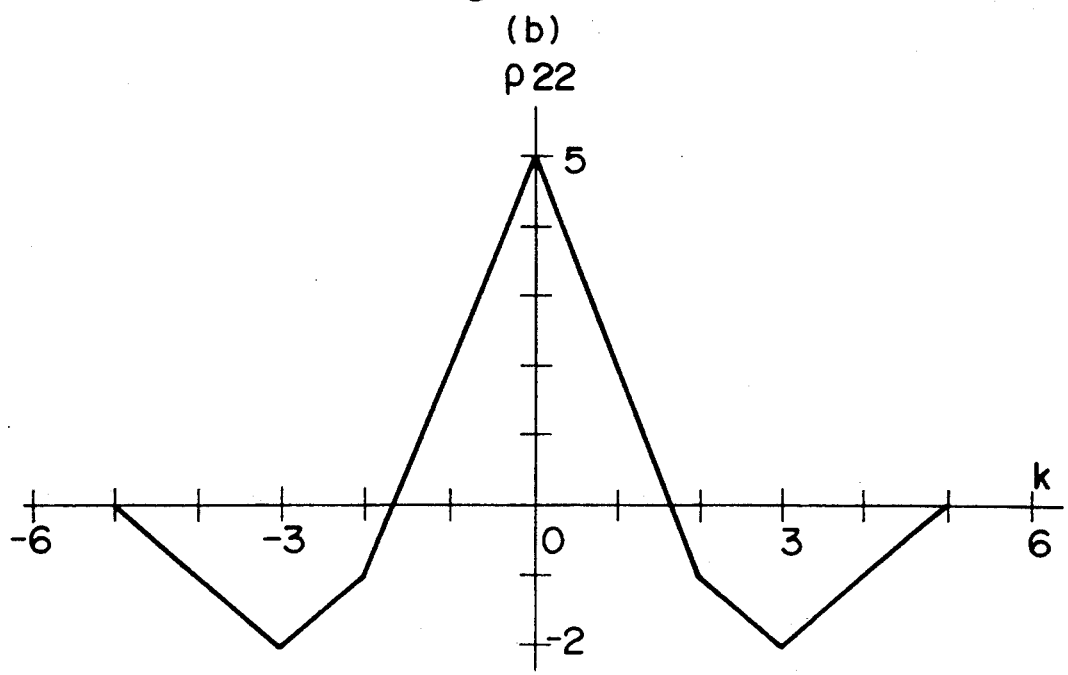
Figure 48:
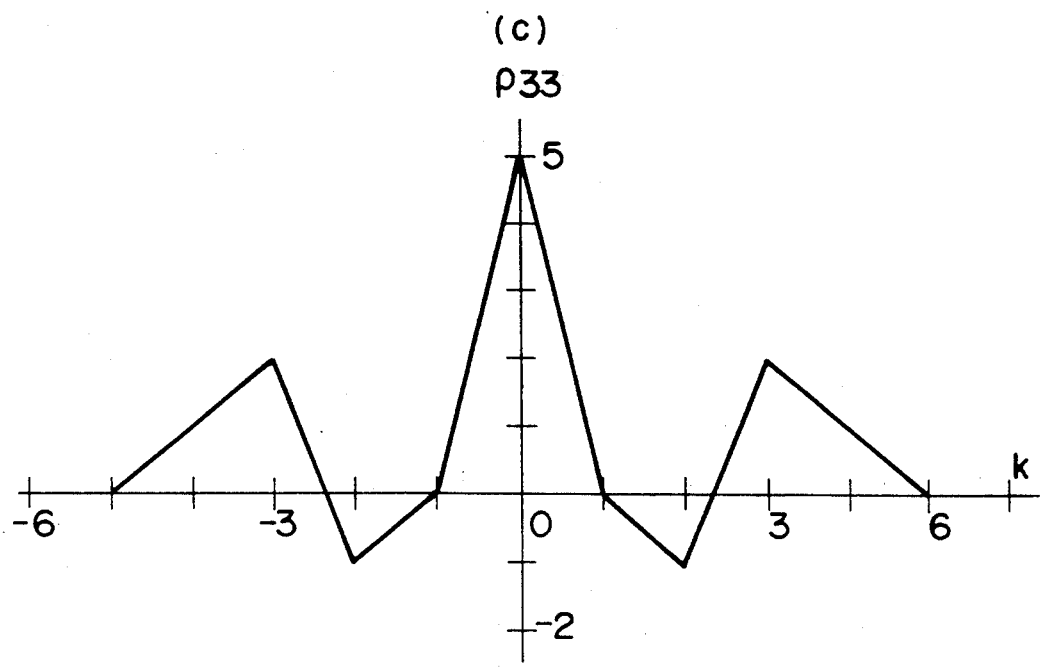
Figure 48:
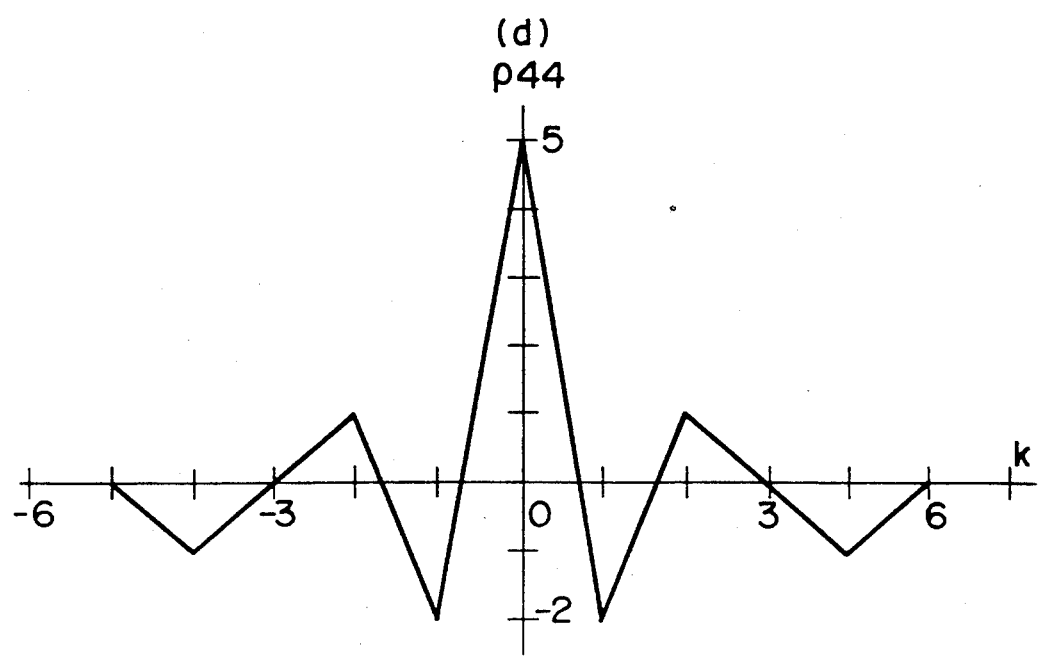

An operation of the sixth embodiment is explained referring to FIGS. 45, 46 and 47.

The transmission signals shown in FIGS. 45(a)-(d) are those obtained by coding their amplitudes in a manner similar to that in prior art. However, sequences used for the coding are constituents of a multiple complementary sequence comprising four sequences each having a length of 5. The four sequences are referred to as 1st, 2nd, 3rd and 4th sequences and they are as follows.

1st sequence (−, −, −, +, −);
2nd sequence (−, −, −, +, +);
3rd sequence (−, −, +, −, −); and
4th sequence (−, −, +, −, +).

In order to facilitate understanding the relationship between these sequences and amplitude coding, the signs of the above sequences are inserted into FIGS. 45(a)—(d).

Hereinafter, the transmission signals shown in FIGS. 45(a)-(d) are also given numbers corresponding to the numbers of the above sequences and they are referred to as 1st, 2nd, 3rd and 4th transmission signals, respectively.

The amplitude coding transmission signal generator 305A generates the above four transmission signals in turn with a certain fixed repetition period Tr as shown in FIG. 46 and transmits them to the ultrasonic probe 301.

The ultrasonic probe 301 is driven sequentially by the four transmission signals and transmits ultrasonic waves into the body of the specimen S. Then echoes reflected at flaws, etc. within the specimen S are received by the probe 301. These echoes are transmitted to the correlator 301A.

Echoes obtained by driving the ultrasonic probe 301 with the 1st, 2nd, 3rd and 4th transmission signals are referred to, as shown in FIG. 47, as a 1st, 2nd, 3rd and 4th echoes, respectively. Incidentally, since transmission signals are partly leaked to the receiving side circuit (the side of the correlator 310A), FIG. 47 also illustrates such situation.

The correlator 310A compresses the "it" th echo ($i=1, 2, 3, 4$) by performing correlation process thereon with using the "i"th transmission signal. The compressed pulse obtained by compressing the "i" th echo is referred to as the "i"th compressed pulse. The 1st, 2nd, 3rd and 4th compressed pulses are sequentially transmitted to the adder 310B.

The adder 310B stores the 1st, 2nd and 3rd compressed pulses in its memory means until the 4th compressed pulse is transmitted thereto and, at the time when the 4th compressed pulse is transmitted, it sums the 1st, 2nd, 3rd and 4th compressed pulses. Hereinafter, the result of the summing operation is referred to as a composite compressed pulse. This composite compressed pulse is transmitted to the display 311 from the adder 310B.

Incidentally, in the present invention, relative levels of range sidelobes in the composite compressed pulse is an object of concern. Therefore, it is possible to transmit the four compressed pulses to the display 311 from the adder 310B either by merely summing the four compressed pulses as above or by summing and averaging the four compressed pulses.

In the display 311, the composite compressed pulse is displayed in a manner similar to that of prior art.

Effects and advantages of the sixth embodiment according to the present invention are explained referring to FIGS. 48, 49, 50, 51, 52, 53, 54 and 55.

An autocorrelation function was calculated based on the following equation which is modified from the equation (17.4) shown on page 475 of Reference D.

$$\rho_{aa}(k) = \Sigma a_{j+k} a_j \quad (301)$$

(summing range: $0 \sim n-1$).

On the above equation, $\rho_{aa}$ is an autocorrelation function of a sequence "a" and "k" is an integer, $a_j$ indicates a "j" th element ($+1$ or $-1$) of the sequence "a" and "n" is a length of the sequence. For example, if the sequence "a" is the 1st sequence $(-, -, -, +, -)$ discussed above, then $a_0 = a_1 = a_2 = a_4 = -1$, and $a_3 = 1$.

Hereinafter, the autocorrelation functions of the 1st, 2nd, 3rd and 4th sequences are expressed by $\rho_{11}$, $\rho_{22}$, $\rho_{33}$ and $\rho_{44}$, respectively. The equation (301) is made by multiplying the right hand side of the equation (17.4) in Reference D by "n". Whether or not the "n" times multiplication is applied is a difference between normalizations of autocorrelation functions whether it is expressed so that the peak value of the primary lobe becomes to "1" or becomes to "n". It is possible to employ either one in case where relative levels of range sidelobes is considered. In anyone of the four autocorrelation functions $\rho_{11}$, $\rho_{22}$, $\rho_{33}$ and $\rho_{44}$ shown in FIGS. 48, levels of their range sidelobes are high. However, there may be a case that no range sidelobe is found as shown in FIG. 49 with respect to $$\rho_{11} + \rho_{22} + \Sigma_{33} + \rho_{44}$$

(hereinafter, this is referred to a composite autocorrelation function).

Incidentally, any combination of the two sequences chosen from the above four sequences will not provide a combination becoming a complementary sequence. This is clear from FIGS. 48(a)-48(d) that summing of arbitrarily selected two autocorrelation functions from these four will not provide a combination which gives no range sidelobe after the summing.

Figure 49:
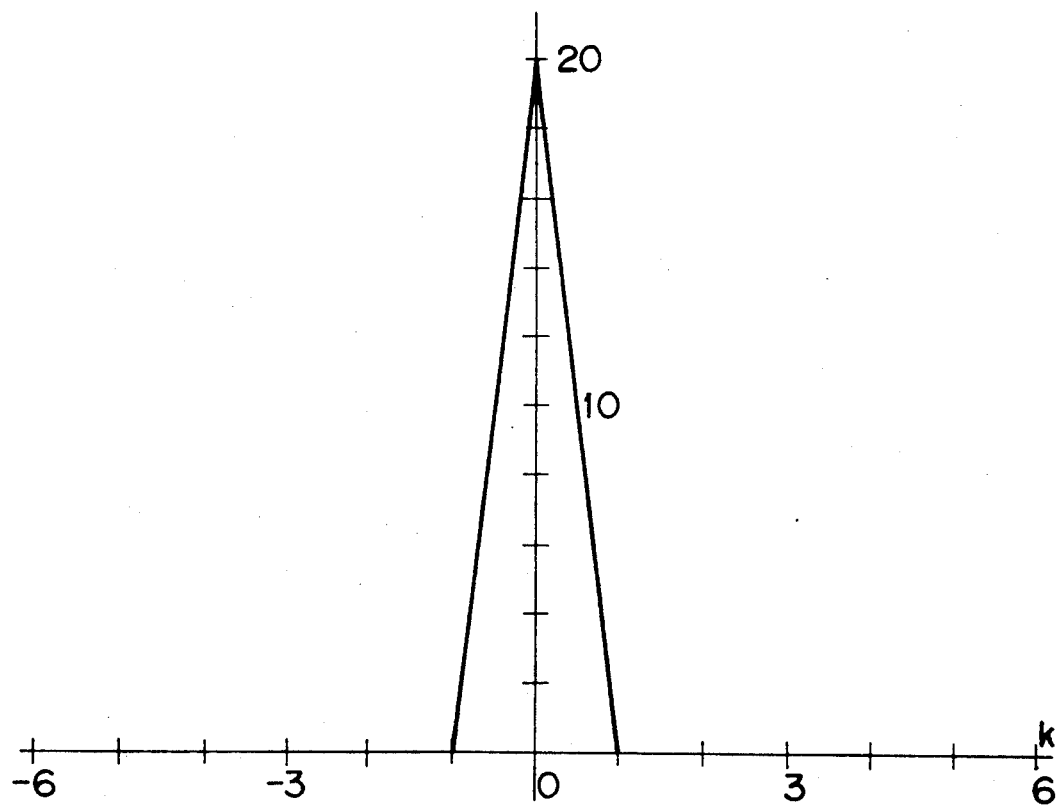
FIG. 49 shows a summing result of four autocorrelation functions in the sixth embodiment of the present invention.

As shown in FIG. 49, range sidelobes disappear when the four autocorrelation functions $\rho_{11}$, $\rho_{22}$, $\rho_{33}$ and $\rho_{44}$ are summed and, therefore, it is expected that there will be no range sidelobe in a composite compressed pulse, too.

This was confirmed as follows by utilizing a computer simulation process.

A compressed pulse is given, as discussed in Reference C, by a convolution of an autocorrelation function of a transmission signal with an impulse response of the ultrasonic probe 301. The impulse response used herein is that the response of the ultrasonic probe 301 when the transmission and receiving processes of ultrasonic waves are considered in total.

Figure 51A:
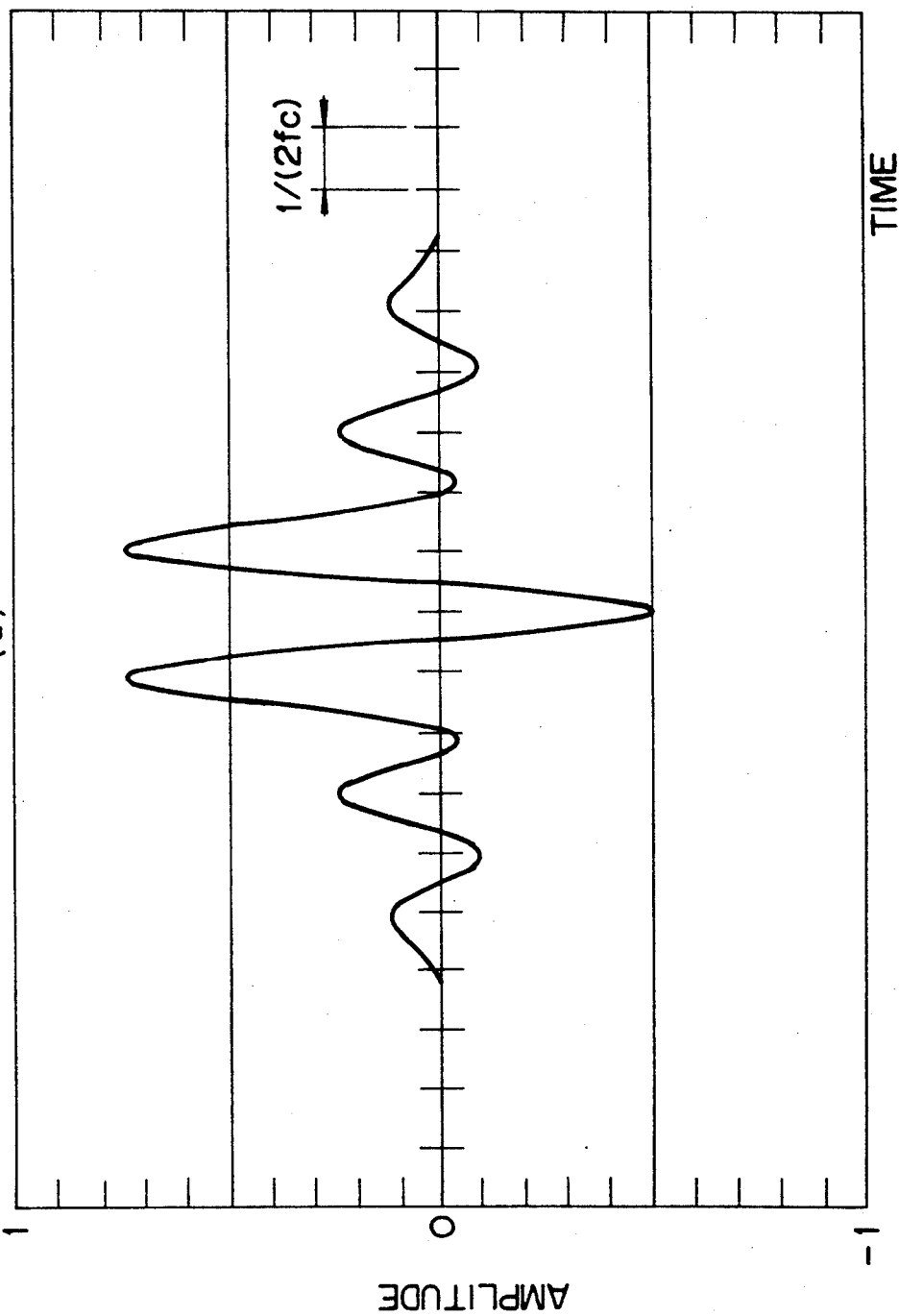
FIGS. 51(a), (b), (c) and (d) show a wave of operation result of 1st, 2nd, 3rd and 4th compressed pulses in the sixth embodiment of the present invention.
Figure 51B:
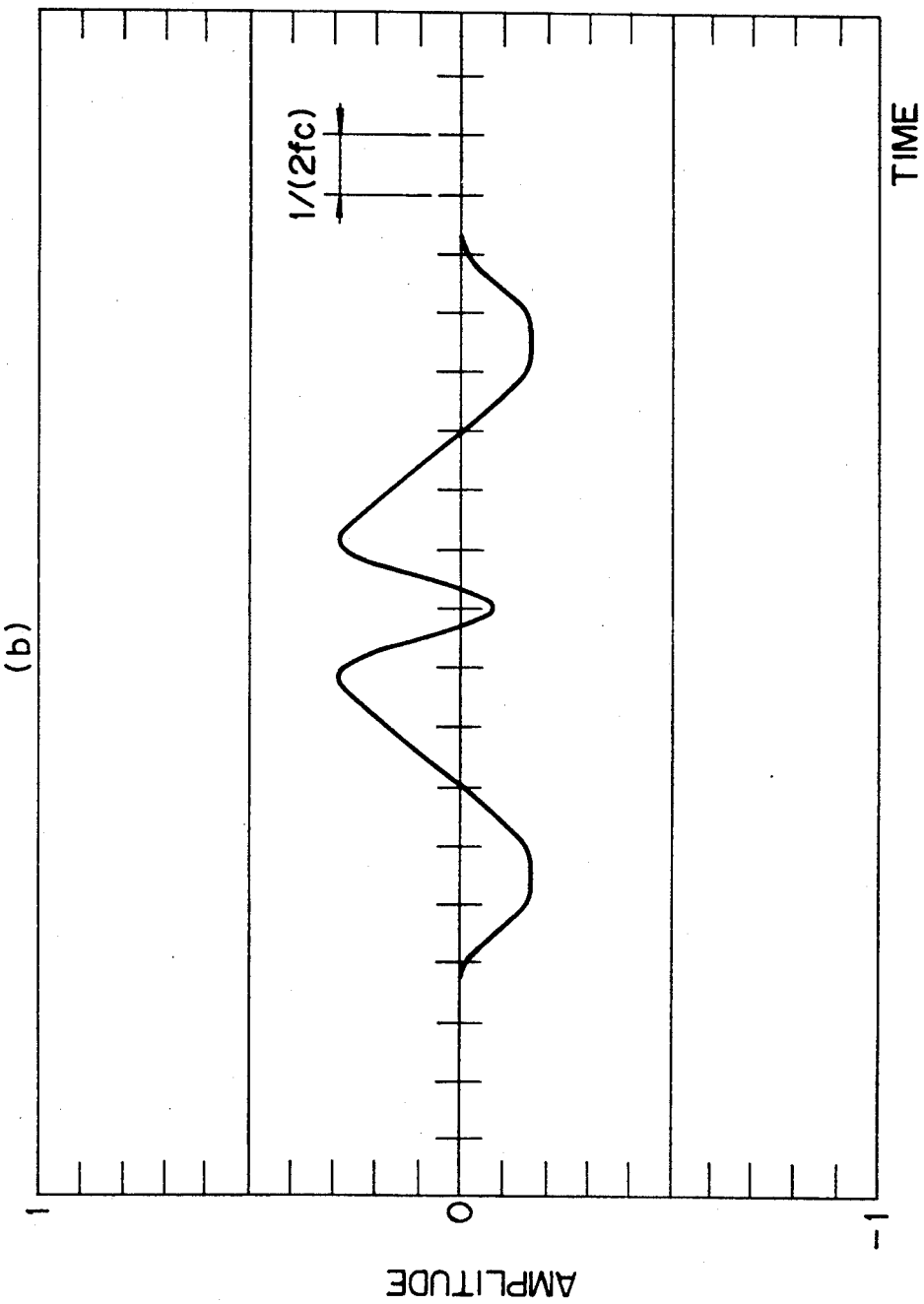
Figure 51C:
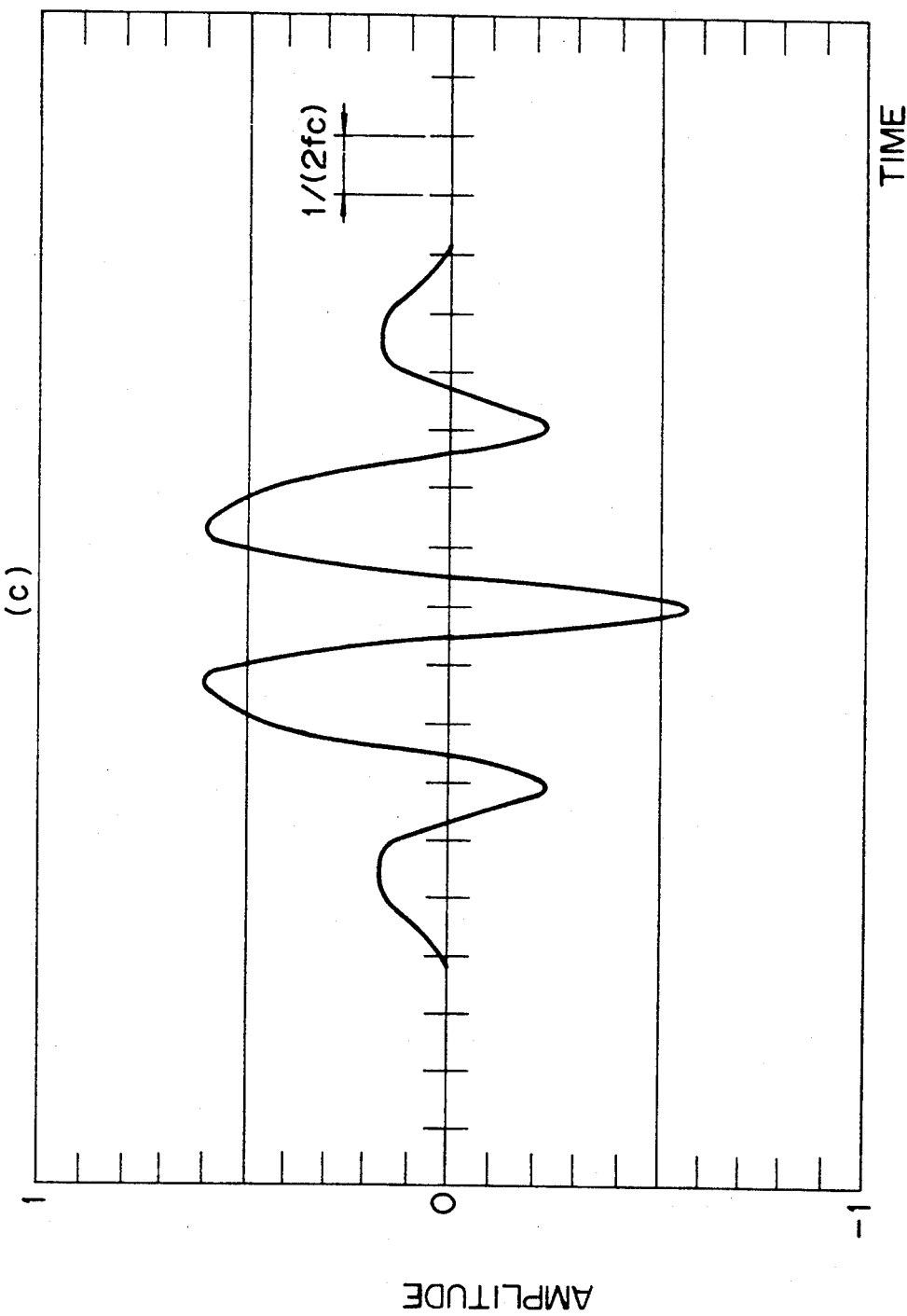
Figure 51D:
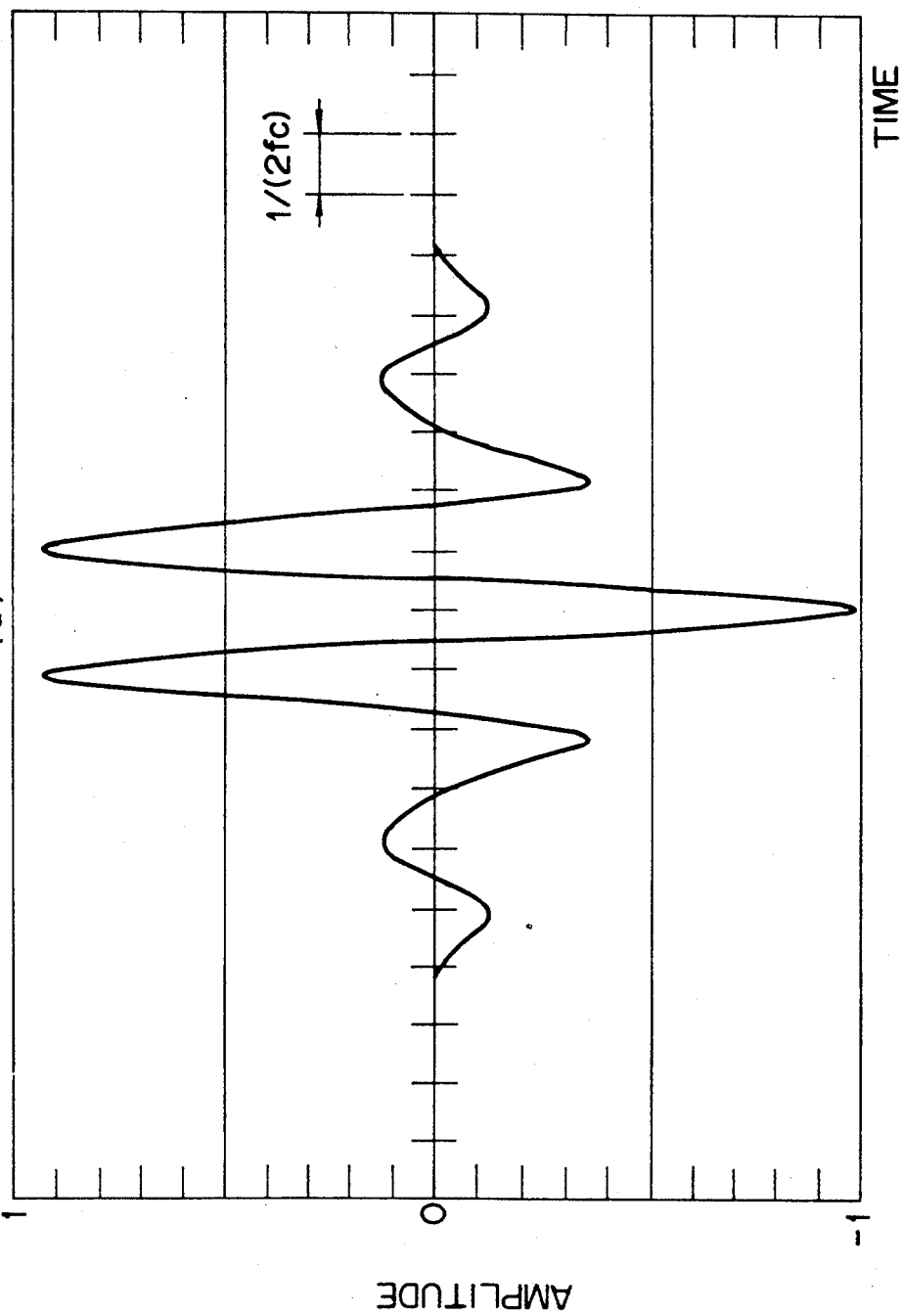
Figure 52:
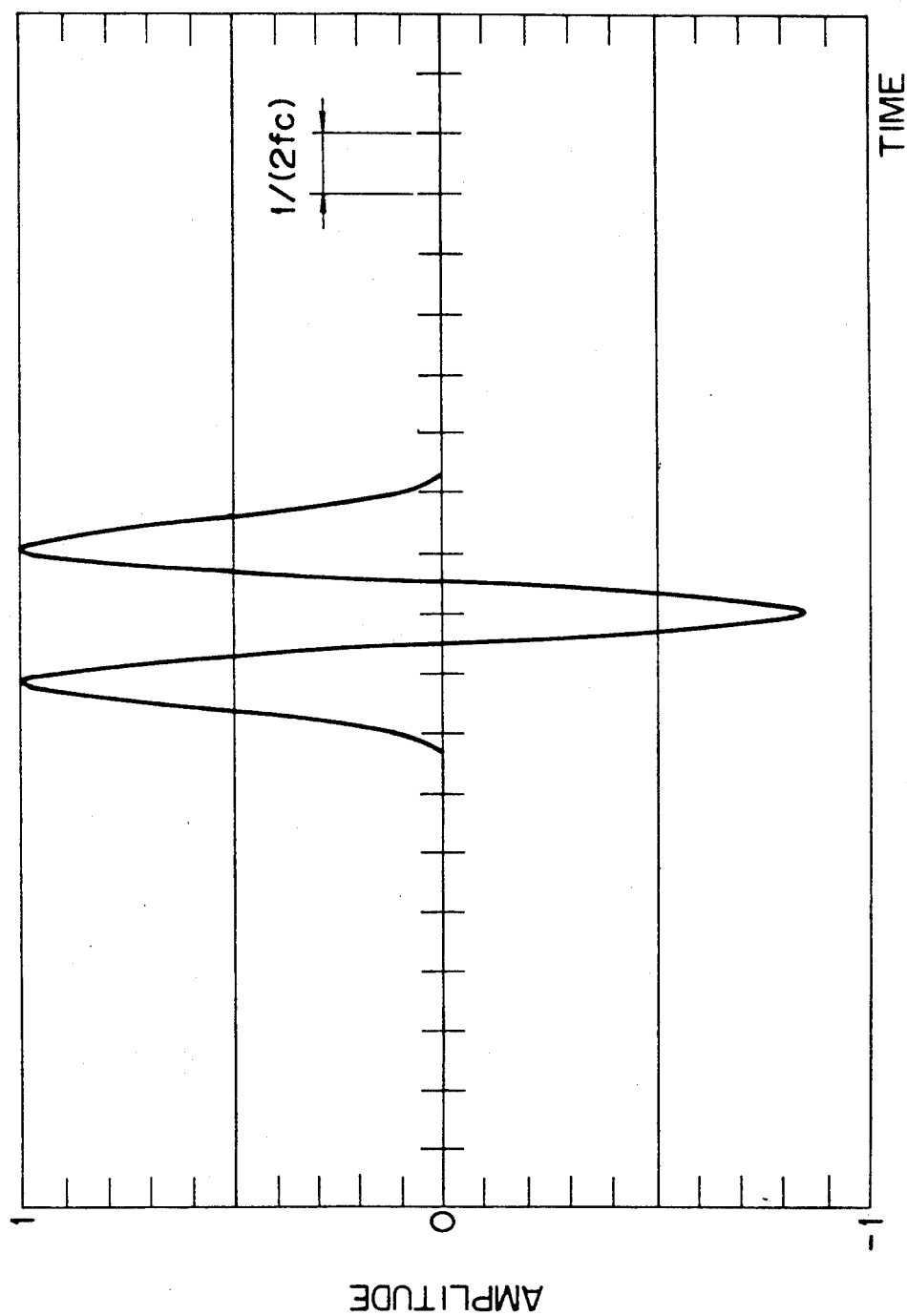
FIG. 52 shows a wave form of operation result of a composite compressed pulse in the sixth embodiment of the present invention.

Incidentally, FIG. 50 shows a wave form of the impulse response of the ultrasonic probe 301, FIGS. 51(a), (b), (c) and (d) illustrate the calculated wave forms of the 1st, 2nd, 3rd and 4th compressed pulses, and FIG. 52 shows the calculated wave form of the composite compressed pulse.

In the calculations, the duration time of the impulse response was set to be 1.5 cycles shown in FIG. 50. Incidentally, $f_c$ in the drawing designates a center frequency of the ultrasonic probe 301.

As explained above, the "i" th compressed pulse was obtained by performing a convolution integration with the "i"th autocorrelation function of the transmission signal shown in FIGS. 45(a)-(d) and the impulse response of the ultrasonic probe 301 shown in FIG. 50. Incidentally, the autocorrelation function of the "i"th transmission signal is the same as the autocorrelation function of the "i"th sequence shown in FIGS. 48(a)-(d) if a unit time $\delta$ is arranged to correspond to a unit bit in the abscissa shown in FIGS. 48(a)-(d). In this instance, $\delta = 1/(2f_c)$ was used in the calculation.

As shown in FIGS. 51(a)-(d), levels of range sidelobes are high in any of the four compressed pulses. However, as expected, there is completely no range sidelobe, as shown in FIG. 52, in the composite compressed pulse. In FIGS. 51(a)-(d) and 52, the above unit time $\delta$ was set to be $1/(2f_c)$ in the calculation; however, even with varying its value from the above in calculations, there is no range sidelobe in the composite compressed pulse.

Also, in the foregoing, the duration time of the impulse response of the ultrasonic probe 301 was set to be 1.5 cycle but even with varying the cycle number from the 1.5 cycle in calculations, there is no range sidelobe in the composite compressed pulse.

As discussed above, the sixth embodiment of the present invention was found to have a first merit that it can provide a composite compressed pulse completely free from range sidelobes by utilizing a sequence having a length of n=5, in which length no complementary sequences exist.

In this kind of ultrasonic non-destructive inspecting apparatus, an amount of an S/N ratio improvement SNRE is expressed by $$SNRE = nNB\delta \qquad (302)$$

as described in Reference B. This SNRE indicates an improvement degree of an S/N ratio after correlation processing of echo relative to an S/F ratio of the echo before correlation processing.

In the equation (302), "n" is a length of a sequence; "N" is a transmission repetition number on the assumptions that the compressed pulse is obtained by performing a correlation process per each transmission repetition period and that the result obtained by summing these compressed pulses is displayed as a final result. That is, N equals 2 in the case where a complementary sequence is used, and N equals 4 in the case where a multiple complementary sequence in the sixth embodiment is used; B is a bandwidth of echo; and $\delta$ is a unit time corresponding to a unit bit of a sequence. In the equation (302), the product of "n" and "$\delta$" corresponds to a pulse width of a transmission signal. It is understood from the equation (302) that as the pulse width (n$\delta$) of the transmission signal is made wider, the S/N ratio is made larger. Therefore, it is necessary to make a pulse width longer if improvement is to be considered only with respect to an S/N ratio.

However, if a pulse width of a transmission signal is made wider, there will be another problem which will be touched upon hereunder. During the period of transmitting a signal, echo cannot be accurately received because the transmission signal leaks, as shown in FIG. 47, to a receiving circuit side. Therefore, the duration time (n$\delta$) when the transmission signal continues becomes a dead time which cannot be utilized for inspection. This means that a region from the surface of the specimen S to the depth of (vn$\delta$)/2, corresponding in time to the half of the transmission signal pulse width, becomes a dead zone and cannot be inspected, wherein V is a propagation speed of the ultrasonic wave within the specimen S. The reason why one half of the pulse width is considered is that the ultrasonic wave experiences round trip within the specimen S. Therefore, it is necessary to make the transmission signal pulse width narrow for the purpose of narrowing the dead zone.

That is, the demand for improving an S/N ratio and the demand for narrowing a dead zone contradict with each other. Accordingly, it is necessary to determine a pulse width of a transmission signal so that a required S/N ratio can be obtained and a dead zone falls within a permissible range.

In order to set a pulse width (n$\delta$) of a transmission signal to be a required width determined as above, "n" or "$\delta$" may be appropriately changed.

Regarding "$\delta$", it is usually set near 1/(2$f_c$) so as to improve an efficiency of utilizing a transmission signal energy wherein $f_c$ is a central frequency of the ultrasonic probe 301. This is explained using FIG. 53.

Figure 53:
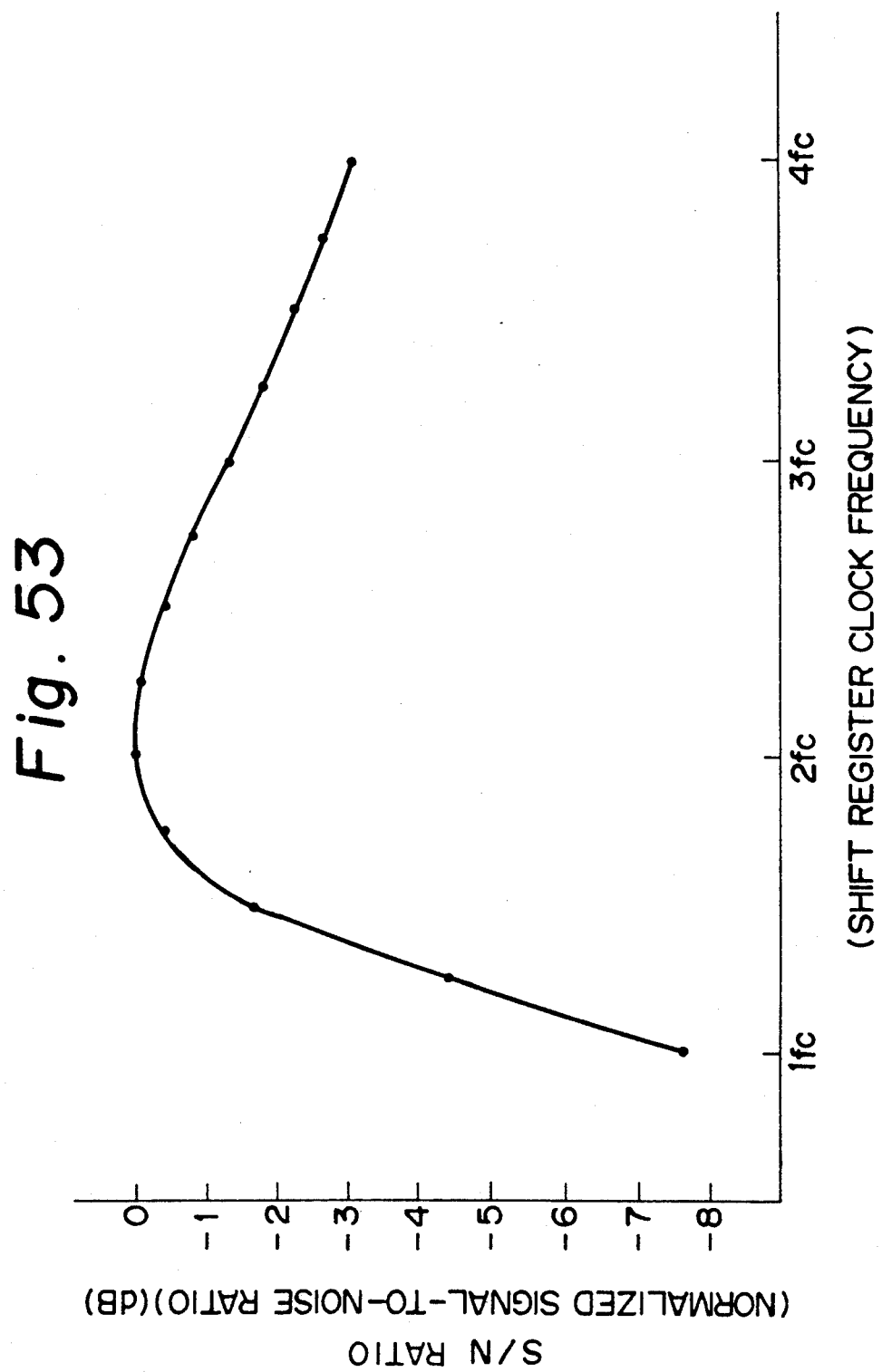
FIG. 53 is a drawing showing relationship between a clock pulse and an S/N ratio.

FIG. 53 shows the relationship, for example shown in Reference B, between a clock frequency and an S/N ratio.

In FIG. 53, relatively change of an S/N ratio due to the change of the efficiency of utilizing transmission signal energy is shown when a clock frequency given as a reciprocal of $\delta$ is changed.

As seen from FIG. 53, it is necessary to select a clock frequency at near 2$f_c$ in order to perform inspection with a good S/N ratio by raising the efficiency of utilizing a transmission signal energy. That is, "$\delta$" is to be selected at near 1/(2$f_c$).

Therefore, it is preferable to take the way for changing the length "n" of a sequence in order to set a pulse width (n$\delta$) to a desired width.

However, in a case where complementary sequences having advantage that there is no range sidelobe produced are utilized, complementary sequences are not necessarily available with respect to "n" for all the integer. Complementary sequences exist only for limited lengths and in the range below n=50, they exist only for 2, 4, 8, 10, 16, 20, 26, 32 and 40. Therefore, the following case may occur. If "n" is set as 8, for example, an S/N ratio is obtained at an enough value because the pulse width of the transmission signal is wide but the dead zone is out of a permissible range. On the other hand, if "n" is set as 4, the dead zone falls within a permissible range because the pulse width of the transmission signal is narrow but a required S/N ratio is not obtained. In such a case as above, if the multiple complementary sequence having n=5 between "4" and "8" as shown in the sixth embodiment of the present invention is utilized, a second advantage can be achieved in that an S/N ratio at a desired value can be obtained and a dead zone can be arranged within a permissible range so as to satisfy the inspecting requirements with retaining the first advantage that there is completely no range sidelobe produced.

Further, the following advantage can be expected if a multiple complementary sequence is utilized.

In the case where small flaw(s) existing adjacent the bottom surface of the specimen S are to be inspected, a level of echo from the small flaw is low while a level of echo from the bottom surface is high. If the pulse width of the transmission signal is wide, these two echoes having large difference with respect to their levels become to partially overlap with each other on the time axis. In order to process such overlapped echoes having large difference with respect to their levels, a large dynamic range is required for the receiving circuits such as the correlator 310A and so on. However, if the pulse width of the transmission signal is narrow and the above two echoes can be separated on the time axis, only the echo from the small flaw can be amplified and signal-processed by eliminating the bottom echo with applying a time gate to the bottom echo. In the case where such a signal processing as above is available, it would be suffice not to make the dynamic range of the receiving circuits large to such an extent as touched upon above. The above signal processing utilizing the time gate is essentially convenient, when the echo is inputted as data into a computer through an A/D converter and signal processing such as a correlation process or summing operation on the echo are performed in the computer, because the A/D converter with a few bits is suffice.

In the case where dynamic ranges of receiving circuits are not enough but the above signal processing utilizing a time gate is desired, if a complementary sequence with the length n=4 is used, the desired signal processing is possible but an S/N ratio is not enough, because the pulse width is narrow. On the other hand, if a complementary sequence with the length n=8 is used, an enough S/N ratio may be obtained but the desired signal processing cannot be performed, because the pulse width is wide.

In such a case as above, if a multiple complementary sequence having the length n=5 shown in the sixth embodiment is used, a third merit will be given in that the desired signal processing can be performed with an enough S/N ratio, because 5 is between 4 and 8. That is, the sixth embodiment using a multiple complementary sequence has advantages in that required value of dynamic ranges for signal receiving circuits can be set as small with retaining the first merit of zero range sidelobes because a range for selecting the sequence length is made broader, if multiple complementary sequences are used together with complementary sequences.

Further, the following advantage is available if a multiple complementary sequence is used.

There has been another problem in that, if noises overlapping on echo has some correlation with the sequences used for coding the transmission signals, compressed pulses derived from the noise may be mistaken as the compressed pulses produced from flaws of the specimen S because noises are also compressed.

In the case where a conventional complementary sequence is employed, only two sequences are used and the level of the compressed pulse derived from the noise is made to only a half at a displaying stage provided that there is a correlation between either one of the sequences and the noise and the result by summing and averaging the 1st and 2nd compressed pulses is displayed as the final result. Contrarily, in the sixth embodiment, if even there is a correlation between one of the sequences and the noise, the level of the compressed pulse derived from the noise is made to a quarter at the displaying stage when the result by summing and averaging the 1st, 2nd, 3rd and 4th compressed pulses is displayed as the final result, which is far smaller than that in the case where the conventional complementary sequence is used. Accordingly, the sixth embodiment of the present invention, wherein a multiple complementary sequence is used, provides the fourth merit, compared to a conventional ultrasonic non-destructive inspecting apparatus using a complementary sequence, in that probability of mistaking a compressed pulse derived from noise as that derived from a flaw is made small.

Further advantage is obtained as follows if a multiple complementary sequence is used. In the non-destructive inspecting apparatus using ultrasonic waves, transmission signals are, for example as shown in FIG. 46, repeated periodically with a certain cycle to drive the ultrasonic probe 301. At that occasion, ultrasonic waves are reflected multiple times in the specimen S and, thus, they may be sometimes received as echoes at the period when the subsequent transmission signal is repeated which is later than the period when the preceding transmission signal is repeated. This type echoes are referred to as reverberation echoes.

Figure 54:
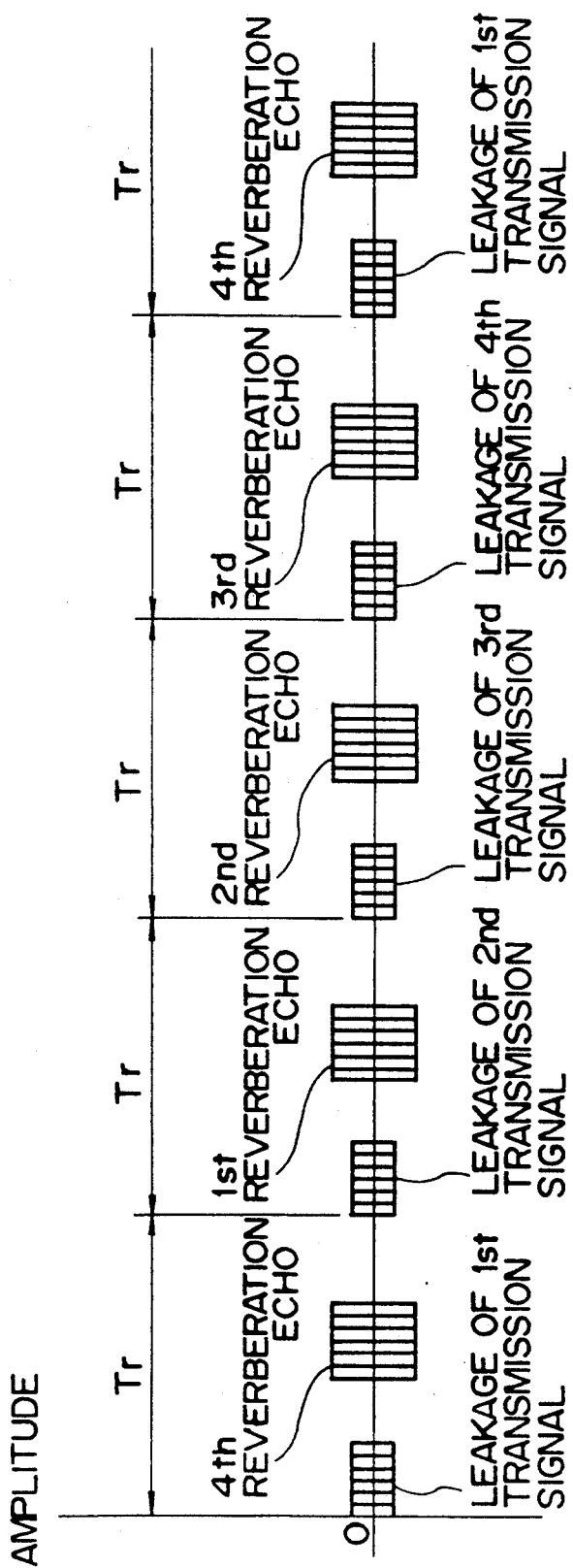
FIG. 54 shows a wave form of a reverberation echo in the sixth embodiment of the present invention.

FIG. 54 shows a wave form of the reverberation echoes in the sixth embodiment of the present invention.

In FIG. 54, there is shown a state that the reverberation echo is received at the next transmission repeating period succeeding the repeating period when the transmission signal was generated. In this case, levels of the reverberation echoes are the highest because, if the receiving of the reverberation echo becomes later, the level of the reverberation echo becomes smaller as it is received after passing through a longer transmission passage. Hereinafter, a reverberation echo derived from an "i"th transmission signal is referred to as the "i"th reverberation echo. A reverberation echo cannot be distinguished from an echo reflected once at a reflecting matter within a specimen S and received at the transmission repeating period when the transmission signal was generated. Therefore, the reverberation echo causes interference in inspection.

Figure 55:
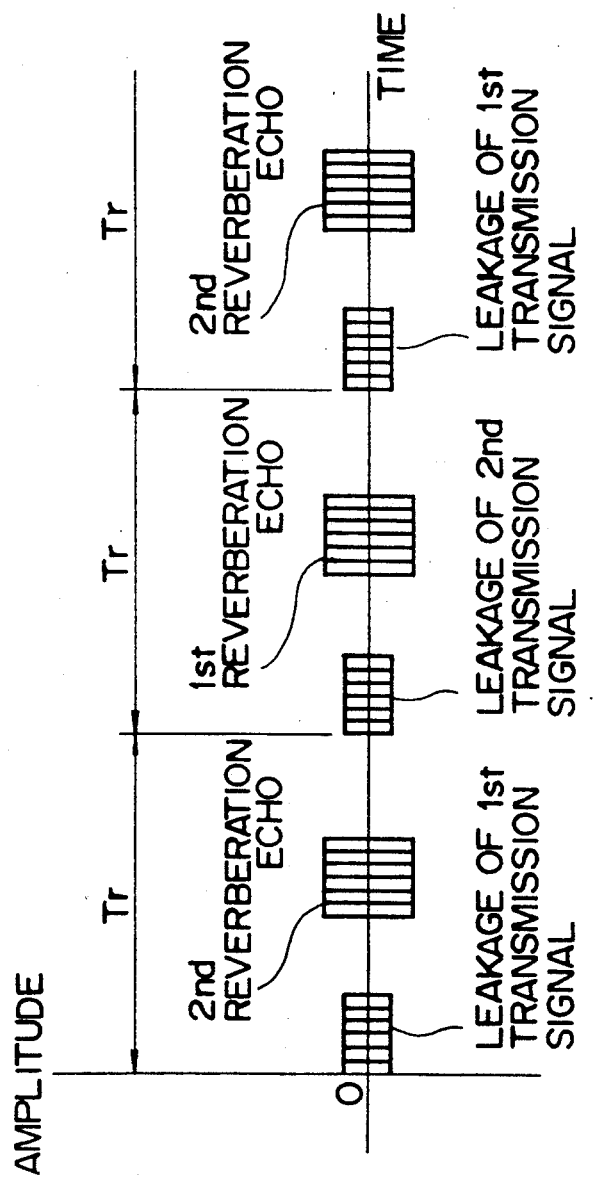
FIG. 55 shows a wave form of a reverberation echo in a conventional apparatus.

Referring to FIG. 55, comparison is made with respect to an interfering degree in inspection due to a reverberation echo between the sixth embodiment of the present invention and a conventional non-destructive ultrasonic inspecting apparatus.

FIG. 55 shows a wave form of a reverberation echo in a conventional non-destructive ultrasonic inspecting apparatus.

As a conventional apparatus, a case is considered where a complementary sequence having a length of 4 as noted below is employed.

1st sequence=$(+, +, +, -)$
2nd sequence=$(+, +, -, +)$

Now, a most serious case is considered where a level of a reverberation echo is highest, that is the reverberation echo is received at a next transmission repeating period succeeding the transmission repeating period when the transmission signal was generated.

In the conventional apparatus, the reverberation echo appears as indicated in FIG. 55. That is, the 1st reverberation echo is received at the transmission repeating period when the 2nd transmission signal is generated and the 2nd reverberation echo is received at the transmission repeating period when the 1st transmission signal is generated. Accordingly, a correlation operation is performed between the 1st reverberation echo and the 2nd transmission signal in signal processings of echoes. Similarly, a correlation operation is performed on the 2nd reverberation echo with the 1st transmission signal. The results of these two correlation operations are summed together and displayed as the final result.

The 1st and 2nd echoes are related to the transmission signals which are amplitude-coded by the 1st and 2nd sequences, respectively. Accordingly, as a level of a summing result of correlation functions (referred to as a composite cross-correlation function), namely $\rho_{12}+\rho_{21}$ becomes smaller relative to a primary lobe speak value of a composite autocorrelation function $\rho_{11}+\rho_{22}$, an interfering degree of the reverberation echo on inspection becomes smaller, wherein $\rho_{12}$ is a cross-correlation function of the 1st and 2nd sequences and $\rho_{21}$ is a cross-correlation function of the 2nd and 1st sequences.

The above composite cross-correlation function was calculated with respect to

1st sequence=$(+,+,+,-)$ and
2nd sequence=$(+,+,-,+)$ and it was divided by "8" which is the primary lobe peak value of the composite autocorrelation function. The result was $(0, \frac{3}{8}, \frac{3}{8}, \frac{3}{8}, \frac{3}{8}, 0)$. In this result, the peak value is $\frac{3}{8}=0.375$.

Incidentally, the cross-correlation function was obtained by the following equation $$\eta_{ab}(k) = \Sigma a_{j+k} \cdot b_j \quad (303)$$

(summing range: $0 \sim n-1$)
which was modified from the equation (17.8) shown on page 476 of Reference D.

In the equation (303), $p_{ab}$ is a cross-correlation function of sequences "a" and "b" having the same length "n" and the suffixes "j" and "k" are the same as those in the equation (301). In the equation (303), the right side of the equation (17.8) in Reference D was merely multiplied by "n" in order to harmonize with the equation (301) used in the calculation of the autocorrelation function.

For the purpose of comparison with respect to the above calculation result, similar calculation was performed in the sixth embodiment of the present invention shown in FIG. 54.

In FIG. 54, the 1st reverberation echo is received at the transmission repeating period when the 2nd transmission signal is generated, the 2nd reverberation echo is received at the transmission repeating period when the 3rd transmission signal is generated, the 3rd reverberation echo is received at the transmission repeating period when the 4th transmission signal is generated and the 4th reverberation echo is received at the transmission repeating period when the 1st transmission signal is generated. Therefore, in the respective stages of signal processing of echoes, correlation operations are performed between the 1st reverberation echo and the 2nd transmission signal, between the 2nd reverberation echo and the 3rd transmission signal, between the 3rd reverberation echo and the 4th transmission signal and between the 4th reverberation echo and the 1st transmission signal, respectively. And the results of these four correlation operations are summed together and displayed as the final result. Now, with respect to the following sequences employed in the sixth embodiment of the present invention, namely 1st sequence $= (-, -, -, +, -)$,
2nd sequence $= (-, -, -, +, +)$,
3rd sequence $= (-, -, +, -, -)$, and
4th sequence $= (-, -, +, -+)$, the cross-correlation function of the 1st and 2nd sequences (hereinafter referred to as $\rho_{12}$), the cross-correlation function of the 2nd and 3rd sequences (hereinafter referred to as $\rho_{23}$), the cross-correlation function of the 3rd and 4th sequences (hereinafter referred to as $\rho_{34}$) and the cross-correlation function of the 4th and 1st sequences (hereinafter referred to as $\rho_{41}$) were calculated and a composite cross-correlation function $\rho_{12} + \rho_{23} + \rho_{34} + \rho_{41}$ was obtained by summing the above four cross-correlation functions. Then, the above composite cross-correlation function was divided by "20" which is the peak value of the composite autocorrelation function $\rho_{11} + \rho_{22} + \rho_{33} + \rho_{44}$.

The result was (0, 0, 0, 1/5, 1/5, /15, 0, 0, 0).

The peak value in this calculation result is $$1/5 = 0.2$$

which is lower compared to the similar calculation result with respect to the conventional apparatus wherein the peak value is 0.375. Accordingly, there is a fifth advantage in the sixth embodiment in that interfering degrees of the reverberation echoes on inspection are expected to be lower.

Hereinabove, the explanation has been given with respect to the sixth embodiment of the present invention; however, the inventors have discovered that there are further multiple complementary sequences other than those explained above. Other examples of the multiple complementary sequences will be explained referring to FIGS. 56(a) and (b).

FIGS. 56(a) and (b) explain a multiple complementary sequence comprising four or six sequences. FIG. 56(a) shows examples of a multiple complementary sequence wherein there is no range sidelobe when autocorrelation functions of four sequences are summed together. The sequence is expressed by using the following relationship. That is "1" is corresponded to a sign "+", and "0" is corresponded to a sign "−", thus, for example, a sequence $(+, +, +, -)$ is represented by [1 1 1 0]. Next, [1 1 1 0] is regarded as a numeral value expressed by the binary system and this value is converted to a numeral value expressed by the decimal system. That is, [1 1 1 0] is converted to [14], with such relationship as above, one sequence is corresponded to one numerical value.

Incidentally, as disclosed on page 476 of Reference D, a sequence wherein its signals "+" and "−" are reversed with respect to a certain binary sequence and a sequence wherein the order of its components are reversed possess the same autocorrelation function. For instance, relative to a sequence $(+, +, +, -)$, anyone of sequences $(-, -, -, +), (-, +, +, +)$ and $(+, -, -, -)$ possesses the same autocorrelation function. If the above four sequences are expressed by numeral values by using the relationship explained above, they will be expressed as [14], [1], [7] and [8] but, the minimum value [1] is used in FIG. 56(a) to represent the remaining three.

FIG. 56(b) shows examples of multiple complementary sequences wherein there is no range sidelobe if autocorrelation functions of six sequences are summed. The meaning of the numeral values are the same as those in FIG. 56(a). In the case where the multiple complementary sequence shown in FIG. 56(b) is employed, six transmission signals which are amplitude coded by the respective sequences are sequentially generated, and six echoes respectively corresponding to the above transmission signals are correlation processed with using the respective corresponding transmission signals to obtain six compressed pulses. Thereafter, if these pulses are summed as a composite compressed pulse which is displayed, the same effect and advantage as those in the sixth embodiment are expected.

FIGS. 56(a) and (b) show several examples of a multiple complementary sequence and the inventors found further examples other than those shown in FIGS. 56(a) and (b). For example, it is found that, in the case of a multiple complementary sequence comprising four sequences, the following combinations are available for a various length (n).

| n | number of combinations |
|---|---|
| 2 | 1 |
| 3 | 1 |
| 7 | 34 |
| 8 | 56 |
| 9 | 477 |

The term "combination" is the same as that employed in FIGS. 56(a) and (b). Further, the number is counted on the premise that if a sequence in which signs of components are reversed, an order of components is inverted and/or both reversing and inverting of components are effected is regarded as the same as the original and not counted as an additional example. The same principle is applied in the following description.

For a multiple complementary sequence comprising six sequences, the following table is given.

| n | number of combinations |
|---|---|
| 2 | 1 |
| 6 | 48 |

Also, it is found that there is no multiple complentary sequence comprising six sequences when the length, n=3, 5 or 7.

For a multiple complementary sequence comprising eight sequences, the following combinations are found.

| n | number of combinations |
|---|---|
| 2 | 1 |
| 3 | 1 |
| 4 | 5 |
| 5 | 35 |
| 6 | 517 |

Incidentally, if a multiple sequence comprising four sequences each having a length of "n" is expressed by:

$$\{a_0, a_1, \ldots, a_{n-1}\},$$

$$\{b_0, b_1, \ldots, b_{n-1}\},$$

$$\{c_0, c_1, \ldots, c_{n-1}\},$$

$$\{d_0, d_1, \ldots, d_{n-1}\},$$

then $$\{a_0, b_0, a_1, b_1, \ldots a_{n-1}, b_{n-1}\},$$

$$\{a_0, -b_0, a_1, -b_1, \ldots a_{n-1}, -b_{n-1}\},$$

$$\{c_0, d_0, c_1, d_1, \ldots c_{n-1}, d_{n-1}\},$$

$$\{c_0, -d_0, c_1, -d_1, \ldots c_{n-1}, -d_{n-1}\},$$

become a multiple complementary sequence having a length of "2n". Similarly, a new multiple complementary sequence having a double length can be produced from a multiple complementary sequence comprising more than six sequences.

In the foregoing, explanation has been made on the system for amplitude-coding of transmission signals by using a multiple complementary sequence; however, the present invention is not limited to such a system as above and it is also applicable to a system for phase-coding of transmission signals.

Figure 57:
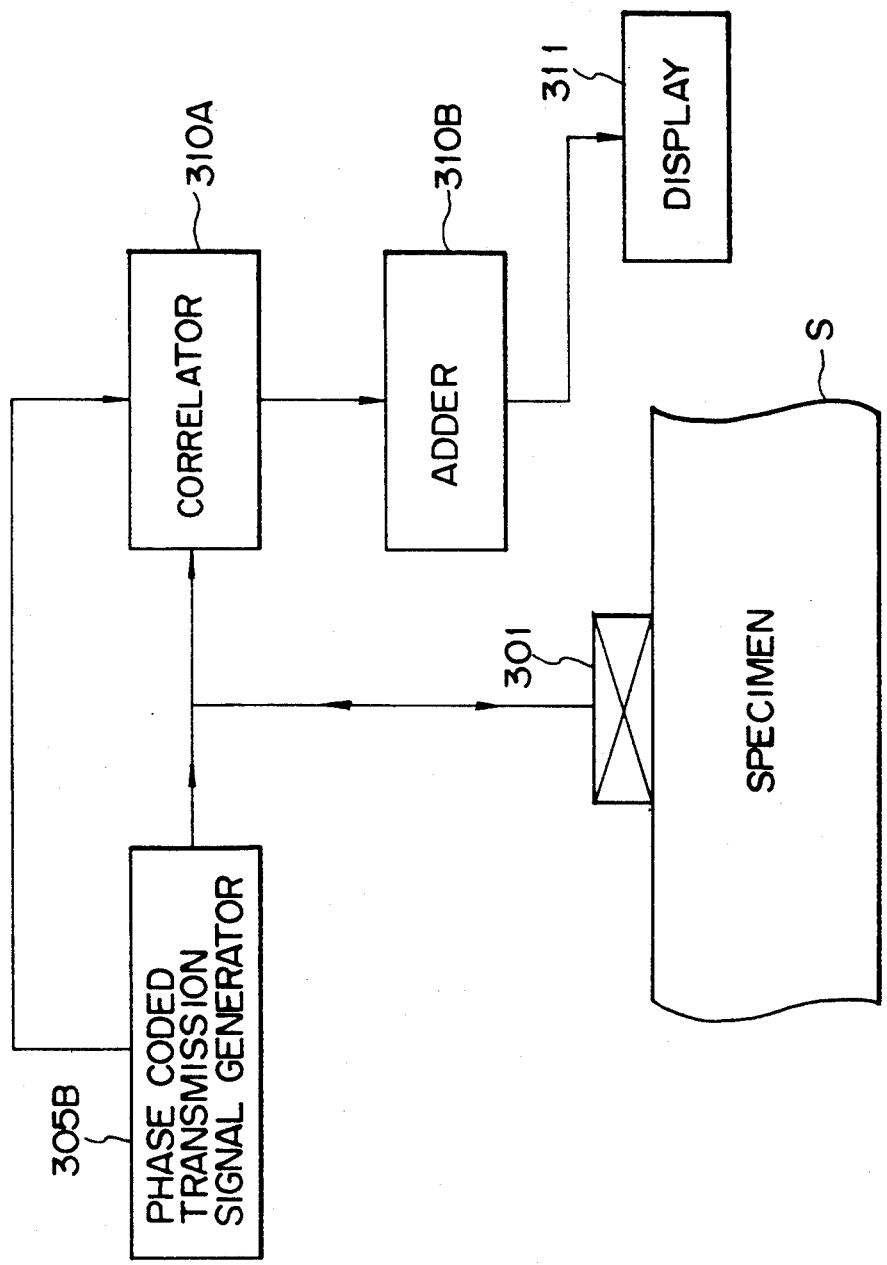
FIG. 57 shows a seventh embodiment according to the present invention.

A construction of a seventh embodiment of the present invention is now explained referring to FIG. 57.

FIG. 57 is a block diagram showing the seventh embodiment according to the present invention wherein the components other than a phase coded transmission signal generator 305B are the same as those in the above sixth embodiment.

In FIG. 57, the seventh embodiment is constructed by the same components as those in the above sixth embodiment and others, namely the phase coded transmission signal generator 305B connected to the ultrasonic probe 301 and the correlator 310A.

Figure 58:
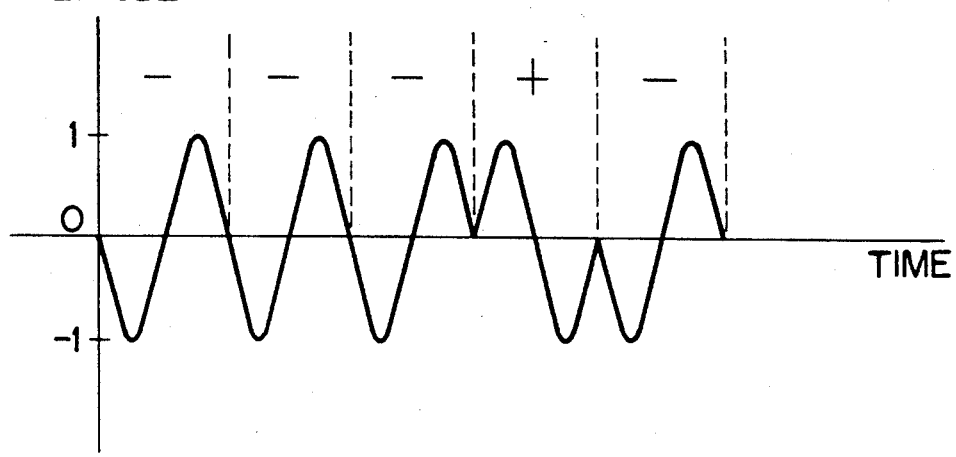
FIGS. 58(a), (b), (c) and (d) show a wave form of a transmission signal in the seventh embodiment of the present invention.
Figure 58:
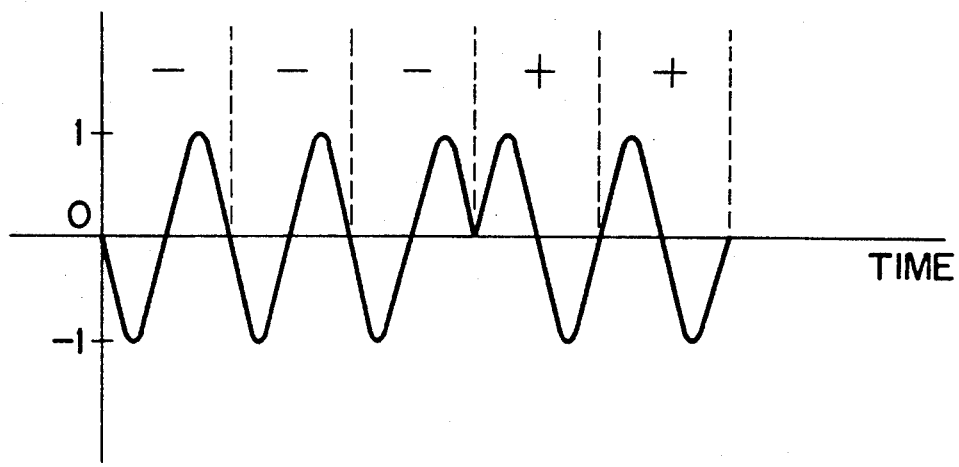
Figure 58:
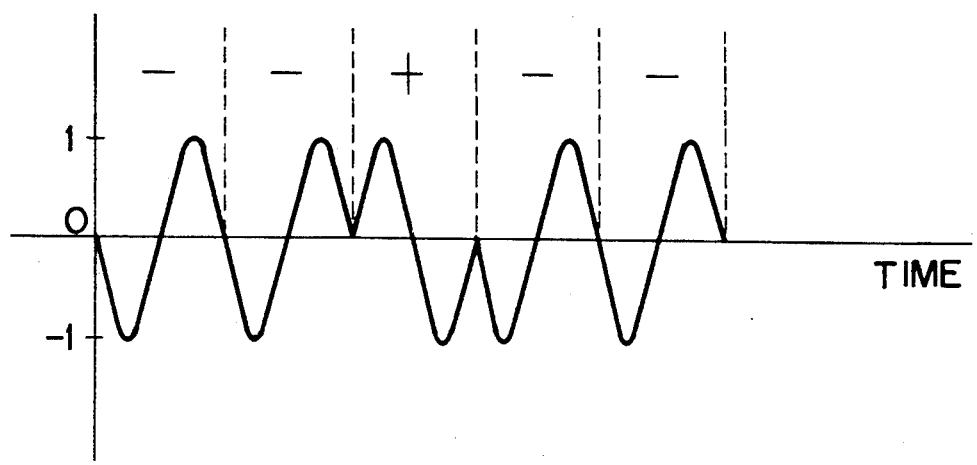
Figure 58:
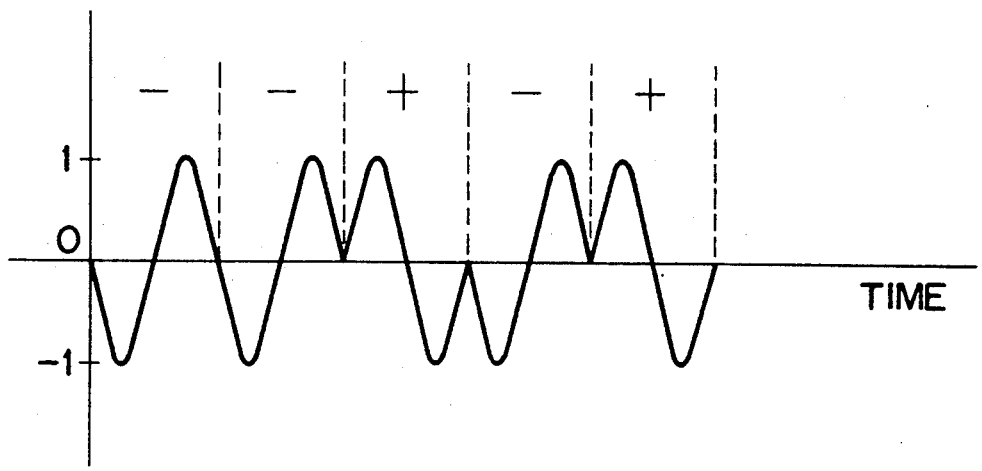

An operation of the seventh embodiment is explained referring to FIGS. 58(a), (b), (c) and (d).

FIGS. 58(a), (b), (c) and (d) show wave forms of transmission signals generated by the phase coded transmission signal generator 305B in the seventh embodiment.

In FIGS. 58(a), (b), (c) and (d), the transmission signal is coded in its phase by using the same four sequences as those in the sixth embodiment. In order to facilitate understanding the relationship between the four sequences and coding of transmission signals, signs of sequences are inserted in the drawings.

Incidentally, the method for phase-coding has been explained in connection with FIG. 15.

In the seventh embodiment, the transmission signals of the sixth embodiment shown in FIGS. 45(a)-(d) are replaced by the transmission signals show in FIGS. 58(a)-(d), respectively to drive the ultrasonic probe 301. The signal processing of echoes is the same as that of the sixth embodiment.

Now, the effect and advantage of the seventh embodiment are explained hereunder.

In the seventh embodiment of the present invention, the effect and advantage similar to those of the sixth embodiment can be given and, further, the frequency characteristics of the transmission signal can be approached to become close to, as seen in the previous embodiments, the frequency response characteristics of the ultrasonic probe 301. Accordingly, it is expected in the seventh embodiment that efficiency for utilizing the transmission energy can be improved.

In the sixth and seventh embodiments, a system has been explained that a compressed pulse has been obtained by performing a correlation operation between the echo and transmission signal. However, as explained in the previous embodiments, the present invention is not limited to the system above and it is applicable to a system wherein a filtering means having frequency response characteristics in both transmitting and receiving is prepared, a reference signal is generated by passing the transmission signal through the filtering means and a correlation operation is performed between the reference signal and the echo to obtain a compressed pulse.

Figure 59:
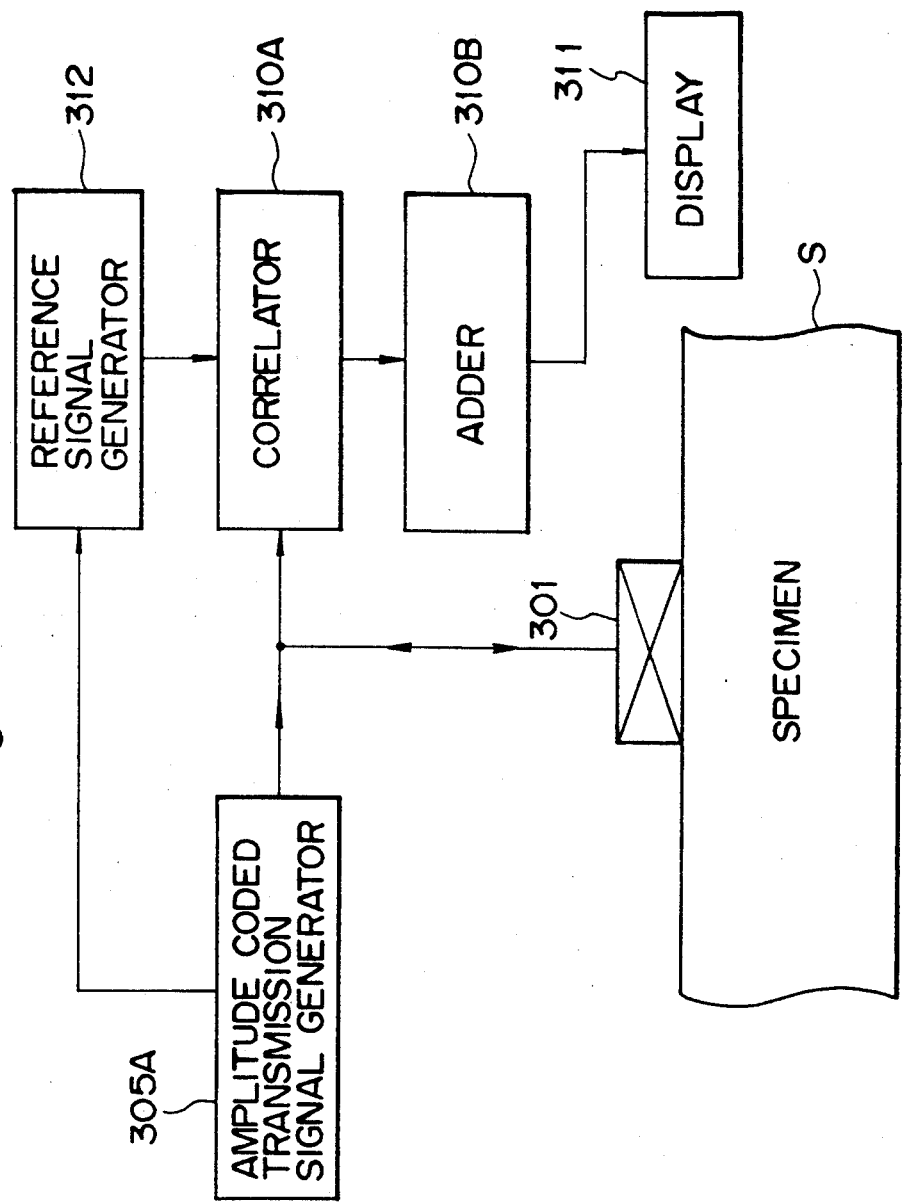
FIG. 59 shows a eighth embodiment in block diagram according to the present invention.

Now a eighth embodiment of the present invention to which the above system is applied is explained referring to FIG. 59.

FIG. 59 shows the eighth embodiment in a block diagram and all the components excluding a reference signal generator 312 are the same as those in the sixth embodiment.

In FIG. 59, the eighth embodiment is constructed to comprise the same components as those in the sixth embodiment and others, namely the reference signal generator 312 connected at its input side to the amplitude coded transmission signal generator 305A and at its output side to the correlator 310A.

The reference signal generator 312 serves as a filter having a composite frequency response characteristics in both transmitting and receiving and generates reference signals to be used for the correlation operation on echoes.

In the eighth embodiment, it is expected, as in the previous embodiments, that further improvement with respect to an S/N ratio is available compared to the system wherein the echo is correlation processed with the transmission signal. The reason is explained below. Since the bandwidth of the ultrasonic probe 301 is finite, the filtering function of the probe 301 affects the signals at the time of transmission and receiving, and so the wave form of the transmission signal and that of the echo do not match. However, in the eighth embodiment, the reference signal having the same wave form as that of the echo is generated by the reference signal generator 312 and it is used for performing a correlation operation on the echo. This matter corresponds to a signal processing wherein the echo is passed through a matched filter and the matched filter provides an advantage that a desired signal burried within noise can be received with the maximum S/N ratio.

It is, thus, expected in the eighth embodiment that the above effect and advantage may be available in addition to those of the sixth embodiment.

Incidentally, when the ultrasonic waves propagating within the specimen S accompanies frequency characteristics, filtering function due to such characteristics may simultaneously affects the signals. In such an occasion as above, the reference signal generator 312 may be replaced by a filter having the frequency characteristics of the composite frequency response characteristics of the probe 301 in both transmitting and receiving and the frequency characteristics of the specimen S.

Figure 60:
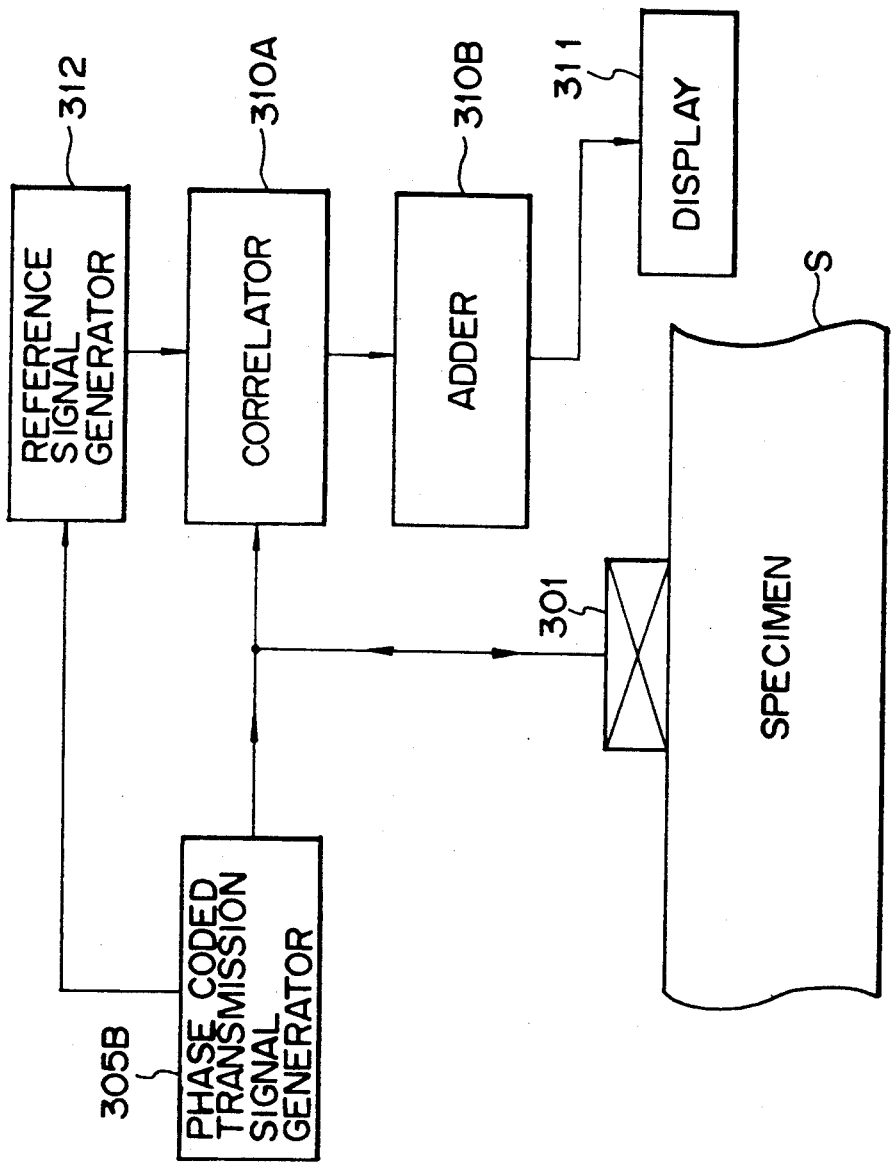
FIG. 60 shows a ninth embodiment according to the present invention.

A ninth embodiment according to the present invention is explained hereunder referring to FIG. 60.

FIG. 60 shows the ninth embodiment in a block diagram and all the components thereof except for the reference signal generator 311 are the same as those of the seventh embodiment.

In FIG. 60, the ninth embodiment is constructed to comprise the same components as those of the seventh embodiment referred to above and others, namely the reference signal generator 311 connected at its input side to the phase coded transmission signal generator 305B and at the output side to the correlator 310A.

In the ninth embodiment, it is expected that the same effect and advantage as those of the eighth embodiment can be provided in addition to those of the seventh embodiment.

Now, a tenth embodiment of the present invention is explained hereunder referring to FIG. 61.

FIG. 61 shows a tenth embodiment in a block diagram and all the components except for ultrasonic probes 301A and 301B are the same as those of the ninth embodiment.

In FIG. 61, the tenth embodiment is constructed to comprise the same components as those of the ninth embodiment and others, namely the transmission ultrasonic probe 301A connected at its input side to the phase coded transmission signal generator 305B and the receiving ultrasonic probe 301B connected at its output side to the correlator 310A.

In the tenth embodiment, a composite frequency characteristics is employed as the frequency response characteristics of the reference signal generator 312, the composite frequency characteristics comprising the frequency response characteristics of the ultrasonic probe 301A exhibited at the time of transmitting and the frequency response characteristics of the receiving ultrasonic probe 301B exhibited at the time of receiving.

The same effect and advantage as those of the ninth embodiment are available in the tenth embodiment.

It is, of course, possible to apply the transmission ultrasonic probe 301A and the receiving ultrasonic probe 301B to the sixth, seventh and ninth embodiments of the present invention.

Also, the application of the present invention is not limited to the previous embodiments and a combination of a multiple complementary sequence comprising more than four sequences and a conventional complementary sequence may be employed.

For instance, in the case where a conventional complementary sequence having a length of "4" and a multiple complementary sequence comprising four sequences each having a length of "5" employed in the sixth embodiment are used in combination, six sequences in total are used to repeatedly generate six transmission signals obtained either in amplitude-coding or phase-coding in a manner similar to that in the sixth and seventh embodiments, and the echoes are processed in a manner similar to those in the eighth, ninth and tenth embodiments. In this case, it provides an advantage in that an S/N ratio is further improved to become larger since N in the right side of the equation (302) becomes "6". Also, a length of the conventional complementary sequence and that of a multiple complementary sequence may not be necessarily the same and they may differ as explained above.

Also, plurality of multiple complementary sequences and plurality of complementary sequences may be used in combination as in the foregoing for coding transmission signals. In this case, N in the right side of the equation (302) becomes large whereby an S/N ratio is made larger. In addition to the above, since many kinds of sequences are available, a freedom is made large in selecting a combination of a sequence for coding the "i"th transmission signal and a sequence for coding the (i+1)th transmission signal so that the cross-correlation function of the two sequences is made small. Therefore, interferences of reverberation echoes affecting on inspection are effectively reduced.

In many of the embodiments explained above, the ultrasonic probe has been explained about a case where it is contacted with the specimen. However, the transmission of the ultrasonic waves between the probe and the specimen may be performed through an appropriate medium such as water. Further the present invention can be applied to a transmitter-receiver system of an independent element constituting an array type ultrasonic probe.

In the foregoing, explanation has been given with respect to detection of a flaw or flaws in the specimen; however, the present invention is not limited to such usage as above and it is also applicable to other purposes such as diagnosis, and medical applications, etc.

Also, the embodiments utilizing ultrasonic waves have been explained. However, the present invention is not limited to usage of ultrasonic waves but it is applicable to employ other waves such as electric waves or micro-waves.

Summarizing the above, with the use of the present invention, the following effects and advantages are expected.

a. Range sidelobes can be reduced to substantially zero in a composite compressed pulse;

b. Required values for dynamic ranges of a receiving circuits can be reduced;

c. Affection of noises on inspection can be reduced;

d. Affection of reverberation echoes on inspection can be reduced;

e. Improved S/N ratios are available; and f. efficiency for utilizing transmission energy can be improved.

The present invention has been explained in detail with respect to the embodiments referring to drawings; however, it is not limited to those explained and it can be modified/changed by those skilled in the art within the scope and gist of the present invention as defined in the claims appended.

What is claimed is:

1. A detecting apparatus characterized by comprising:
    a first transmission signal generating means for generating a first transmission signal which has a wave form comprising smoothly curved portions;
    a second transmission signal generating means for generating a second transmission signal which has a wave form comprising smoothly curved portions;
    a first transmitting means for transmitting waves to an object by said first transmission signal;
    a second transmitting means for transmitting waves to said object by said second transmission signal;
    a first receiving means for receiving a first echo corresponding to said first transmission signal;
    a second receiving means for receiving a second echo corresponding to said second transmission signal;
    a first correlation operation means for performing a first correlation operation with respect to said first echo;
    a second correlation operation means for performing a second correlation operation with respect to said second echo; and
    a processing means for processing results of said first and second correlation operations, whereby a signal which has substantially zero range sidelobes is obtained.

2. A detecting apparatus as claimed in claim 1 characterized in that wave form of said first transmission signal corresponds to a first sequences and wave form of said second transmission signal corresponds to a second sequence.

3. A detecting apparatus as claimed in claim 2 characterized in that said first and said second sequences are finite binary sequences.

4. A detecting apparatus as claimed in claim 1 wherein each of said first and second transmission signals has a wave form constituted by substantially sinusoidal portions.

5. A detecting apparatus as claimed in claim 2 characterized in that each of said first and said second transmission signals has a wave form which is obtained by arranging a wave form portion including a frequency component $f_0$ along a time axis according to an appearance order of plus sign and minus sign in the corresponding sequence and according to a rule of changing the phases by 180° in the wave form portions corresponding to the minus signs compared to the other wave form portions corresponding to the plus signs.

6. A detecting apparatus as claimed in claim 2 characterized in that a wave form of each of said first and said second transmission signals is phase-coded waveform by using the corresponding sequence.

7. A detecting apparatus as claimed in claim 1 wherein said results of said first and second correlation operations are substantially in complementary relationship.

8. A detecting apparatus as claimed in claim 1 wherein said first and second transmission signals are substantially in complementary relationship.

9. A detecting apparatus as claimed in claim 2 wherein said first and said second sequences are substantially in complementary relationship.

10. A detecting apparatus as claimed in claim 2 wherein said first and said second sequences are substantially in complementary relationship.

11. A detecting apparatus as claimed in claim 1 wherein said first correlation operation is performed between said first echo and a first reference signal; and said second correlation operation is performed between said second echo and a second reference signal.

12. A detecting apparatus as claimed in claim 11 wherein said first and second reference signals are said first and second transmission signals, respectively.

13. A detecting apparatus as claimed in claim 11 wherein said first reference signal is a first echo related to said first transmission signal from the surface or the bottom of said object; and said second reference signal is a second echo related to said second transmission signal from the surface or the bottom of said object.

14. A detecting apparatus as claimed in claim 11 wherein said first reference signal is one computed based on frequency response characteristics of a signal path from an output portion of said first transmission signal generating means through said object to an input portion of said first correlation operation means and said first transmission signal; and said second reference signal is one computed based on frequency response characteristics of signal path from an output portion of said second transmission signal generating means through said object to an input portion of said second correlation operation means and said second transmission signal.

15. A detecting apparatus as claimed in claim 11 characterized in that said first reference signal is an echo from a portion of a trial object when waves are transmitted to said trial object from said first transmitting means by said first transmission signal; and said second reference signal is an echo from said portion of said trial object when waves are transmitted to said trial object from said second transmitting means by said second transmission signal.

16. A detecting apparatus as claimed in claim 11 characterized in that said first reference signal is a signal which has the wave form similar to that of said first echo; and said second reference signal is a signal which has the wave form similar to that of said second echo.

17. A detecting apparatus as claimed in claim 14 characterized in that each of said frequency characteristics includes frequency characteristics relating to reflection of a reflection body in said object.

18. A detecting apparatus as claimed in claim 1 characterized in that plurality of correlation operations are performed with respect to each of said first and said second echoes.

19. A detecting apparatus as claimed in claim 18 characterized in that each of said correlation operations is a correlation operation between each of a plurality of reference signals and each of said first and said second echoes and a wave form of each of said reference signals is different from wave forms of the other reference signals.

20. A detecting apparatus as claimed in claim 5 characterized in that said frequency component $f_0$ is determined by frequency characteristics of said transmitting means, frequency characteristics of said object and frequency characteristics of said receiving means whereby a signal to noise ratio is maximized.

21. A detecting apparatus as claimed in claim 1 characterized in that a center frequency of each of said first and said second transmission signals is determined by frequency characteristics of said transmitting means, frequency characteristics of said object and frequency characteristics of said receiving means whereby a signal to noise ratio is maximized.

22. A detecting apparatus as claimed in claim 1 characterized in that said first and said second transmission signals are alternately generated in timing.

23. A detecting apparatus as claimed in claim 2 characterized in that said first and said second sequences are alternately generated in timing whereby said first and said second transmission signals are alternately generated in timing.

24. A detecting apparatus as claimed in claim 1 characterized in that said waves transmitted from said transmitting means to said object are ultrasonic wave.

25. A detecting apparatus, comprising:
transmission signal generating means for generating a first transmission signal which has a waveform comprising smoothly curved portions and a second transmission signal which has a waveform comprising smoothly curved portions;
transmitting and receiving means for transmitting waves to an object respectively by said first and second transmission signals and for receiving first and second echoes from the object respectively corresponding to said first and second transmission signals;
correlation operation means for performing a first correlation operation with respect to said first echo and a second correlation operation with respect to said second echo; and
processing means for processing results of said first and second correlation operations, whereby a signal which has substantially zero range sidelobes is obtained,
wherein said first and said second transmission signal are alternately generated in timing.

26. A detecting apparatus as claimed in claim 25 wherein a single generator is commonly utilized as said transmission signal generating means.

27. A detecting apparatus as claimed in claim 25 wherein a single transmitter and a single receiver are commonly utilized as said transmitting and receiving means.

28. A detecting apparatus as claimed in claim 25 wherein a single correlator is commonly utilized as said correlation operation means.

29. A detecting apparatus as claimed in claim 25 wherein the wave form of said first transmission signal corresponds to a first sequence and a wave form of said second transmission signal corresponds to a second sequence.

30. A detecting apparatus as claimed in claim 25 wherein each of said first and second transmission signals has a wave form constituted by substantially sinusoidal portions.

31. A detecting apparatus as claimed in claim 25 wherein said results of said first and second correlation operations are substantially in complementary relationship.

32. A detecting apparatus as claimed in claim 25 wherein said first and second transmission signals are substantially in complementary relationship.

33. A detecting apparatus as claimed in claim 29 wherein said first and said second sequences are substantially in complementary relationship.

34. A detecting apparatus as claimed in claim 25 wherein said first correlation operation is performed between said first echo and a first reference sign; and said second correlation operation is performed between said second echo and a second reference signal.

35. A detecting apparatus as claimed in claim 34 wherein said first and second reference signals are said first and second transmission signals, respectively.

36. A detecting apparatus, comprising:
transmission signal generating means for generating a first transmission signal which has a waveform comprising smoothly curved portions and a second transmission signal which has a waveform comprising smoothly curved portions;
transmitting and receiving means for transmitting waves to an object respectively by said first and second transmission signals and for receiving first and second echoes from the object respectively corresponding to said first and second transmission signals;
correlation operation means for performing a first correlation operation with respect to said first echo and a second correlation operation with respect to said second echo; and
processing means for processing results of said first and second correlation operations, whereby a signal which has substantially zero range sidelobes is obtained,
wherein said first correlation operation is performed between said first echo and a first reference signal, and said second correlation operation is performed between said second echo and a second reference signal,
and wherein said first reference signal is a first echo related to said first transmission signal from the surface or the bottom of said object, and said second reference signal is a second echo related to said second transmission signal from the surface or the bottom of said object.

37. A detecting apparatus, comprising:
transmission signal generating means for generating a first transmission signal which has a waveform comprising smoothly curved portions and a second transmission signal which has a waveform comprising smoothly curved portions;
transmitting and receiving means for transmitting waves to an object respectively by said first and second transmission signals and for receiving first and second echoes from the object respectively corresponding to said first and second transmission signals;
correlation operation means for performing a first correlation operation with respect to said first echo and a second correlation operation with respect to said second echo; and
processing means for processing results of said first and second correlation operations, whereby a signal which has substantially zero range sidelobes is obtained,
wherein said first correlation operation is performed between said first echo and a first reference signal, and said second correlation operation is performed between said second echo and a second reference signal, and wherein said first reference signal is one computed based on frequency response characteristics of a signal path from an output portion of said transmission signal generating means through said object to an input portion of said correlation operation means and said first transmission signal, and said second reference signal is one computed based on frequency response characteristics of a signal path from an output portion of said transmission signal generating means through said object to an input portion of said correlation operation means and said second transmission signal.

38. A detecting apparatus, comprising:
transmission signal generating means for generating a first transmission signal which has a waveform comprising smoothly curved portions and a second transmission signal which has a waveform comprising smoothly curved portions;
transmitting and receiving means for transmitting waves to an object respectively by said first and second transmission signals and for receiving first and second echoes from the object respectively corresponding to said first and second transmission signals;
correlation operation means for performing a first correlation operation with respect to said first echo and a second correlation operation with respect to said second echo; and
processing means for processing results of said first and second correlation operations, whereby a signal which has substantially zero range sidelobes is obtained,
wherein said first correlation operation is performed between said first echo and a first reference signal, and said second correlation operation is performed between said second echo and a second reference signal,
and wherein said first reference signal is an echo from a portion of a trial object when waves are transmitted to said trial object from said transmitting and receiving means by said first transmission signal, and said second reference signal is an echo from said portion of said trial object when waves are transmitted to said trial object from said transmitting and receiving means by said second transmission signal.

39. A detecting apparatus, comprising:
transmission signal generating means for generating a first transmission signal which has a waveform comprising smoothly curved portions and a second transmission signal which has a waveform comprising smoothly curved portions;
transmitting and receiving means for transmitting waves to an object respectively by said first and second transmission signals and for receiving first and second echoes from the object respectively corresponding to said first and second transmission signals;
correlation operation means for performing a first correlation operation with respect to said first echo and a second correlation operation with respect to said second echo; and
processing means for processing results of said first and second correlation operations, whereby a signal which has substantially zero range sidelobes is obtained,
wherein said first correlation operation is performed between said first echo and a first reference signal, and said second correlation operation is performed between said second echo and a second reference signal,
and wherein said first reference signal is a signal which has the wave form similar to that of said first echo, and said second reference signal is a signal which has the wave form similar to that of said second echo.

40. A detecting apparatus as claimed in claim 37, wherein each of said frequency characteristics includes frequency characteristics relating to reflection of a reflection body in said object.

41. A detecting apparatus as claimed in claim 25 wherein a center frequency of each of said first and said second transmission signals is determined by frequency characteristics of said transmitting and receiving means and by frequency characteristics of said object whereby a signal to a noise ratio is maximized.

42. A detecting apparatus as claimed in claim 25 wherein said waves transmitted from said transmitting and receiving means to said object are ultrasonic waves.

43. A detecting apparatus comprising:
a single generator for generating a first transmission signal which has a wave form comprising smoothly curved portions, and for generating a second transmission signal which has a wave form comprising smoothly curved portions;
a first transmitting means for transmitting waves to an object by said first transmission signal;
a second transmitting means for transmitting waves to said object by said second transmission signal;
a first receiving means for receiving a first echo corresponding to said first transmission signal;
a second receiving means for receiving a second echo corresponding to said second transmission signal;
a first correlation operation means for performing a first correlation operation with respect to said first echo;
a second correlation operation means for performing a second correlation operation with respect to said second echo; and
a processing means for processing results of said first and second correlation operations, whereby a signal which has substantially zero range sidelobes is obtained.

44. A detecting apparatus comprising:
a first transmission signal generating means for generating a first transmission signal which has a wave form comprising smoothly curved portions;
a second transmission signal generating means for generating a second transmission signal which has a wave form comprising smoothly curved portions;
a single transmitter for transmitting waves to an object by said first transmission signal and for transmitting waves to said object by said second transmission signal;
a first receiving means for receiving a first echo corresponding to said first transmission signal;
a second receiving means for receiving a second echo corresponding to said second transmission signal;
a first correlation operation means for performing a first correlation operation with respect to said first echo;
a second correlation operation means for performing a second correlation operation with respect to said second echo; and
a processing means for processing results of said first and second correlation operations, whereby a signal which has substantially zero range sidelobes is obtained.

45. A detecting apparatus comprising:
a first transmission signal generating means for generating a first transmission signal which has a wave form comprising smoothly curved portions;
a second transmission signal generating means for generating a second transmission signal which has a wave form comprising smoothly curved portions;
a first transmitting means for transmitting waves to an object by said first transmission signal;
a second transmitting means for transmitting waves to said object by said second transmission signal;
a single receiver for receiving a first echo corresponding to said first transmission signal and for receiving a second echo corresponding to said second transmission signal;
a first correlation operation means for performing a first correlation operation with respect to said first echo;
a second correlation operation means for performing a second correlation operation with respect to said second echo; and
a processing means for processing results of said first and second correlation operations, whereby a signal which has substantially zero range sidelobes is obtained.

46. A detecting apparatus comprising:
a first transmission signal generating means for generating a first transmission signal which has a wave form comprising smoothly curved portions;
a second transmission signal generating means for generating a second transmission signal which has a wave form comprising smoothly curved portions;
a first transmitting means for transmitting waves to an object by said first transmission signal;
a second transmitting means for transmitting waves to said object by said second transmission signal;
a first receiving means for receiving a first echo corresponding to said first transmission signal;
a second receiving means for receiving a second echo corresponding to said second transmission signal;
a single correlator for performing a first correlation operation with respect to said first echo and for performing a second correlation operation with respect to said second echo; and
a processing means for processing results of said first and second correlation operations, whereby a signal which has substantially zero range sidelobes is obtained.

47. A detecting apparatus comprising:
a first transmission signal generating means for generating a first transmission signal which has a wave form comprising smoothly curved portions;
a second transmission signal generating means for generating a second transmission signal which has a wave form comprising smoothly curved portions;
a single common transmitting/receiving means for transmitting waves to an object by said first transmission signal, for transmitting waves to said object by said second transmission signal, for receiving a first echo corresponding to said first transmission signal, and for receiving a second echo corresponding to said second transmission signal;
a first correlation operation means for performing a first correlation operation with respect to said first echo;
a second correlation operation means for performing a second correlation operation with respect to said second echo; and
a processing means for processing results of said first and second correlation operations, whereby a signal which has substantially zero range sidelobes is obtained.

* * * * *